US011299780B2

(12) United States Patent
Green

(10) Patent No.: US 11,299,780 B2
(45) Date of Patent: Apr. 12, 2022

(54) METHODS OF PRODUCING NUCLEIC ACID LIBRARIES

(71) Applicant: The Regents of the University of California, Oakland, CA (US)

(72) Inventor: Richard E. Green, Santa Cruz, CA (US)

(73) Assignee: The Regents of the University of California, Oakland, CA (US)

(*) Notice: Subject to any disclaimer, the term of this patent is extended or adjusted under 35 U.S.C. 154(b) by 424 days.

(21) Appl. No.: 16/316,268

(22) PCT Filed: Jul. 13, 2017

(86) PCT No.: PCT/US2017/041974
§ 371 (c)(1),
(2) Date: Jan. 8, 2019

(87) PCT Pub. No.: WO2018/013837
PCT Pub. Date: Jan. 18, 2018

(65) Prior Publication Data
US 2020/0149098 A1 May 14, 2020

Related U.S. Application Data

(60) Provisional application No. 62/362,904, filed on Jul. 15, 2016.

(51) Int. Cl.
*C12Q 1/6806* (2018.01)
*C12Q 1/6869* (2018.01)

(52) U.S. Cl.
CPC ......... *C12Q 1/6869* (2013.01); *C12Q 1/6806* (2013.01); *C12Q 2521/501* (2013.01); *C12Q 2525/179* (2013.01); *C12Q 2525/191* (2013.01); *C12Q 2525/204* (2013.01); *C12Q 2533/107* (2013.01); *C12Q 2563/179* (2013.01); *C12Q 2565/631* (2013.01)

(58) Field of Classification Search
CPC .............. C12Q 1/6806; C12Q 1/6869; C12Q 2521/501; C12Q 2525/179; C12Q 2525/191; C12Q 2525/204; C12Q 2533/107; C12Q 2563/179; C12Q 2565/631
See application file for complete search history.

(56) References Cited

U.S. PATENT DOCUMENTS

| | | |
|---|---|---|
| 5,744,306 A | 4/1998 | Murtagh et al. |
| 6,013,438 A | 1/2000 | Didenko et al. |
| 6,057,101 A * | 5/2000 | Nandabalan ....... C12N 15/1055 506/10 |
| 6,261,774 B1 | 7/2001 | Pagratis et al. |
| 6,261,782 B1 | 7/2001 | Lizardi et al. |
| 6,607,878 B2 | 8/2003 | Sorge |
| 6,670,120 B1 | 12/2003 | Schmidt et al. |
| 6,677,121 B2 | 1/2004 | Lizardi et al. |
| 6,773,886 B2 | 8/2004 | Kaufman et al. |
| 6,927,028 B2 | 8/2005 | Dennis et al. |
| 7,166,429 B2 | 1/2007 | Van Eijk et al. |
| 7,282,335 B2 | 10/2007 | Gocke et al. |
| 7,723,077 B2 | 5/2010 | Young et al. |
| 7,741,463 B2 | 6/2010 | Gormley et al. |
| 7,838,647 B2 | 11/2010 | Hahn et al. |
| 8,168,388 B2 | 5/2012 | Gormley et al. |
| 8,192,941 B2 | 6/2012 | Kuersten |
| 8,420,319 B2 | 4/2013 | Mikawa |
| 8,563,478 B2 | 10/2013 | Gormley et al. |
| 8,932,816 B2 | 1/2015 | Kuersten |
| 9,416,406 B2 | 8/2016 | Kuersten |
| 9,506,113 B2 | 11/2016 | Eshoo et al. |
| 9,546,399 B2 | 1/2017 | Amorese et al. |
| 9,580,751 B2 | 2/2017 | Hahn et al. |

(Continued)

FOREIGN PATENT DOCUMENTS

| | | |
|---|---|---|
| WO | WO 1989001526 | 2/1989 |
| WO | WO 1997027330 | 7/1997 |

(Continued)

OTHER PUBLICATIONS

Adey et al. (2010) "Rapid, Low-Input, Low-Bias Construction of Shotgun Fragment Libraries by High-Density in Vitro Transposition", Genome Biology, 11: R119:17 pages.
Altschul et al. (1997) "Gapped BLAST and PSI-BLAST: A New Generation of Protein Database Search Programs", Nucleic Acids Research, 25(17):3389-3402.
Ansari et al. (1993) "In Situ End-Labelling Detects DNA Strand Breaks in Apoptosis and Other Physiological and Pathological States", The Journal of Pathology, 170:1-8.
Aravanis et al. (2017) "Next-Generation Sequencing of Circulating Tumor DNA for Early Cancer Detection", Cell, 168:571-574.

(Continued)

*Primary Examiner* — David C Thomas

(74) *Attorney, Agent, or Firm* — Brian E. Davy; Bozicevic, Field & Francis LLP

(57) ABSTRACT

Provided are methods of producing nucleic acid libraries. In certain aspects, the methods include combining target nucleic acids (e.g., 5' phosphorylated nucleic acids) and an oligonucleotide pool. Oligonucleotides of the oligonucleotide pool may include complementarity regions of varying length and nucleotide sequence, and a complementarity region identification sequence. In such aspects, the combining is under conditions in which oligonucleotides of the oligonucleotide pool hybridize to nucleic acids of the target nucleic acids (e.g., 5' phosphorylated nucleic acids) having overhang regions that are complementary in sequence and have corresponding lengths with respect to the complementarity regions of the oligonucleotides. Compositions and kits that find use, e.g., in practicing the methods of the present disclosure are also provided.

24 Claims, 9 Drawing Sheets

(56) References Cited

U.S. PATENT DOCUMENTS

| | | | |
|---|---|---|---|
| 9,605,313 | B2 | 3/2017 | Cantor et al. |
| 9,624,534 | B2 | 4/2017 | Kuersten |
| 9,783,799 | B2 | 10/2017 | Kim et al. |
| 9,834,816 | B2 | 12/2017 | Kuersten |
| 9,834,822 | B2 | 12/2017 | Talasaz |
| 9,890,375 | B2 | 2/2018 | Geng et al. |
| 9,982,255 | B2 | 5/2018 | Varley et al. |
| 10,011,866 | B2 | 7/2018 | Eshoo et al. |
| 10,017,807 | B2 | 7/2018 | Srinivasan et al. |
| 10,227,587 | B2 | 3/2019 | Zhang et al. |
| 10,240,191 | B2 | 3/2019 | Kuersten |
| 10,316,357 | B2 | 6/2019 | Makarov et al. |
| 2002/0058256 | A1 | 5/2002 | Rothberg et al. |
| 2002/0106649 | A1 | 8/2002 | Lizardi et al. |
| 2002/0142309 | A1 | 10/2002 | Dattagupta |
| 2003/0082556 | A1 | 5/2003 | Kaufman et al. |
| 2003/0104363 | A1 | 6/2003 | Arguello et al. |
| 2003/0165923 | A1 | 9/2003 | Li et al. |
| 2003/0165963 | A1 | 9/2003 | Dattagupta |
| 2003/0219878 | A1 | 11/2003 | Lindbo et al. |
| 2004/0006033 | A1 | 1/2004 | Zhu |
| 2004/0265888 | A1 | 12/2004 | Kaufman et al. |
| 2009/0317818 | A1 | 12/2009 | Ehrich et al. |
| 2010/0105049 | A1 | 4/2010 | Ehrich et al. |
| 2010/0311602 | A1 | 12/2010 | Levy et al. |
| 2011/0319290 | A1 | 12/2011 | Raymond et al. |
| 2013/0005585 | A1 | 1/2013 | Anderson et al. |
| 2013/0012399 | A1 | 1/2013 | Myers et al. |
| 2015/0004604 | A1* | 1/2015 | Eshoo .................... C12P 19/34 435/6.11 |
| 2015/0051088 | A1 | 2/2015 | Kim |
| 2015/0132763 | A1 | 5/2015 | Amorese et al. |
| 2016/0032396 | A1 | 2/2016 | Diehn et al. |
| 2018/0002731 | A1 | 1/2018 | Wu et al. |
| 2018/0016631 | A1 | 1/2018 | Van Eijk |
| 2018/0142235 | A1 | 5/2018 | Zhang et al. |
| 2019/0194649 | A1 | 6/2019 | Raine et al. |
| 2020/0149098 | A1 | 5/2020 | Green |
| 2021/0010081 | A1 | 1/2021 | Shendure et al. |

FOREIGN PATENT DOCUMENTS

| | | |
|---|---|---|
| WO | 1997046704 | 12/1997 |
| WO | 2000039333 | 7/2000 |
| WO | WO 2006056480 | 6/2006 |
| WO | WO 2007140417 | 12/2007 |
| WO | WO 2007147063 | 12/2007 |
| WO | WO 2009032779 | 3/2009 |
| WO | WO 2009032781 | 3/2009 |
| WO | WO 2010033639 | 3/2010 |
| WO | WO 2010115016 | 10/2010 |
| WO | WO 2011034631 | 3/2011 |
| WO | WO 2011143659 | 11/2011 |
| WO | WO 2011156529 | 12/2011 |
| WO | WO 2012103154 | 8/2012 |
| WO | 2014210353 | 12/2014 |
| WO | 2015118077 | 8/2015 |
| WO | WO 2015134552 | 9/2015 |
| WO | WO 2016081798 | 5/2016 |
| WO | WO 2018013837 | 1/2018 |
| WO | WO 2019140201 | 7/2019 |

OTHER PUBLICATIONS

Aymard et al. (2014) "Transcriptionally Active Chromatin Recruits Homologous Recombination at DNA Double-Strand Breaks", Nature Structural & Molecular Biology, 21:366-374.

Barra et al. (2015) "EDTA-Mediated Inhibition of DNases Protects Circulating Cell-Free DNA from Ex Vivo Degradation in Blood Samples", Clinical Biochemistry, 48:976-981.

Butler (2019) "Fundamentals of Forensic DNA Typing", Academic Press, 1st Edition, 486 pages.

Canela et al. (2016) "DNA Breaks and End Resection Measured Genome-wide by End Sequencing", Molecular Cell, 63(5):898-911.

Chan et al. (2016) "Second Generation Noninvasive Fetal Genome Analysis Reveals De Novo Mutations, Single-Base Parental Inheritance, and Preferred DNA Ends", Proceedings of the National Academy of Sciences, 113: E8159-E8168.

Chitrabamrung et al. (1981) "Serum Deoxyribonuclease I and Clinical Activity in Systemic Lupus Erythematosus", Rheumatology International, 1:55-60.

Collins (2004) "The Comet Assay for DNA Damage and Repair: Principles, Applications, and Limitation", Molecular Biotechnology, 26:249-261.

Crawford et al. (2006) "DNase-Chip: A High-Resolution Method to Identify DNase I Hypersensitive Sites Using Tiled Microarrays", Nature Methods, 3(7):503-509.

Crosetto et al. (2013) "Nucleotide-Resolution DNA Double-Strand Breaks Mapping by Next-Generation Sequencing", Nature Methods, 10(4):361-365.

Crowley et al. (2013) "Liquid Biopsy: Monitoring Cancer-Genetics in the Blood", Nature Reviews Clinical Oncology, 13 pages.

Dabney et al. (2013) "Complete Mitochondrial Genome Sequence of a Middle Pleistocene Cave Bear Reconstructed from Ultrashort DNA Fragments", Proceedings of the National Academy of Sciences, 110(39):15758-15763.

Dekker et al. (1960) "Nucleic Acids Selected Topics Related to their Enzymology and Chemistry", Review of Biochemistry, 29:453-474.

Didenko et al. (1996) "Presence of Double-strand Breaks with Single-base 3' Overhangs in Cells Undergoing Apoptosis but Not Necrosis", The Journal of Cell Biology, 135(5):1369-1376.

Diehl et al. (2008) "Circulating Mutant DNA to Assess Tumor Dynamics", Nature Medicine, 14(9):985-990.

Dorsett et al. (2014) "HCoDES Reveals Chromosomal DNA End Structures with Single Nucleotide Resolution", Molecular Cell, 56(6):808-818.

Ershova et al. (2017) "Circulating Cell-Free DNA Concentration and DNase I Activity of Peripheral Blood Plasma Change in Case of Pregnancy with Intrauterine Growth Restriction Compared to Normal Pregnancy", Biomedical Reports, 7:319-324.

Fan et al. (2008) "Noninvasive Diagnosis of Fetal Aneuploidy by Shotgun Sequencing DNA from Maternal Blood", Proceedings of the National Academy of Sciences, 105(42):16266-16271.

Frock et al. (2015) "Genome-Wide Detection of DNA Double-Stranded Breaks Induced by Engineered Nucleases", Nature Biotechnology, 33:179-186.

Goodwin et al. (2016) "Coming of Age: Ten Years of Next-Generation Sequencing Technologies", Nature Reviews Genetics, 17:333-351.

Halazonetis et al. (2008) "An Oncogene-Induced DNA Damage Model for Cancer Development", Science, 319:1352-1355.

Harkins et al. (2020) "A Novel NGS Library Preparation Method to Characterize Native Termini of Fragmented DNA", Nucleic Acids Research, 48(8):13 pages.

Hashimoto et al. (2005) "Analysis of telomeric single-strand overhang length in human endometrial cancers" FEBS Letters, 579(13):2959-2964.

Homer et al. (2009) "BFAST: An Alignment Tool for Large Scale Genome Resequencing", PLoS ONE, 4(11):e7767:12 pages.

International Preliminary Report on Patentability dated Jan. 2019 in International Patent Application No. PCT/US2017/041974, filed on Jul. 13, 2017, 8 pages.

International Preliminary Report on Patentability Received dated Jul. 23, 2020 in PCT. Patent Application No. PCT/US2019/01321 0, filed on Jan. 11, 2019 and published as WO 2019/140201 on Jul. 18, 2019, 8 pages.

International Search Report and Written Opinion dated May 13, 2019 in International Patent Application No. PCT/US2019/01321 0, filed on Jan. 11, 2019, 11 pages.

International Search Report and Written Opinion dated Oct. 12, 2017 in International Patent Application No. PCT/US2017/041974, filed on Jul. 13, 2017, 11 pages.

Kang et al. (2016) "Comparative Analysis of Circulating Tumor DNA Stability in K3EDTA, Streck and CellSave Blood Collection Tubes", Clinical Biochemistry, 30 pages.

(56) References Cited

OTHER PUBLICATIONS

Karlin et al. (1993) "Applications and Statistics for Multiple High-Scoring Segments in Molecular Sequences", Proceedings of the National Academy of Sciences, 90:5873-5877.
Kent et al. (2002) "The Human Genome Browser at UCSC", Genome Research, 12:996-1006.
Kircher Martin (2012) "Analysis of High-Throughput Ancient DNA Sequencing Data", Methods in Molecular Biology, Chapter 23, 840:197-228.
Kivisild Toomas (2015) "Maternal Ancestry and Population History from Whole Mitochondrial Genomes", Investigative Genetics, 6(3):10 pages.
Knierim et al. (2011) "Systematic Comparison of Three Methods for Fragmentation of Long-Range PCR Products for Next Generation Sequencing", PLoS ONE, e28240, 6(11):6 pages.
Koohy et al. (2013) "Chromatin Accessibility Data Sets Show Bias Due to Sequence Specificity of the DNase I Enzyme", PLoS ONE, 8(7):9 pages.
Lahiri et al. (1993) "DNA Isolation by a Rapid Method from Human Blood Samples: Effects of MgCl2, EDTA, Storage Time, and Temperature on DNA Yield and Quality", Biochemical Genetics, 31(718):321-328.
Langmead et al. (2009) "Ultrafast and Memory-Efficient Alignment of Short DNA Sequences to the Human Genome", Genome Biology, Article R25, 10(3):10 pages.
Li et al. (2013) "Aligning sequence reads, clone sequences and assembly contigs with BWA-MEM", arXiv:1303, 3 pages.
Li et al. (2009) "Fast and Accurate Short Read Alignment with Burrows-Wheeler Transform", Bioinformatics, 25(14):1754-1760.
Li et al. (2009) "SOAP2: An Improved Ultrafast Tool for Short Read Alignment", Bioinformatics, 25(15):1966-1967.
Li et al. (2009) "The Sequence Alignment/Map format and SAMtools", Bioinformatics, 25(16):2078-2079.
Lieber et al. (2003) "Mechanism and Regulation of Human Non-Homologous DNA End-Joining", Nature Reviews Molecular Cell Biology vol. 4:712-720.
Metzker Michaell. (2010) "Sequencing Technologies—The Next Generation", Nature Review Genetics, 11(1):31-46.
Meyer et al. (2010) "Illumina Sequencing Library Preparation for Highly Multiplexed Target Capture and Sequencing", Cold Spring Harbor Protocols, 2010(6):20 pages.
Miller et al. (2008) "Sequencing the Nuclear Genome of the Extinct Woolly Mammoth", Nature, 456(7220):387-390.
Morey et al. (2013) "A Glimpse into Past, Present, and Future DNA Sequencing", Molecular Genetics and Metabolism, 110(1-2)3-24.
Oefner et al. (1996) "Efficient Random Subcloning of DNA Sheared in a Recirculating Point-Sink Flow System", Nucleic Acids Research, 24(20):3879-3886.
Patel et al. (2000) "Evaluation of Serum Alkaline DNase Activity in Treatment Monitoring of Head and Neck Cancer Patients", Tumor Biology, 21:82-89.
Poinar et al. (2006) "Metagenomics to Paleogenomics: Large-Scale Sequencing of Mammoth DNA", Science, 311:392-394.
Poptsova et al. (2014) "Non-Random DNA Fragmentation in Next-Generation Sequencing", Scientific Reports, 4:4532:6 pages.
Rasmussen et al. (2010) "Ancient Human Genome Sequence of an Extinct Palaeo-Eskimo", Nature, 463(7282):757-762.
Reuter et al. (2015) "High-Throughput Sequencing Technologies", Molecular Cell, 58:586-597.
Rivals et al. (2009) "MPSCAN: Fast Localisation of Multiple Reads in Genomes", WABI 2009: Algorithms in Bioinformatics, LNBI 5724, 246-260.
Rizk et al. (2010) "GASSST: Global Alignment Short Sequence Search Tool", Bioinformatics, 26(20):2534-2540.
Rushizky et al. (1960) "A Map of the Products Resulting from the Action of Micrococcal Nuclease on Thymus Deoxyribonucleic Acid and Its Use as a Guide to Specificity", Biochemical and Biophysical Research Communications, 2(3):153-158.
Sabo et al. (2006) "Genome-Scale Mapping of DNase I Sensitivity in Vivo Using Tiling DNA Microarrays", Nature Methods, 3(7):511-518.
Shinozuka et al. (2015) "A Simple Method for Semi-Random DNA Amplicon Fragmentation Using the Methylation-Dependent Restriction Enzyme MspJI", BMC Biotechnology, 15:25:13 pages.
Singh et al. (1988) "A Simple Technique for Quantitation of Low-Levels of DNA Damage in Individual Cells", Experimental Cell Research, 75:184-191.
Sosic et al. (2017) "Edlib: A C/C++ Library for Fast, Exact Sequence Alignment Using Edit Distance", Bioinformatics, 33(9):1394-1395.
Stiller et al. (2006) "Patterns of Nucleotide Misincorporations During Enzymatic Amplification and Direct Large-Scale Sequencing of Ancient DNA", Proceedings of the National Academy of Sciences, 103(37):13578-13584.
Sulkowski et al. (1962) "Mechanism of Action of Micrococcal Nuclease on Deoxyribonucleic Acid", Journal of Biological Chemistry, 237(8):2620-2625.
Tamkovich et al. (2006) "Circulating DNA and DNase Activity in Human Blood", Annals of the New York Academy of Sciences, 1075:191-196.
Tsai et al. (2015) "GUIDE-Seq Enables Genome-Wide Profiling of Off-Target Cleavage by CRISPR-Cas Nucleases", Nature Biotechnology, 33(2):187-197.
Wong et al. (2013) "Optimizing Blood Collection, Transport and Storage Conditions for cell free DNA Increases Access to Prenatal Diagnostic Testing", Clinical Biochemistry, 46:1099-1104.
Wylie (1980) "Glucocorticoid-Induced Thymocyte Apoptosis Is Associated with Endogenous Endonuclease Activation", Nature, 284:555-556.
Yan et al. (2017) "BLISS Is a Versatile and Quantitative Method for Genome-Wide Profiling of DNA Double-Strand Breaks", Nature Communications, 8:15058:9 pages.
Zhao et al. (2008) "Quantitative Telomeric Overhang Determination Using a Double-Strand Specific Nuclease", Nucleic Acids Research, 36(3):5 pages.
Daley and Wilson (2005) "Rejoining of DNA Double-Strand Breaks as a Function of Overhang Length†" Mol. and Cell. Biol., 25(3):896-906.
Didenko et al. (1998) "Biotin-Labeled Hairpin Oligonucleotides; Probes to Detect Double-Strand Breaks in DNA in Apoptotic Cells" Am. J. of Path., 152(4):897-902.
Didenko et al. (2003) "Early Necrotic DNA Degradation; Presence of Blunt-Ended DNA Breaks, 3' and 5' Overhangs in Apoptosis, but only 5' Overhangs in Early Necrosis" Am. J. of Path., 162(5):1571-1578.
Didenko (2011) "In Situ Labeling of DNA Breaks and Apoptosis by T7 DNA Polymerase" Methods Mol. Biol., 682:37-48.
Green (2017) "Forensic Identification from Mixed and Minute Samples" Funding Opportunity No. CFDA No. 16.560, University of California, Santa Cruz, 22pgs.
Harkins et al. (2017) "A new method for assessing postmortem DNA damage from ancient remains" American Association of Physical Anthropologists, Abstract, 1 pg.
Parkinson et al. (2012) "Preparation of High-quality next-generation sequencing libraries from picogram quantities of target DNA" Genome Research, 22(1):125-133.
Snyder et al. (2016) "Cell-free DNA Comprises an In Vivo Nucleosome Footprint that Informs Its Tissues-Of-Origin" Cell, 164:57-68.
Tamkovich et al. (2016) "Features of Circulating DNA Fragmentation in Blood of Healthy Females and Breast Cancer Patients" Advances in Experimental Medicine and Biology 924, pp. 47-51. DOI:10.1007/978-3-319-42044-8_10.
Wan et al. (2017) "Liquid biopsies come of age: towards implementation of circulating tumour DNA" Nature Reviews Cancer, 17:223-238.
Widlak et al. (2000) "Cleavage Preferences of the Apoptotic Endonuclease DFF40 (Caspase-activated DNase or Nuclease) on Naked DNA and Chromatin Substrates*" The J. of Biol. Chem., 275(11):8226-8232.
Cristiano et al. (2019) "Genome-wide cell-free DNA fragmentation in patients with cancer" Nature, 570:385-389.

(56) References Cited

OTHER PUBLICATIONS

Budowle and Van Daal (2008) "Forensically relevant SNP classes" Biotechniques, 44(5):603-608, 610.
Butler et al. (2003) "The development of reduced size STR amplicons as tools for analysis of degraded DNA" J Forensic Sci, 48(5):1054-1064.
Cahill et al. (2013) "Genomic evidence for island population conversion resolves conflicting theories of polar bear evolution" PLoS Genet, 9(3):e1003345.
Enari et al. (1998) "A caspase-activated DNase that degrades DNA during apoptosis, and its inhibitor ICAD" Nature, 391(6662):43-50.
Fischer et al. (2007) "DNase1L2 degrades nuclear DNA during corneocyte formation" J Invest Dermatol, 127(1):24-30.
Fischer et al. (2011) "Essential role of the keratinocyte-specific endonuclease DNase1L2 in the removal of nuclear DNA from hair and nails" J Invest Dermatol, 131(6):1208-1215.
Genomes Project et al. (2015) "A global reference for human genetic variation" Nature, 526(7571):68-74.
Gill et al. (2015) "Genotyping and interpretation of STR-DNA: Low-template, mixtures and database matches—Twenty years of research and development" Forensic Sci Int Genet, 18:100-117.
Green et al. (2008) "A complete Neandertal mitochondrial genome sequence determined by high-throughput sequencing" Cell, 134(3):416-426.
Green et al. (2009) "The Neandertal genome and ancient DNA authenticity" EMBO J, 28(17):2494-2502.
Green et al. (2010) "A draft sequence of the Neandertal genome" Science, 328(5979):710-722.
Jobling and Gill (2004) "Encoded evidence: DNA in forensic analysis" Nat Rev Genet, 5(10):739-751.
Kayser and De Knijff (2011) "Improving human forensics through advances in genetics, genomics and molecular biology" Nat Rev Genet, 12(3): 179-192.
Kivisild (2015) "Maternal ancestry and population history from whole mitochondrial genomes" Investig Genet, 6:3.
Krings et al. (1997) "Neandertal DNA sequences and the origin of modern humans" Cell, 90(1):19-30.
Mukae et al. (1998) "Molecular cloning and characterization of human caspase-activated DNase" Proc Natl Acad Sci U S A, 95(16):9123-918.
Mulero et al. (2008) "Development and validation of the AmpF ℓSTR® MiniFiler™ PCR Amplification Kit: a MiniSTR multiplex for the analysis of degraded and/or PCR inhibited DNA" J Forensic Sci, 53(4):838-852.
Prufer et al. (2010) "Computational challenges in the analysis of ancient DNA" Genome Biol, 11(5):R47.
Schweizer et al. (2016) "Targeted capture and resequencing of 1040 genes reveal environmentally driven functional variation in grey wolves" Mol Ecol, 25(1):357-379.
Shapiro and Hofreiter (2014) "A paleogenomic perspective on evolution and gene function: new insights from ancient DNA" Science, 343(6169):1236573.
Szabo et al. (2012) "In situ labeling of DNA reveals interindividual variation in nuclear DNA breakdown in hair and may be useful to predict success of forensic genotyping of hair" Int J Legal Med, 126(1):63-70.
Thalmann et al. (2013) "Complete mitochondrial genomes of ancient canids suggest a European origin of domestic dogs" Science, 342(6160):871-874.
Van Oorschot et al. (2010) "Forensic trace DNA: a review" Investig Genet, 1(1):14.
Van Oven and Kayser (2009) "Updated comprehensive phylogenetic tree of global human mitochondrial DNA variation" Hum Mutat, 30(2):E386-394.
Vohr et al. (2015) "A method for positive forensic identification of samples from extremely low-coverage sequence data" BMC Genomics, 16:1034.
Vohr et al. (2017) "A phylogenetic approach for haplotype analysis of sequence data from complex mitochondrial mixtures" Forensic Sci Int Genet, 30:93-105.
Monson-Miller et al. (2012) "Reference Genome-Independent Assessment of Mutation Density Using Restriction Enzyme-Phased Sequencing", BMC Genomics, 13(72):15 pages.
Office Action dated Sep. 1, 2021 in U.S. Appl. No. 16/961,113, filed Jul. 9, 2020, 13 pages.
Shiroguchi et al. (2012) "Digital RNA Sequencing Minimizes Sequence-Dependent Bias and Amplification Noise with Optimized Single-Molecule Barcodes", Proceedings of the National Academy of Sciences, 109(4):1347-1352.

\* cited by examiner

FIG. 8
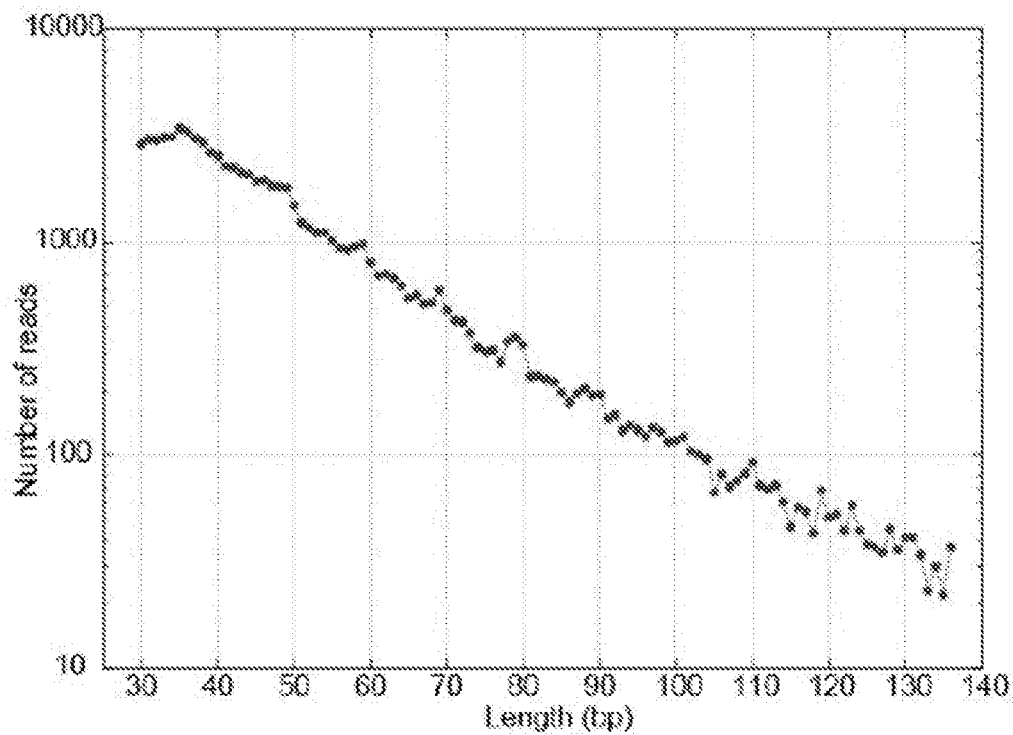
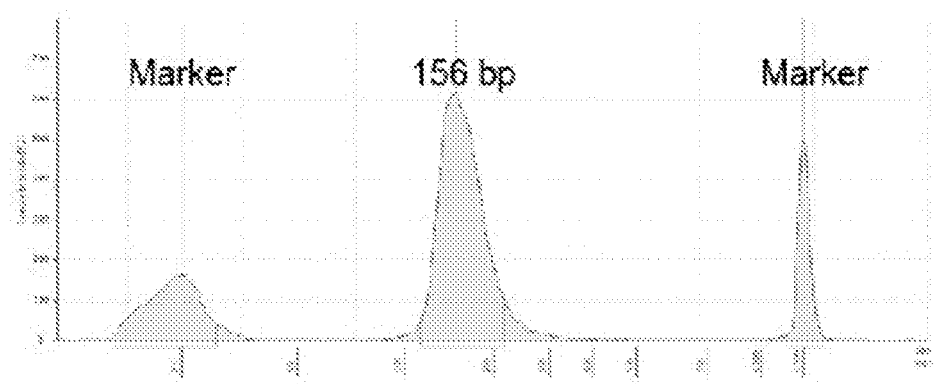

METHODS OF PRODUCING NUCLEIC ACID LIBRARIES

RELATED PATENT APPLICATIONS

This patent application claims the benefit of U.S. Provisional Patent Application No. 62/362,904 filed on Jul. 15, 2016, entitled Methods of Producing Nucleic Acid Libraries, naming Richard E. Green as first named inventor. The entire content of the foregoing application is incorporated herein by reference, including all text, tables and drawings.

STATEMENT REGARDING FEDERALLY SPONSORED RESEARCH

This invention was made with Government support under contract number 1513501 awarded by the National Science Foundation. The Government has certain rights in the invention.

INTRODUCTION

Recent advances in DNA sequencing have revolutionized the field of genomics, making it possible for even single research groups to generate large amounts of sequence data very rapidly and at a substantially lower cost. These high-throughput sequencing technologies make deep transcriptome sequencing and transcript quantification, whole genome sequencing and resequencing available to many more researchers and projects.

A variety of commercial high-throughput sequencing platforms exist and are described, e.g., in Metzker, M. L. (2010) *Nat. Rev. Genet.* 11:31-46, Morey et al. (2013) *Mol. Genet. Metab.* 110: 3-24, Reuter et al. (2015) *Molecular Cell* 58(4):586-597, and elsewhere. In the Illumina platform, the sequencing process involves clonal amplification of adaptor-ligated DNA fragments on the surface of a glass slide. Bases are read using a cyclic reversible termination strategy, which sequences the template strand one nucleotide at a time through progressive rounds of base incorporation, washing, imaging, and cleavage. In this strategy, fluorescently labeled 3'-O-azidomethyl-dNTPs are used to pause the polymerization reaction, enabling removal of unincorporated bases and fluorescent imaging to determine the added nucleotide. Following scanning of the flow cell with a coupled-charge device (CCD) camera, the fluorescent moiety and the 3' block are removed, and the process is repeated.

An emerging single-molecule strategy that has made significant progress in recent years is nanopore-based sequencing, with Oxford Nanopore Technologies leading the development and commercialization of this method. Nanopore sequencing principally relies on the transition of DNA or individual nucleotides through a small channel. A sequencing flow cell includes hundreds of independent micro-wells, each containing a synthetic bilayer perforated by biologic nanopores. Sequencing is accomplished by measuring characteristic changes in current that are induced as the bases are threaded through the pore by a molecular motor protein. Library preparation is minimal, involving fragmentation of DNA and ligation of adapters, and can be done with or without PCR amplification. The library design allows sequencing of both strands of DNA from a single molecule, which increases accuracy.

The selection of an appropriate sequencing platform for particular types of experiments is an important consideration, and requires a detailed understanding of the technologies available, including sources of error, error rate, as well as the speed and cost of sequencing. While sequencing costs have drastically decreased, the throughput and costs of library preparation are now a limiting factor.

SUMMARY

Provided are methods of producing nucleic acid libraries. In certain aspects, the methods include combining target nucleic acids and an oligonucleotide pool. Each oligonucleotide of the oligonucleotide pool may include (i) a complementarity region capable of hybridizing to an overhang in a target nucleic acid, and (ii) a complementarity region identification polynucleotide. Oligonucleotides in the pool may include complementarity regions of different lengths, and the complementarity region identification polynucleotide may be specific to the length of the complementarity region (and may be specific to other features of the complementarity region). In such aspects, the combining is under conditions in which complementarity regions in the oligonucleotides hybridize to overhangs in the target nucleic acids having a corresponding length, thereby forming hybridization products (e.g., for a nucleic acid library).

In certain aspects, the methods include combining 5' phosphorylated nucleic acids and an oligonucleotide pool. Oligonucleotides of the oligonucleotide pool may include complementarity regions of varying length and nucleotide sequence, and a complementarity region identification sequence. In such aspects, the combining is under conditions in which oligonucleotides of the oligonucleotide pool hybridize to nucleic acids of the 5' phosphorylated nucleic acids having overhang regions that are complementary in sequence and have corresponding lengths with respect to the complementarity regions of the oligonucleotides. Compositions and kits that find use, e.g., in practicing the methods of the present disclosure are also provided.

BRIEF DESCRIPTION OF THE FIGURES

FIG. 8 shows length of DNA fragments recovered from hair shafts. Top panel: DNA fragments recovered from a 140 year old rootless hair extract were mapped to the human genome. Nearly all fragments were less than 50 bp long. Bottom panel: Tapestation trace of length of sequencing library from DNA extracted from fresh hair. This length included sequencing adapters of about 110 bp. Therefore, even in fresh hair, most DNA fragments were less than 50 bp long.

DETAILED DESCRIPTION

Figure 1:
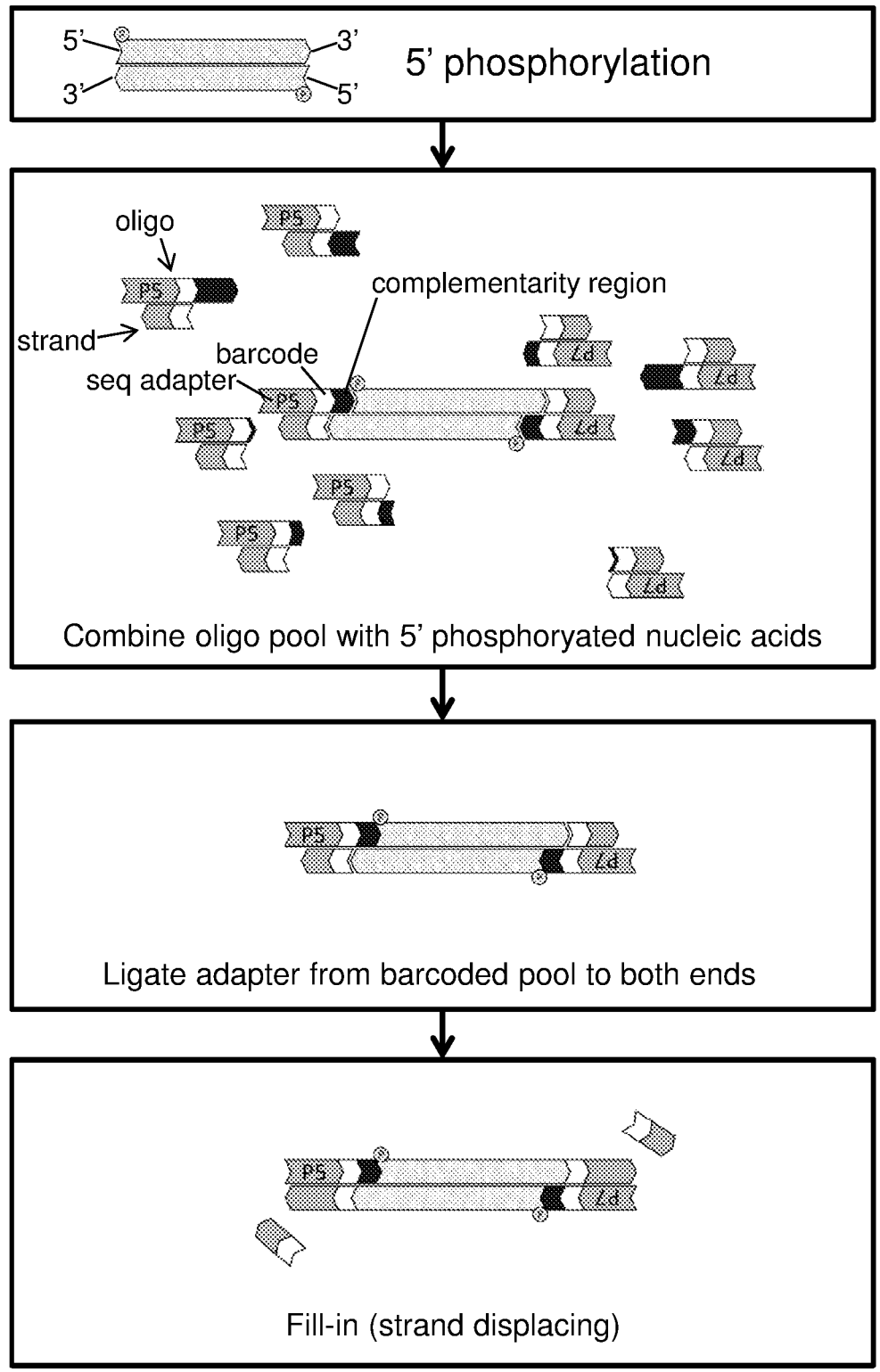
FIG. 1 schematically illustrates a method of producing a nucleic acid library according to one embodiment of the present disclosure.

Provided are methods of producing nucleic acid libraries. In certain aspects, the methods include combining target nucleic acids and an oligonucleotide pool. Each oligonucleotide of the oligonucleotide pool may include (i) a complementarity region capable of hybridizing to an overhang in a target nucleic acid, and (ii) a complementarity region identification polynucleotide. Oligonucleotides in the pool may include complementarity regions of different lengths, and the complementarity region identification polynucleotide may be specific to the length of the complementarity region (and may be specific to other features of the complementarity region). In such aspects, the combining is under conditions in which complementarity regions in the oligonucleotides hybridize to overhangs in the target nucleic acids having a corresponding length, thereby forming hybridization products (e.g., for a nucleic acid library).

In certain aspects, the methods include combining 5' phosphorylated nucleic acids and an oligonucleotide pool. Oligonucleotides of the oligonucleotide pool may include complementarity regions of varying length and nucleotide sequence, and a complementarity region identification sequence. In such aspects, the combining is under conditions in which oligonucleotides of the oligonucleotide pool hybridize to nucleic acids of the 5' phosphorylated nucleic acids having overhang regions that are complementary in sequence and have corresponding lengths with respect to the complementarity regions of the oligonucleotides. Compositions and kits that find use, e.g., in practicing the methods of the present disclosure are also provided.

Before the methods, compositions and kits of the present disclosure are described in greater detail, it is to be understood that the methods, compositions and kits are not limited to particular embodiments described, as such may, of course, vary. It is also to be understood that the terminology used herein is for the purpose of describing particular embodiments only, and is not intended to be limiting, since the scope of the methods, compositions and kits will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods, compositions and kits. The upper and lower limits of these smaller ranges may independently be included in the smaller ranges and are also encompassed within the methods, compositions and kits, subject to any specifically excluded limit in the stated range. Where the stated range includes one or both of the limits, ranges excluding either or both of those included limits are also included in the methods, compositions and kits.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods, compositions and kits belong. Although any methods, compositions and kits similar or equivalent to those described herein can also be used in the practice or testing of the methods, compositions and kits, representative illustrative methods, compositions and kits are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present methods, compositions and kits are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, compositions and kits, which are, for clarity, described in the context of separate embodiments, may also be provided in combination in a single embodiment. Conversely, various features of the methods, compositions and kits, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present methods, compositions and kits and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Methods

As summarized above, aspects of the present disclosure include methods of producing nucleic acid libraries. In some embodiments, the methods include combining a nucleic acid composition comprising target nucleic acids that comprise an overhang and an oligonucleotide pool comprising oligonucleotides, where some or all of the oligonucleotides comprises (i) a complementarity region capable of hybridizing to an overhang in a target nucleic acid, and (ii) a complementarity region identification polynucleotide; oligonucleotides in the pool include complementarity regions of different lengths; and the complementarity region identification polynucleotide is specific to one or more features of the complementarity region (e.g., length). In such aspects, the combining is under conditions in which complementarity regions in the oligonucleotides hybridize to overhangs in the target nucleic acids having a corresponding length, thereby forming hybridization products (e.g., for a nucleic acid library).

In some embodiments, the methods include combining 5' phosphorylated nucleic acids and an oligonucleotide pool including oligonucleotides that include complementarity regions of varying length and nucleotide sequence, and a complementarity region identification sequence. In such aspects, the combining is under conditions in which oligonucleotides of the oligonucleotide pool hybridize to nucleic acids of the 5' phosphorylated nucleic acids having overhang regions that are complementary in sequence and have corresponding lengths with respect to the complementarity regions of the oligonucleotides. Such hybridized oligonucleotides and nucleic acids may be referred to herein as "hybridization products." Aspects of the subject methods will now be described in greater detail.

In some embodiments, the methods further include, prior to the combining step, producing the 5' phosphorylated nucleic acids by phosphorylating the 5' ends of nucleic acids from a nucleic acid sample. Reagents and kits for carrying out 5' phosphorylation of nucleic acids are known and available. For example, nucleic acids can be treated with a polynucleotide kinase (PNK) (e.g., T4 PNK), which catalyzes the transfer and exchange of Pi from the γ position of ATP to the 5'-hydroxyl terminus of polynucleotides (double- and single-stranded DNA and RNA) and nucleoside 3'-monophosphates. Suitable reaction conditions include, e.g., incubation of the nucleic acids with PNK in 1×PNK reaction buffer (e.g., 70 mM Tris-HCl, 10 mM MgCl2, 5 mM DTT, pH 7.6 @ 25° C.) for 30 minutes at 37° C. Optionally, following the phosphorylation reaction, the PNK may be heat inactivated, e.g., at 65° C. for 20 minutes. In some embodiments, the methods do not include, prior to the combining step, producing the 5' phosphorylated nucleic acids by phosphorylating the 5' ends of nucleic acids from a nucleic acid sample. In such instances, a nucleic acid sample comprises nucleic acids with natively phosphorylated 5' ends.

In some embodiments, target nucleic acids are not modified in length prior to combining with the pool. In this context, "not modified" means that target nucleic acids are isolated from a sample (e.g., a sample containing nucleic acid isolated from a living or deceased organism) and then combined with the oligonucleotide pool without modifying the length of the target nucleic acids. For example, the target nucleic acids are not shortened (e.g., they are not contacted with a restriction enzyme or nuclease or physical condition that reduces length (e.g., shearing condition, cleavage condition)) and are not increased in length by one or more nucleotides (e.g., ends are not filled in at overhangs; no nucleotides are added to the ends). Adding a phosphate or chemically reactive group to one or both ends of a target nucleic acid is not considered modifying the length of the nucleic acid.

In certain aspects, the methods of the present disclosure include, subsequent to the combining step, exposing the hybridization products to conditions under which an end of the target nucleic acid is joined to an end of the oligonucleotide to which it is hybridized. Joining may be achieved by any suitable approach that permits covalent attachment of the target nucleic acid to the oligonucleotide to which it is hybridized. When one end of a target nucleic acid is joined to an end of the oligonucleotide to which it is hybridized, typically two attachment events are conducted: 1) the 3' end of one strand in the target nucleic acid to the 5' end of one strand in the oligonucleotide, and 2) the 5' end of the other strand in the target nucleic acid to the 3' end of the other strand in the oligonucleotide. When both ends of a target nucleic acid are each joined to an oligonucleotide to which it is hybridized, typically four attachment events are conducted: 1) the 3' end of one strand in the target nucleic acid to the 5' end of one strand in the oligonucleotide, 2) the 5' end of the other strand in the target nucleic acid to the 3' end of the other strand in the oligonucleotide; and 3) and 4): the same as (1) and (2) for the opposite end of the target nucleic acid attached to another oligonucleotide.

In certain aspects, the methods of the present disclosure include, subsequent to the combining step, contacting the hybridization products with an agent comprising a ligase activity under conditions in which an end of a target nucleic acid is covalently linked to an end of the oligonucleotide to which the target nucleic acid is hybridized. In some embodiments, the hybridization products are contacted with a first agent comprising a first ligase activity and a second agent comprising a second ligase activity different than the first ligase activity. For example, the first ligase activity and the second ligase activity independently may be chosen from blunt-end ligase activity, nick-sealing ligase activity, sticky end ligase activity, circularization ligase activity, and cohesive end ligase activity.

In certain aspects, the methods of the present disclosure include joining target nucleic acids to oligonucleotides via biocompatible attachments. Methods may include, for example, "click" chemistry or tagging, which include biocompatible reactions useful for joining biomolecules. In some embodiments, an end of each of the oligonucleotides comprises a first chemically reactive moiety and an end of each of the target nucleic acids includes a second chemically reactive moiety. In such embodiments, the first chemically reactive moiety typically is capable of reacting with the second chemically reactive moiety and forming a covalent bond between an oligonucleotide and a target nucleic acid to which the oligonucleotide is hybridized. In certain aspects, the methods of the present disclosure include, prior to combining the nucleic acid composition with the oligonucleotide pool, contacting the target nucleic acids in the composition with one or more chemical agents under conditions in which the second chemically reactive moiety is incorporated at an end of each of the target nucleic acids. In certain aspects, the methods of the present disclosure include, subsequent to the combining step, exposing the hybridization products with one or more chemical agents to conditions in which the first chemically reactive moiety reacts with the second chemically reactive moiety forming a covalent bond between an oligonucleotide and a target nucleic acid to which the oligonucleotide is hybridized. In some embodiments, the first chemically reactive moiety is capable of reacting with the second chemically reactive moiety to form a 1,2,3-triazole between the oligonucleotide and the target nucleic acid to which the oligonucleotide is hybridized. In some embodiments, the first chemically reactive moiety is capable of reacting with the second chemically reactive moiety under conditions comprising copper. The first and second chemically reactive moieties may include any suitable pairings. For example, the first chemically reactive moiety may be chosen from an azide-containing moiety and 5-octadiynyl deoxyuracil, and the second chemically reactive moiety may be independently chosen from an azide-containing moiety, hexynyl and 5-octadiynyl deoxyuracil. In some embodiments, the azide-containing moiety is N-hydroxysuccinimide (NHS) ester-azide.

In certain aspects, the methods of the present disclosure include, subsequent to the combining step, ligating the hybridized oligonucleotides and nucleic acids. When included, such a ligation step includes ligating the 5' phosphorylated ends of the nucleic acids to the 3' ends of the oligonucleotides hybridized thereto. Suitable reagents (e.g., ligases) and kits for performing such ligation reactions are known and available, e.g., the Instant Sticky-end Ligase Master Mix available from New England Biolabs (Ipswich, Mass.). Ligases that may be employed include, e.g., T4 DNA ligase (e.g., at low or high concentration), T4 DNA ligase, T7 DNA Ligase, *E. coli* DNA Ligase, Electro Ligase®, or the like. Conditions suitable for performing the ligation reaction will vary depending upon the type of ligase used. Information regarding such conditions is readily available. According to certain embodiments, during the combining step, the oligonucleotides of the oligonucleotide pool are present as duplexes. That is, oligonucleotides of the oligonucleotide pool may be hybridized to a nucleic acid strand other than a nucleic acid strand of the target nucleic acids (e.g., 5' phosphorylated nucleic acids). In certain aspects, the duplexes include the oligonucleotides and nucleic acid strands hybridized to a region of the oligonucleotides adjacent (e.g., immediately adjacent) to the complementarity region. In some embodiments, the region of the oligonucleotides adjacent to the complementarity region includes all or a portion of the complementarity region identification polynucleotide (complementarity region identification sequence).

In certain embodiments, the oligonucleotide pool comprises oligonucleotides comprising a first strand and a second strand. In certain embodiments, the oligonucleotide pool comprises oligonucleotides each consisting essentially of a first strand and a second strand. Consisting essentially of a first strand and a second strand means that the oligonucleotides do not include any additional strands of nucleic acid (e.g., hybridized to the oligonucleotides). Thus, "consisting essentially of" here refers to the number of strands in the oligonucleotides, and the oligonucleotides can include other features not essential to the number of strands (e.g., can include a detectable label, can include other regions). A first strand may comprise a first polynucleotide and a second strand comprises a second polynucleotide complementary to the first polynucleotide.

In certain aspects, when the oligonucleotides of the oligonucleotide pool are present as duplexes, some or all of the duplexes may include an overhang at the end of the duplex opposite the end that hybridizes to the nucleic acids. When such duplex overhangs exist, subsequent to the combining, the methods of the present disclosure may further include filling in the overhangs formed by the duplexes. Reagents and kits for carrying out such fill-in reactions are known and available. Polymerases suitable for performing fill-in reactions include, e.g., DNA polymerase I, large (Klenow) fragment, *Bacillus stearothermophilus* (Bst) DNA polymerase, and the like. Conditions suitable for performing the fill-in reaction will vary, e.g., depending upon the type of polymerase used, which reaction condition information is readily available.

In certain aspects, methods herein may be performed using hairpin adapters. Hairpin adapters generally comprise a double-stranded "stem" region and a single stranded "loop" region. In some embodiments, the oligonucleotides comprise one strand (i.e., one continuous strand) capable of adopting a hairpin structure. In some embodiments, the oligonucleotides consist essentially of one strand (i.e., one continuous strand) capable of adopting a hairpin structure. Consisting essentially of one strand means that the oligonucleotides do not include any additional strands of nucleic acid (e.g., hybridized to the oligonucleotides) that are not part of the continuous strand. Thus, "consisting essentially of" here refers to the number of strands in the oligonucleotides, and the oligonucleotides can include other features not essential to the number of strands (e.g., can include a detectable label, can include other regions). Oligonucleotides comprising or consisting essentially of one strand capable of forming a hairpin structure may be referred to herein as hairpin adapters.

Hairpin adapters may comprise a plurality of polypeptides within the one strand. In some embodiments, hairpin adapters comprise a first polynucleotide and a second polynucleotide. In some embodiments, a first polynucleotide is complementary to a second polynucleotide. In some embodiments, a portion of a first polynucleotide is complementary to a portion of a second polynucleotide. In some embodiments, a first polynucleotide comprises a first region that is complementary to a first region in a second polynucleotide, and the first polynucleotide comprises a second region that is not complementary to a second region in the second polynucleotide. The complementary region often forms the stem of the hairpin adapter and the non-complementary region often forms the loop, or part thereof, of the hairpin adapter. The first and second polypeptides may comprise components of adapters as described herein, such as, for example, amplification priming sites and specific sequencing adapters (e.g., P5, P7 adapters).

Hairpin adapters may comprise one or more cleavage sites capable of being cleaved under cleavage conditions. In some embodiments, a cleavage site is located between a first and second polynucleotide. Cleavage at a cleavage site often generates two separate strands from the hairpin adapter. In some embodiments, cleavage at a cleavage site generates a partially double stranded adapter with two unpaired strands forming a "Y" structure. Cleavage sites may comprise, for example, uracil and/or deoxyuridine bases. Cleavage sites comprising uracil and/or deoxyuridine may be cleaved, for example, using DNA glycosylase, endonuclease, RNAse, and the like and combinations thereof. In some embodiments, cleavage sites comprise a diol. For example, cleavage sites may comprise vicinal diol incorporated in a 5' to 5' linkage. Cleavage sites comprising a diol may be chemically cleaved, for example, using a periodate. In some embodiments, cleavage sites comprise a restriction enzyme recognition site. In some embodiments, cleavage sites comprise a rare-cutter restriction enzyme recognition site (e.g., a NotI recognition sequence). A rare-cutter restriction enzyme recognition site generally occurs with a low frequency in DNA/RNA from mammals and other organisms. For example, a rare-cutter restriction enzyme recognition site may include sequences rarely found in human or mammalian genomic sequences. Cleavage sites comprising a restriction enzyme recognition site or a rare-cutter restriction enzyme recognition site may be cleaved by a restriction enzyme or a rare-cutter restriction enzyme (e.g., NotI). In some embodiments, a method herein comprises after combining a pool of hairpin oligonucleotides with target nucleic acids, exposing one or more cleavage sites to cleavage conditions, thereby cleaving the oligonucleotides. In some embodiments, cleavage sites comprise a blunt end restriction enzyme recognition site. Cleavage sites comprising a blunt end restriction enzyme recognition site may be cleaved by a blunt end restriction enzyme.

In some embodiments, a hairpin adapter comprises an overhang region (e.g., 5' overhang, 3' overhang). The overhang region of a hairpin adapter typically is located adjacent to the double-stranded "stem" portion and at the opposite end of the "loop" portion. The overhang region of a hairpin adapter herein typically comprises a complementarity region described herein. Hairpin adapters herein comprising a complementarity region often also comprise a complementarity region identification polynucleotide (e.g., an identification polynucleotide specific to the length of the complementarity region, and sometimes specific to the type (5' or 3') and/or sequence of the complementarity region). In some embodiments, a hairpin adapter comprises in a 5' to 3' orientation: a first complementarity region identification polynucleotide, a first polynucleotide, one or more cleavage sites, a second polynucleotide, a second complementarity region identification polynucleotide complementary to the first complementarity region identification polynucleotide, and a complementarity region. In some embodiments, a hairpin adapter comprises in a 5' to 3' orientation: a complementarity region, a first complementarity region identification polynucleotide, a first polynucleotide, one or more cleavage sites, a second polynucleotide, and a second complementarity region identification polynucleotide complementary to the first complementarity region identification polynucleotide. In some embodiments, a pool of hairpin adapters comprises a mixture of: 1) oligonucleotides comprising in a 5' to 3' orientation: a first complementarity region identification polynucleotide, a first polynucleotide, one or more cleavage sites, a second polynucleotide, a second complementarity region identification polynucleotide complementary to the first complementarity region identification polynucleotide, and a complementarity region; and 2) oligonucleotides comprising in a 5' to 3' orientation: a complementarity region, a first complementarity region identification polynucleotide, a first polynucleotide, one or more cleavage sites, a second polynucleotide, and a second complementarity region identification polynucleotide complementary to the first complementarity region identification polynucleotide. In certain embodiments of the above, the first and second polynucleotides are ordered in a 5' to 3' orientation as follows: first portion of first polynucleotide, second portion of first polynucleotide, cleavage site, second portion of second polynucleotide and first portion of second polynucleotide, where the first portions of each polynucleotide are complementary and the second portions of each polynucleotide are not complementary.

In certain aspects, methods herein may be performed using immobilized adapters. In such method, a first set of single stranded oligonucleotides (e.g., single stranded barcoded variable complementarity region adapters) are immobilized to a solid phase. Then the complement oligonucleotide strands are hybridized to form double-stranded immobilized oligonucleotides. Double stranded target nucleic acids are joined (e.g., ligated) to the immobilized oligonucleotides. The free end of the target nucleic acids are then joined (e.g., ligated) to a second set of oligonucleotides. Single stranded oligonucleotides may be immobilized to a solid phase according to any suitable method for attaching nucleic acid to a solid phase. Methods may include utilizing members of a binding pair such as, for example, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group, and the like.

As noted above, the complementarity regions of oligonucleotides of the oligonucleotide pool have varying lengths and nucleotide sequences. The complementarity regions may be designed to be suitable to interrogate/detect the length, identity, or both, of 5' and/or 3' overhangs present in the target nucleic acids (e.g., 5' phosphorylated nucleic acids). The complementarity regions may be designed, for example, based on the type of nucleic acid sample from which the 5' phosphorylated nucleic acids were produced and/or from which the target nucleic acids were obtained. In certain aspects, the nucleotide sequences of the complementarity regions are random nucleotide sequences across the length of the complementarity regions, e.g., such that the pool of oligonucleotides includes oligonucleotides having complementarity regions complementary to any possible overhang sequences suspected of being present in the target nucleic acids (e.g., 5' phosphorylated nucleic acids). In some embodiments, the oligonucleotide pool comprises oligonucleotides that comprise all possible overhang polynucleotide combinations for a particular overhang length. All possible overhang polynucleotide combinations for a particular overhang length means that each position can be A, G, C or T throughout the length of the overhang. For example, a three nucleotide overhang has $4^3$ possible polynucleotide sequence arrangements (64 possible polynucleotides) when each position could be A, G, C or T. In some embodiments, the oligonucleotide pool comprises oligonucleotides that comprise all possible overhang polynucleotide combinations for each overhang length. For example, an oligonucleotide pool comprising oligonucleotides with overhang lengths between 1 and 10 bases long may comprise the following total number of possible overhang sequences: $4+4^2+4^3+4^4+4^5+4^6+4^7+4^8+4^9+4^{10}$.

In other aspects, the nucleotide sequence(s) of the complementarity regions may be specifically designed to interrogate/detect one or more subsets of 5' and/or 3' overhang sequences of interest present in the target nucleic acids (e.g., 5' phosphorylated nucleic acids), e.g., where the interrogation/detection of such one or more subsets is informative for purposes of diagnosing a medical condition, identifying the source of the nucleic acid sample from which the 5' phosphorylated nucleic acids were produced, and/or from which the target nucleic acids were obtained, and/or the like.

The complementarity regions of oligonucleotides of the oligonucleotide pool may be of any suitable length, which suitable length may vary, e.g., based on the source of the nucleic acid sample from which the 5' phosphorylated nucleic acids were produced and/or from which the target nucleic acids were obtained. For example, the lengths of the complementarity regions may be designed to represent/correspond to the lengths of any possible overhangs suspected of being present in the target nucleic acids (e.g., 5' phosphorylated nucleic acids). In certain embodiments, the lengths of the complementarity regions may be specifically designed to interrogate/detect one or more subsets of 5' and/or 3' overhangs of interest present in the target nucleic acids (e.g., 5' phosphorylated nucleic acids), e.g., where the interrogation/detection of such one or more subsets is informative for purposes of diagnosing a medical condition, identifying the source of the nucleic acid sample from which the 5' phosphorylated nucleic acids were produced, and/or from which the target nucleic acids were obtained, and/or the like. In certain embodiments, the lengths of the complementarity regions may be designed to enrich for a subset of DNA fragments from a sample by providing ligation partners for only that subset.

In certain aspects, the oligonucleotide pool includes oligonucleotides having varying complementarity regions from 1 to 50 nucleotides in length, such as from 1 to 40, 1 to 30, 1 to 20, 1 to 15, 1 to 14, 1 to 13, 1 to 12, 1 to 11, 1 to 10, 1 to 9, 1 to 8, 1 to 7, 1 to 6, 1 to 5, 1 to 4, 1 to 3, or 1 to 2 nucleotides in length. According to some embodiments, the oligonucleotide pool includes oligonucleotides having varying complementarity region lengths of 50 nucleotides or less, 40 nucleotides or less, 30 nucleotides or less, 20 nucleotides or less, 19 nucleotides or less, 18 nucleotides or less, 17 nucleotides or less, 16 nucleotides or less, 15 nucleotides or less, 14 nucleotides or less, 13 nucleotides or less, 12 nucleotides or less, 11 nucleotides or less, 10 nucleotides or less, 9 nucleotides or less, 8 nucleotides or less, 7 nucleotides or less, 6 nucleotides or less, 5 nucleotides or less, 4 nucleotides or less, 3 nucleotides or less, or 2 nucleotides or less. In certain aspects, the oligonucleotide pool includes oligonucleotides having varying complementarity region lengths of 2 nucleotides or more, such as 3 nucleotides or more, 4 nucleotides or more, 5 nucleotides or more, 6 nucleotides or more, 7 nucleotides or more, 8 nucleotides or more, 9 nucleotides or more, 10 nucleotides or more, 11 nucleotides or more, 12 nucleotides or more, 13 nucleotides or more, 14 nucleotides or more, 15 nucleotides or more, 16 nucleotides or more, 17 nucleotides or more, 18 nucleotides or more, 19 nucleotides or more, 20 nucleotides or more, 30 nucleotides or more, 40 nucleotides or more, or 50 nucleotides or more.

In some embodiments, certain oligonucleotides of the oligonucleotide pool have no complementarity region. Such oligonucleotides may be blunt ended and may be capable of being joined (e.g., ligated) to one or more blunt ends of a target nuclei acid. Oligonucleotides having no complementarity region may be referred to as having a complementarity region with a length of zero nucleotides.

The complementarity region identification sequence (e.g., barcode) of the oligonucleotides of the oligonucleotide pool uniquely identifies the complementarity region present in its respective oligonucleotide, and in turn, uniquely identifies each type of overhang (e.g., length, 5' or 3', and/or the like) present in the target nucleic acids (e.g., 5' phosphorylated nucleic acids) to which the complementarity regions specifically hybridize. Often, complementarity region identification polynucleotides specific to complementarity regions that hybridize to overhangs of different lengths are different from one another and are unique. Typically, complementarity region identification polynucleotides specific to i) complementarity regions that hybridize to overhangs of different lengths; and ii) complementarity regions of different type (i.e., 3', 5'), are different from one another and are unique. Generally, no two complementarity region identification sequences "specific to the length of the complementarity region" are in oligonucleotides of a pool that have overhangs of a different length. In other words, a given complementarity region identification sequence (or set of sequences) that is specific to a given length of a complementarity region will only be present in oligonucleotides having complementarity regions (overhangs) of such given length. Oligonucleotides having a different length of complementarity region will include a different complementarity region identification sequence (or set of sequences). In some embodiments, there is one complementarity region identification sequence for all oligonucleotides in the pool having an overhang of a specific length. In some embodiments, there are two complementarity region identification sequences for all oligonucleotides in the pool having an overhang of a specific length such that one complementarity region identification sequence is specific to the given length for 5' overhangs and the other complementarity region identification sequence is specific to the given length for 3' overhangs. In some embodiments, there is one or two complementarity region identification sequence(s) for all oligonucleotides in the pool having an overhang of a specific length, irrespective of the sequence of the overhang. In some embodiments, there is a subset of complementarity region identification sequences for oligonucleotides in the pool having an overhang of a specific length, where different complementarity region identification sequences in the subset are specific to different complementarity region sequences in the oligonucleotides (e.g., in addition to being specific to the length and type (i.e., 5' or 3') of complementarity region). The terms "complementarity region identification sequence," "complementarity region identification polynucleotide," "identification polynucleotide," "variable overhang barcode," "variable complementarity region barcode," and "barcode" may be used interchangeably herein.

A polynucleotide herein may be a portion of a larger polynucleotide. The larger polynucleotide may be an oligonucleotide. For example, a complementarity region identification polynucleotide may be considered a region or a domain of an oligonucleotide herein. Accordingly, a complementarity region identification polynucleotide may be referred to as a complementarity region identification region or a complementarity region identification domain. Two or more polynucleotides (e.g., first and second polynucleotides) may each be portions of the same larger polynucleotide, where the same larger polynucleotide may be, e.g., the same oligonucleotide. Such two or more polynucleotides may be referred to as regions or domains of the larger polynucleotide, e.g., first and second regions of an oligonucleotide herein or first and second domains of an oligonucleotide herein.

By way of example and for illustrative purposes only, the oligonucleotide pool may include: a first subset of oligonucleotides that include a complementarity region identification sequence that uniquely identifies a complementarity region that specifically hybridizes to 5' overhangs of 1 nucleotide in length; a second subset of oligonucleotides that include a complementarity region identification sequence that uniquely identifies a complementarity region that specifically hybridizes to 5' overhangs of 2 nucleotides in length; a third subset of oligonucleotides that include a complementarity region identification sequence that uniquely identifies a complementarity region that specifically hybridizes to 5' overhangs of 3 nucleotides in length; a fourth subset of oligonucleotides that include a complementarity region identification sequence that uniquely identifies a complementarity region that specifically hybridizes to 5' overhangs of 4 nucleotides in length; a fifth subset of oligonucleotides that include a complementarity region identification sequence that uniquely identifies a complementarity region that specifically hybridizes to 3' overhangs of 1 nucleotide in length; a sixth subset of oligonucleotides that include a complementarity region identification sequence that uniquely identifies a complementarity region that specifically hybridizes to 3' overhangs of 2 nucleotides in length; a seventh subset of oligonucleotides that include a complementarity region identification sequence that uniquely identifies a complementarity region that specifically hybridizes to 3' overhangs of 3 nucleotides in length; an eighth subset of oligonucleotides that include a complementarity region identification sequence that uniquely identifies a complementarity region that specifically hybridizes to 3' overhangs of 4 nucleotides in length; and so forth as desired.

The complementarity region identification sequence (e.g., barcode) may be any suitable length, e.g., so as to provide for a sufficient number of unique complementarity region identification sequences representative of the various different complementarity regions present in the oligonucleotide pool. In certain aspects, the complementarity region identification sequence is from 2 to 10 nucleotides in length, e.g., from 3 to 9, from 3 to 8, from 3 to 7, from 3 to 6, or from 3 to 5 (e.g., 5) nucleotides in length.

Any of the oligonucleotide pools described herein may further include oligonucleotides that do not have complementarity regions, which oligonucleotides may include an identification sequence specific to oligonucleotides that do not have complementarity regions. Oligonucleotides that do not include a complementarity region find use, e.g., in detecting/interrogating nucleic acids of the target nucleic acids (e.g., 5' phosphorylated nucleic acids) having blunt ends (that is, no overhangs).

The oligonucleotides of the oligonucleotide pool may include natural nucleotides, non-natural nucleotides (or "nucleotide analogues), or a mixture of natural nucleotides and non-natural nucleotides. Non-natural nucleotides that may be present in the oligonucleotides include, but are not limited to, peptide nucleic acid (PNA) nucleotides, Morpholino nucleotides, locked nucleic acid (LNA) nucleotides, bridged nucleic acid (BNA) nucleotides, glycol nucleic acid (GNA) nucleotides, threose nucleic acid (TNA) nucleotides, etc. According to certain embodiments, the oligonucleotides of the oligonucleotide pool include one or more locked nucleic acid (LNA) nucleotides. In certain aspects, one or more nucleotides of the complementarity regions of the oligonucleotides are non-natural nucleotides, e.g., one or more LNA nucleotides. For example, each nucleotide of the complementarity regions of the oligonucleotides may be a non-natural nucleotide, e.g., each nucleotide of the complementarity regions of the oligonucleotides may be an LNA nucleotide. According to certain embodiments, the oligonucleotides of the oligonucleotide pool include one or more bridged nucleic acid (BNA) nucleotides. In certain aspects, one or more nucleotides of the complementarity regions of the oligonucleotides are non-natural nucleotides, e.g., one or more BNA nucleotides. For example, each nucleotide of the complementarity regions of the oligonucleotides may be a non-natural nucleotide, e.g., each nucleotide of the complementarity regions of the oligonucleotides may be a BNA nucleotide.

In certain aspects, the oligonucleotides of the oligonucleotide pool are not phosphorylated. In certain aspects, the oligonucleotides of the oligonucleotide pool are phosphorylated. In certain aspects, the oligonucleotides of the oligonucleotide pool are phosphorylated after hybridizing to the target nucleic acids. For example, after hybridizing to the target nucleic acid, and ligation of the 3' end of a strand in an oligonucleotide to a 5' phosphorylated end of a strand in the target nucleic acid, the 5' end of the opposite strand in the oligonucleotide is phosphorylated and then subsequently ligated to the 3' end of the opposite strand in the target nucleic acid. In certain aspects, the oligonucleotides of the oligonucleotide pool are phosphorylated prior to hybridizing to the target nucleic acids. In such aspects, a method may include prevention of oligonucleotide dimer formation (e.g., by adjusting the ratio of oligonucleotides to target nucleic acids) and/or removal of oligonucleotide dimers (e.g., by way of a nucleic acid size selection method).

The term "overhang" generally refers to a single stranded portion at an end of a nucleic acid molecule. For example, a nucleic acid molecule may include a double stranded or "duplex" region comprising one or more paired nucleotides (bases) and a single stranded or "overhang" region comprising one or more unpaired nucleotides (bases). Typically, an overhang refers to a single stranded region at an end of a nucleic acid molecule (e.g., as opposed to a single stranded region flanked by double stranded regions). An overhang may be described herein as a 5' overhang or a 3' overhang. A 5' overhang generally refers to a single stranded region at the end of a nucleic acid molecule that reads according to conventional nucleic acid directionality in a 3' to 5' direction starting at the junction where the duplex portion ends and the single stranded portion begins and ending at the terminus (free end) of the overhang. A 3' overhang generally refers to a single stranded region at the end of a nucleic acid molecule that reads according to conventional nucleic acid directionality in a 5' to 3' direction starting at the junction where the duplex portion ends and the single stranded portion begins and ending at the terminus (free end) of the overhang. As described herein, target nucleic acids may comprise an overhang (e.g., at one end of the nucleic acid molecule) and may comprise two overhangs (e.g., at both ends of the nucleic acid molecule). In some embodiments, target nucleic acids comprise two overhangs, one overhang and one blunt end, two blunt ends, or a combination of these. In some embodiments, target nucleic acids comprise two 3' overhangs, two 5' overhangs, one 3' overhang and one 5' overhang, one 3' overhang and one blunt end, one 5' overhang and one blunt end, two blunt ends, or a combination of these. In some embodiments, overhangs in target nucleic acids are native overhangs. Native overhangs generally refer to overhangs that have not been modified (e.g., have not been filled in, have not been cleaved, have not been introduced) prior to combining the sample composition with the oligonucleotide pool. Native overhangs generally do not include overhangs created by contacting an isolated sample with a cleavage agent (e.g., endonuclease, exonuclease, restriction enzyme).

As described herein, oligonucleotides may comprise an overhang (e.g., at one end of the oligonucleotide) and may comprise two overhangs (e.g., at both ends of the oligonucleotide). In some embodiments, oligonucleotides comprise two overhangs, one overhang and one blunt end, two blunt ends, or a combination of these. In some embodiments, oligonucleotides comprise two 3' overhangs, two 5' overhangs, one 3' overhang and one 5' overhang, one 3' overhang and one blunt end, one 5' overhang and one blunt end, two blunt ends, or a combination of these. For hairpin structure oligonucleotides described herein, such oligonucleotides (e.g., in the uncleaved state) generally comprise one overhang (e.g., a 5' overhang or a 3' overhang), and in certain instances, no overhang (i.e., a blunt end). Generally, one of the overhangs in an oligonucleotide herein comprises the complementarity region. Often, one of the overhangs in an oligonucleotide herein is the complementarity region. When discussing oligonucleotides herein, the terms "overhang" and "complementarity region" may be used interchangeably. When discussing oligonucleotides and target nucleic acids herein, the terms "overhang" and "overhang region" may be used interchangeably.

The terms "complementary" or "complementarity" as used herein refer to a nucleotide sequence that base-pairs by non-covalent bonds to a region of a target nucleic acid, e.g., the overhang region of a nucleic acid of the target nucleic acids (e.g., 5' phosphorylated nucleic acids). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" or "complementarity" refers to a nucleotide sequence that is at least partially complementary. These terms may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, the complementarity region of an oligonucleotide of the oligonucleotide pool may be perfectly (i.e., 100%) complementary to the overhang of a nucleic acid of the 5' nucleic acids, or the complementarity region of the oligonucleotide may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

In certain aspects, "complementary" or "complementarity" may refer structural complementarity (e.g., overhang complementarity). For example, a target nucleic acid having a 3', 6 base-pair overhang may have structural complementarity with an oligonucleotide having a 5', 6 base-pair overhang. Structural complementarity may include non-specific base pairing. In certain embodiments, an oligonucleotide overhang comprises a complementarity region having one or more nucleotides capable of non-specific base pairing to bases in the target nucleic acids. For example, a target nucleic acid having a 3', 6 base-pair overhang may have structural complementarity with an oligonucleotide having a 5', 6 base-pair overhang, where the oligonucleotide overhang comprises one or more nucleotides that can pair non-specifically with all or some of the base possibilities at a corresponding position in the target nucleic acid overhang. In certain embodiments, an oligonucleotide overhang comprises a complementarity region where all nucleotides are capable of non-specific base pairing to bases in the target nucleic acids. Nucleotides capable of non-specific base pairing may be referred to as "universal bases" which can replace any of the four typical bases described above (e.g., nitroindole, 5-nitroindole, 3-nitropyrrole, inosine, deoxyinosine, 2-deoxyinosine) or "degenerate/wobble bases" which can replace two or three (but not all) of the four typical bases (e.g., non-natural base P and K). In certain embodiments, an oligonucleotide overhang comprises a complementarity region comprising one or more universal bases. In certain embodiments, an oligonucleotide overhang comprises a complementarity region consisting of universal bases.

The "conditions" during the combining step are those conditions in which oligonucleotides of the oligonucleotide pool specifically hybridize to nucleic acids of the target nucleic acids (e.g., 5' phosphorylated nucleic acids) having overhang regions that are complementary in sequence and have corresponding lengths with respect to the complementarity regions of the oligonucleotides. In some embodiments, corresponding length refers to the same length (i.e., the same number of bases in the complementarity region and the target nucleic overhang). Whether specific hybridization occurs is determined by such factors as the degree of complementarity between the complementarity regions and the overhang regions, the length thereof, and the temperature at which the hybridization occurs, which may be informed by the melting temperatures ($T_M$) of the complementarity regions/overhangs. The melting temperature refers to the temperature at which half of the complementarity regions/overhangs remain hybridized and half of the complementarity regions/overhangs dissociate into single strands. The $T_m$ of a duplex may be experimentally determined or predicted using the following formula $T_m$=81.5+16.6(log 10[$Na^+$])+0.41 (fraction G+C)−(60/N), where N is the chain length and [$Na^+$] is less than 1 M. See Sambrook and Russell (2001; Molecular Cloning: A Laboratory Manual, 3rd ed., Cold Spring Harbor Press, Cold Spring Harbor N.Y., Ch. 10). Other more advanced models that depend on various parameters may also be used to predict $T_m$ of complementarity region/overhang duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

According to certain embodiments, the oligonucleotides of the oligonucleotide pool include one or more portions (or "domains") other than the complementarity region and the complementarity region identification sequence. Such additional portions may be provided, e.g., to facilitate one or more downstream applications that utilize the hybridization products or derivatives thereof, such as nucleic acid amplification, sequencing (e.g., high-throughput sequencing), or both. In certain aspects, the additional portion (that is, other than the complementarity region and the complementarity region identification sequence) includes a nucleic acid binding domain. Nucleic acid binding domains of interest include, e.g., primer binding domains. According to certain embodiments, the additional portion includes all or a portion of a sequencing adapter.

By "sequencing adapter" is meant one or more nucleic acid domains that include at least a portion of a nucleic acid sequence (or complement thereof) utilized by a sequencing platform of interest, such as a sequencing platform provided by Illumina® (e.g., the HiSeq™, MiSeq™ and/or Genome Analyzer™ sequencing systems); Oxford Nanopore™ Technologies (e.g., the MinION sequencing system), Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, the sequencing adapter is, or includes, a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a barcode domain (e.g., a domain that uniquely identifies the sample source of the nucleic acid being sequenced to enable sample multiplexing by marking every molecule from a given sample with a specific barcode or "tag"; such "barcode domain" typically is not the same as the barcodes described herein for use as complementarity region identification sequences); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest, e.g., to determine expression levels based on the number of instances a unique tag is sequenced; a complement of any such domains; or any combination thereof. In certain aspects, a barcode domain (e.g., sample index tag) and a molecular identification domain (e.g., a molecular index tag) may be included in the same nucleic acid.

When the oligonucleotides include an additional portion that includes all or a portion of a sequencing adapter, one or more additional sequencing adapters and/or a remaining portion of a sequencing adapter may be added to the hybridization products using a variety of approaches. For example, additional and/or remaining portions of sequencing adapters may be added via by ligation, PCR amplification, or the like. In the case of PCR, an amplification primer pair may be employed that includes a first amplification primer that includes a 3' hybridization region (e.g., for hybridizing to the oligonucleotide portion of the hybridization products at one end of the hybridization products) and a 5' region including an additional and/or remaining portion of a sequencing adapter, and a second amplification primer that includes a 3' hybridization region (e.g., for hybridizing to the oligonucleotide portion of the hybridization products at the end of the hybridization products opposite the end to which the first amplification primer hybridizes) and a 5' region including an additional and/or remaining portion of a sequencing adapter.

The target nucleic acids (e.g., 5' phosphorylated nucleic acids) may be any nucleic acids of interest. The nucleic acids may be polymers of any length composed of deoxyribonucleotides, ribonucleotides, or combinations thereof, e.g., 10 bases or longer, 20 bases or longer, 50 bases or longer, 100 bases or longer, 500 bases or longer, 1000 bases or longer, 2000 bases or longer, 3000 bases or longer, 4000 bases or longer, 5000 bases or longer or more bases. In certain aspects, the nucleic acids are polymers composed of deoxyribonucleotides or ribonucleotides, e.g., 10 bases or less, 20 bases or less, 50 bases or less, 100 bases or less, 500 bases or less, 1000 bases or less, 2000 bases or less, 3000 bases or less, 4000 bases or less, or 5000 bases or less.

In certain aspects, the target nucleic acids are deoxyribonucleic acids (DNAs). In certain aspects, the 5' phosphorylated nucleic acids are 5' phosphorylated deoxyribonucleic acids (DNAs). DNAs of interest include, but are not limited to, genomic DNA (including genomic DNA fragments), mitochondrial DNA (mtDNA) complementary DNA (or "cDNA", synthesized from any RNA or DNA of interest), recombinant DNA (e.g., plasmid DNA), or the like.

According to certain embodiments, the target nucleic acids are ribonucleic acids (RNAs). According to certain embodiments, the 5' phosphorylated nucleic acids are 5' phosphorylated ribonucleic acids (RNAs). RNAs of interest include, but are not limited to, messenger RNA (mRNA), microRNA (miRNA), small interfering RNA (siRNA), transacting small interfering RNA (ta-siRNA), natural small interfering RNA (nat-siRNA), ribosomal RNA (rRNA), transfer RNA (tRNA), small nucleolar RNA (snoRNA), small nuclear RNA (snRNA), long non-coding RNA (lncRNA), non-coding RNA (ncRNA), transfer-messenger RNA (tmRNA), precursor messenger RNA (pre-mRNA), small Cajal body-specific RNA (scaRNA), piwi-interacting RNA (piRNA), endoribonuclease-prepared siRNA (esiRNA), small temporal RNA (stRNA), signal recognition RNA, telomere RNA, ribozyme, or any combination of such RNA types or subtypes. In certain aspects, the subject methods find use in detecting/identifying overhangs in RNAs of interest that result from secondary RNA structure, e.g., intramolecular hybridization (e.g., stem formation).

The target nucleic acids (e.g., 5' phosphorylated nucleic acids) may be prepared from any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of an animal. In some embodiments, the animal is a mammal (e.g., a mammal from the genus *Homo*, a rodent (e.g., a mouse or rat), a dog, a cat, a horse, a cow, or any other mammal of interest). In other aspects, the nucleic acid sample is isolated/obtained from a source other than a mammal, such as bacteria, yeast, insects (e.g., *Drosophila*), amphibians (e.g., frogs (e.g., *Xenopus*)), viruses, plants, or any other non-mammalian nucleic acid sample source.

The nucleic acid sample may be obtained (e.g., isolated) from an extant organism or animal. In other aspects, however, the nucleic acid sample may be obtained (e.g., isolated) from an extinct (or "ancient") organism or animal, e.g., an extinct mammal, such as an extinct mammal from the genus *Homo*. In some aspects, the nucleic acid may be obtained as part of a forensics analysis. In some aspects, the nucleic acid may be obtained as part of a diagnostic analysis.

In some embodiments, target nucleic acids (e.g., 5' phosphorylated nucleic acids) may comprise degraded DNA. Degraded DNA may be referred to as low-quality DNA or highly degraded DNA. Degraded DNA may be highly fragmented, and may include damage such as base analogs and abasic sites subject to miscoding lesions. For example, sequencing errors resulting from deamination of cytosine residues may be present in certain sequences obtained from degraded DNA (e.g., miscoding of C to T and G to A).

According to certain embodiments, the target nucleic acids comprise cell-free nucleic acids, e.g., cell-free DNA, cell-free RNA, or both. According to certain embodiments, the 5' phosphorylated nucleic acids are produced from cell-free nucleic acids, e.g., cell-free DNA, cell-free RNA, or both. Such cell-free nucleic acids may be obtained from any suitable source. In certain aspects, the cell-free nucleic acids are obtained from a body fluid sample selected from the group consisting of: whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion, and stool. In some embodiments, the cell-free nucleic acids are cell-free fetal DNAs. In certain aspects, the cell-free nucleic acids are circulating tumor DNAs. In some embodiments, the cell-free nucleic acids comprise infectious agent DNAs. In some embodiments, the cell-free nucleic acids comprise DNAs from a transplant.

The term "cell-free nucleic acid" as used herein can refer to nucleic acid isolated from a source having substantially no cells. Cell-free nucleic acid may be referred to as "extracellular" nucleic acid, "circulating cell-free" nucleic acid (e.g., CCF fragments, ccf DNA) and/or "cell-free circulating" nucleic acid. Cell-free nucleic acid can be present in and obtained from blood (e.g., from the blood of an animal, from the blood of a human subject). Cell-free nucleic acid often includes no detectable cells and may contain cellular elements or cellular remnants. Non-limiting examples of acellular sources for cell-free nucleic acid are described above. Obtaining cell-free nucleic acid may include obtaining a sample directly (e.g., collecting a sample, e.g., a test sample) or obtaining a sample from another who has collected a sample. Without being limited by theory, cell-free nucleic acid may be a product of cell apoptosis and cell breakdown, which provides basis for cell-free nucleic acid often having a series of lengths across a spectrum (e.g., a "ladder"). In some embodiments, sample nucleic acid from a test subject is circulating cell-free nucleic acid. In some embodiments, circulating cell free nucleic acid is from blood plasma or blood serum from a test subject. In some aspects, cell-free nucleic acid is degraded.

Cell-free nucleic acid can include different nucleic acid species, and therefore is referred to herein as "heterogeneous" in certain embodiments. For example, a sample from a subject having cancer can include nucleic acid from cancer cells (e.g., tumor, neoplasia) and nucleic acid from non-cancer cells. In another example, a sample from a pregnant female can include maternal nucleic acid and fetal nucleic acid. In another example, a sample from a subject having an infection or infectious disease can include host nucleic acid and nucleic acid from the infectious agent (e.g., bacteria, fungus, protozoa). In another example, a sample from a subject having received a transplant can include host nucleic acid and nucleic acid from the donor organ or tissue. In some instances, cancer, fetal, infectious agent, or transplant nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is cancer, fetal, infectious agent, or transplant nucleic acid). In another example, heterogeneous cell-free nucleic acid may include nucleic acid from two or more subjects (e.g., a sample from a crime scene).

The nucleic acid sample may be a tumor nucleic acid sample (that is, a nucleic acid sample isolated from a tumor). "Tumor", as used herein, refers to all neoplastic cell growth and proliferation, whether malignant or benign, and all pre-cancerous and cancerous cells and tissues. The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, various types of head and neck cancer, and the like.

In some embodiments, nucleic acid is provided for conducting methods described herein after processing of the sample(s) containing the nucleic acid. For example, a nucleic acid can be extracted, isolated, purified, or partially purified from the sample(s) and/or concentrated. The term "isolated" generally refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" can refer to a nucleic acid removed from a subject (e.g., a human subject). An isolated nucleic acid can be provided with fewer non-nucleic acid components (e.g., protein, lipid, carbohydrate) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" generally refers to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. In some embodiments, nucleic acid is concentrated (e.g., the amount of nucleic acid is increased per volume of solution).

Approaches, reagents and kits for isolating, purifying and/or concentrating DNA and RNA from sources of interest are known in the art and commercially available. For example, kits for isolating DNA from a source of interest include the DNeasy®, RNeasy®, QIAamp®, QIAprep® and QIAquick® nucleic acid isolation/purification kits by Qiagen, Inc. (Germantown, Md.); the DNAzol®, ChargeSwitch®, Purelink®, GeneCatcher® nucleic acid isolation/purification kits by Life Technologies, Inc. (Carlsbad, Calif.); the NucleoMag®, NucleoSpin®, and NucleoBond® nucleic acid isolation/purification kits by Clontech Laboratories, Inc. (Mountain View, Calif.). In certain aspects, the nucleic acid is isolated from a fixed biological sample, e.g., formalin-fixed, paraffin-embedded (FFPE) tissue. Genomic DNA from FFPE tissue may be isolated using commercially available kits—such as the AllPrep® DNA/RNA FFPE kit by Qiagen, Inc. (Germantown, Md.), the RecoverAll® Total Nucleic Acid Isolation kit for FFPE by Life Technologies, Inc. (Carlsbad, Calif.), and the NucleoSpin® FFPE kits by Clontech Laboratories, Inc. (Mountain View, Calif.).

When an organism, plant, animal, etc. from which the nucleic acid sample is obtained (e.g., isolated) is extinct (or "ancient"), suitable strategies for recovering such nucleic acids are known and include, e.g., those described in Green et al. (2010) *Science* 328(5979):710-722; Poinar et al. (2006) *Science* 311(5759):392-394; Stiller et al. (2006)

*Proc. Natl. Acad. Sci.* 103(37):13578-13584; Miller et al. (2008) *Nature* 456(7220):387-90; Rasmussen et al. (2010) *Nature* 463(7282):757-762; and elsewhere.

In some embodiments, methods herein comprise preparing a nucleic acid composition (e.g., a nucleic acid composition comprising target nucleic acids), prior to combining the composition with a pool of oligonucleotides. In some embodiments, preparing a nucleic acid composition comprises isolating nucleic acid from a sample, thereby generating the nucleic acid composition. In some embodiments, a nucleic acid composition is prepared by a process consisting essentially of isolating nucleic acid from a sample, thereby generating the nucleic acid composition. In some embodiments, a nucleic acid composition is prepared by a process consisting essentially of isolating nucleic acid from a sample, thereby generating isolated nucleic acid; and modifying one or both ends of the isolated nucleic acid with a phosphate moiety or chemically reactive moiety, thereby generating the nucleic acid composition. In this context, "consisting essentially of" means that the nucleic acid in the prepared composition can be modified with any agents or conditions suitable to facilitate combining a target nucleic acid composition with an oligonucleotide pool (e.g., buffers, temperature modification).

In certain aspects, target nucleic acids are in solution when combined with the pool. In certain aspects, target nucleic acids are not in a fixed cell sample, and are not in a fixed tissue sample. For example, in some embodiments, the methods include combining a nucleic acid composition solution comprising target nucleic acids that are not in a fixed cell sample, and/or are not in a fixed tissue sample, and that comprise an overhang; and an oligonucleotide pool comprising oligonucleotides, where some or all of the oligonucleotides comprises (i) a complementarity region capable of hybridizing to an overhang in a target nucleic acid, and (ii) a complementarity region identification polynucleotide; oligonucleotides in the pool include complementarity regions of different lengths; and the complementarity region identification polynucleotide is specific to one or more features of the complementarity region (e.g., length).

In certain aspects, the methods of the present disclosure further include sequencing the hybridized oligonucleotides and nucleic acids (that is, the "hybridization products" produced during the combining step). By "sequencing the hybridized oligonucleotides and nucleic acids" or "sequencing the hybridization products" is meant determining the nucleotide sequences of the hybridized oligonucleotides and nucleic acids/hybridization products or derivatives thereof. Derivatives of the hybridized oligonucleotides and nucleic acids/hybridization products may be prepared, e.g., by ligating the hybridized oligonucleotides and nucleic acids, PCR-amplifying the hybridization products, or a combination thereof.

In some embodiments, the sequencing process is a highly multiplexed sequencing process. In some embodiments, the sequencing process generates sequencing reads. In some embodiments, a method herein comprises determining the sequence of an overhang for the target nucleic acids based on the sequencing reads.

In some embodiments, a method herein comprises determining a sequence of a complementarity region identification polynucleotide based on the sequencing reads. In some embodiments, a method herein comprises comprising determining lengths of the overhangs for the target nucleic acids.

The sequencing may be carried out on any suitable sequencing platform, including a Sanger sequencing platform, a high throughput sequencing (HTS) (or "next generation sequencing (NGS)") platform, or the like. HTS/NGS sequencing platforms of interest include, but are not limited to, a sequencing platform provided by Illumina® (e.g., the HiSeq™, MiSeq™ and/or Genome Analyzer™ sequencing systems); Oxford Nanopore™ Technologies (e.g., the MinION sequencing system), Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest. Detailed protocols for preparing the hybridization products for sequencing (e.g., by amplification (e.g., solid-phase amplification), or the like), sequencing the amplicons, and analyzing the sequencing data are available from the manufacturer of the sequencing system of interest.

Some HTS/NGS sequencing platforms require that the nucleic acids to be sequenced have a first adapter at one end and a second adapter at the other end, where the first and second adapters may be the same or different. One example scheme for producing hybridization products having different adapters at each end is shown in FIG. 1. In the specific non-limiting example of FIG. 1, an Illumina P5 adapter is provided at one end of the hybridization products and an Illumina P7 adapter is provided at the opposite end. As such, the oligonucleotides of the oligonucleotide pool may be designed to provide one or more sequencing adapters (or portions thereof) at one or both ends of the hybridization products to facilitate downstream sequencing of the products on the desired HTS/NGS sequencing platform.

When the methods of the present disclosure further include sequencing the hybridization products, the resulting sequencing data may be used to assess a variety of properties of the target nucleic acids (e.g., 5' phosphorylated nucleic acids), and accordingly, the nucleic acids from which the 5' phosphorylated nucleic acids were prepared and/or from which the target nucleic acids were obtained. According to certain embodiments, the methods of the present disclosure include determining the overhang content of the target nucleic acids (e.g., 5' phosphorylated nucleic acids) based on the number of sequencing reads that include the complementarity region identification sequences corresponding to the various complementarity regions of oligonucleotides hybridized to nucleic acids of the target nucleic acids (e.g., 5' phosphorylated nucleic acids). In this way, the complementarity region identification sequences (e.g., barcodes) uniquely identify each type of oligonucleotide complementarity region, and in turn, uniquely identify each type of overhang present in the target nucleic acids (e.g., 5' phosphorylated nucleic acids) to which the complementarity regions specifically hybridize. The "overhang content" may include the lengths, identities (5' overhang or 3' overhang), sequences, or any combination thereof, of overhangs present in the 5' phosphorylated nucleic acids (and accordingly, the nucleic acids from which the 5' phosphorylated nucleic acids were prepared). In some embodiments, the methods include identifying the source of the nucleic acid sample from which the 5' phosphorylated nucleic acids were produced and/or from which the target nucleic acids were obtained (e.g., for forensic purposes) based on the overhang content.

In some aspects, a method herein comprises analyzing a particular overhang in a nucleic acid composition. Such methods may comprise sequencing nucleic acids according to a method described herein and quantifying the amount of overhangs in target nucleic acids, thereby generating an overhang quantification. In some embodiments, the overhang quantification is for an overhang characterized as (i) a 5' overhang, (ii) a 3' overhang, (iii) a particular sequence, (iv) a particular length, or (v) a combination of two, three or four of (i), (ii), (iii) and (iv). In some embodiments, an overhang quantification is for an overhang characterized as (i) a 5' overhang or a 3' overhang, and (ii) a particular length. In some aspects, a method herein comprises identifying the source of target nucleic acids in the nucleic acid sample from which the target nucleic acid composition originated based on the overhang quantification. In some embodiments, a method herein is performed for a forensic analysis. In some embodiments, a method herein is performed for a diagnostic analysis.

A method according to one embodiment of the present disclosure is schematically illustrated in FIG. 1. In this example, nucleic acids from a nucleic acid sample of interest are 5' phosphorylated (e.g., using a polynucleotide kinase (PNK)). Next, the 5' phosphorylated nucleic acids and an oligonucleotide pool are combined under conditions in which oligonucleotides of the oligonucleotide pool hybridize to nucleic acids of the 5' phosphorylated nucleic acids having overhang regions that are complementary in sequence and have corresponding lengths with respect to complementarity regions (shown in black in FIG. 1) of the oligonucleotides. The oligonucleotides include a complementarity region identification sequence ("barcode" in FIG. 1) that uniquely identifies the complementarity region of its respective oligonucleotide. In this example, the oligonucleotides of the oligonucleotide pool are present as duplexes that include the oligonucleotides and nucleic acid strands hybridized to a region of the oligonucleotides adjacent to the complementarity region (see, e.g., "oligo" and "strand" in FIG. 1, second box from the top). Also in this example, the oligonucleotides include a sequencing adapter or portion thereof (see, e.g., "seq adapter" (here, Illumina P5 or P7) in FIG. 1, second box from the top). In the specific embodiment shown in FIG. 1, subsequent to the combining step, the hybridized oligonucleotides and nucleic acids are ligated to each other. Also in this embodiment, the ligation products are subjected to a strand-displacing fill-in reaction (e.g., using Bst polymerase) to complete the sequencing adapter on each end. The products of this example method shown in FIG. 1 may be used in a downstream application of interest, such as high-throughput sequencing (e.g., using an Illumina sequencing platform), e.g., to obtain information regarding the overhang content of the various 5' phosphorylated nucleic acids, and in turn, the various original nucleic acids in the sample of interest.

In some aspects, a method comprises enriching for a species of target nucleic acid. For example, a method herein may comprise enriching for a species of target nucleic acid having a particular overhang feature (e.g., length, type (5', 3'), sequence). Enrichment for a species of target nucleic acid having a particular overhang feature may be achieved according to a particular complementarity region identification polynucleotide. For example, certain target nucleic acids complexed with oligonucleotides described herein may be separated from the rest of the target nucleic acids according to a particular complementarity region identification polynucleotide (e.g., according the sequence, or according to another feature (e.g., modification) of the complementarity region identification polynucleotide). In some embodiments, a method comprises associating complexes (target nucleic acids joined to oligonucleotides herein) with one or more binding agents that specifically hybridize to a particular complementarity region identification polynucleotide, thereby generating enriched complexes. For the term "specifically hybridize," specific, or specificity, generally refers to the binding or hybridization of one molecule to another molecule (e.g., a polynucleotide strand to a complementary strand). That is, specific or specificity refers to the recognition, contact, and formation of a stable complex between two molecules, as compared to substantially less recognition, contact, or complex formation of either of those two molecules with other molecules. The term hybridize generally refers to the formation of a stable complex between two molecules. In some aspects, a polynucleotide complementary to a particular complementarity region identification polynucleotide comprises a member of a binding pair. In some aspects, one or more nucleotides in a particular complementarity region identification polynucleotide comprises a member of a binding pair. Binding pairs may include, for example, antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group, and the like. In some embodiments, one or more binding agents that specifically hybridize to a particular complementarity region identification polynucleotide may be attached to a solid support (e.g., bead). Enrichment for target nucleic acids having a particular species of overhang may be subsequently achieved according to any suitable method for separating biomolecules (e.g., pull down assays, use of solid supports, and the like).

In certain aspects, the methods of the present disclosure comprise the following: (i) combining the nucleic acid composition with the oligonucleotide pool, thereby forming hybridization products; (ii) joining target nucleic acids to the oligonucleotides in the hybridization products, thereby generating complexes; (iii) modifying oligonucleotides in the complexes, thereby generating a nucleic acid library; and (iv) exposing the nucleic acid library to a sequencing process. In certain aspects, the methods of the present disclosure comprise the following: (i) combining the nucleic acid composition with the oligonucleotide pool, thereby forming hybridization products; (ii) joining target nucleic acids to the oligonucleotides in the hybridization products, thereby generating complexes; (iii) associating complexes with one or more binding agents that specifically hybridize to a particular complementarity region identification polynucleotide, thereby generating enriched complexes; (iv) modifying oligonucleotides in the enriched complexes, thereby generating a nucleic acid library; and (v) exposing the nucleic acid library to a sequencing process.

In certain aspects, the methods of the present disclosure consist essentially of the following: (i) combining the nucleic acid composition with the oligonucleotide pool, thereby forming hybridization products; (ii) joining target nucleic acids to the oligonucleotides in the hybridization products, thereby generating complexes; (iii) modifying oligonucleotides in the complexes, thereby generating a nucleic acid library; and (iv) exposing the nucleic acid library to a sequencing process. In certain aspects, the methods of the present disclosure consist essentially of the following: (i) combining the nucleic acid composition with the oligonucleotide pool, thereby forming hybridization products; (ii) joining target nucleic acids to the oligonucleotides in the hybridization products, thereby generating complexes; (iii) associating complexes with one or more binding agents that specifically hybridize to a particular complementarity region identification polynucleotide, thereby generating enriched complexes; (iv) modifying oligonucleotides in the enriched complexes, thereby generating a nucleic acid library; and (v) exposing the nucleic acid library to a sequencing process. When the method above "consist essentially of" the recited steps, the method may include additional routine manipulations associated with any of the recited steps (e.g., washing, heating, cooling, isolating, purifying, concentrating, diluting, separating, and the like).

In some embodiments, modifying the oligonucleotides comprises cleaving one or more cleavage sites in the oligonucleotides (e.g., cleaving at one or more cleavage sites in a hairpin adapter). In some embodiments, modifying the oligonucleotides comprises filling in overhangs in the oligonucleotides opposite to the overhangs in the oligonucleotide that interact with overhangs in the target nucleic acids.

Compositions

Also provided are compositions. The compositions find use, e.g., in practicing the methods of the present disclosure, and may include any components (e.g., oligonucleotide pools, oligonucleotide components/regions, target nucleic acids, 5' phosphorylated nucleic acids, etc.) described hereinabove in the section describing the methods of the present disclosure, in any desired combination.

In some embodiments, the compositions include an oligonucleotide pool including oligonucleotides that include complementarity regions of varying length and nucleotide sequence adapted to specifically hybridize to overhangs in a nucleic acid sample of interest, and a complementarity region identification sequence. The oligonucleotide pool, oligonucleotides, and oligonucleotide regions and sequences, may be as described above in the section describing the subject methods.

Any of the compositions of the present disclosure may be present in a container. Suitable containers include, but are not limited to, tubes, vials, and plates (e.g., a 96- or other-well plate).

In certain aspects, the compositions include the oligonucleotide pool present in a liquid medium. The liquid medium may be an aqueous liquid medium, such as water, a buffered solution, and the like. One or more additives such as a salt (e.g., NaCl, MgCl2, KCl, MgSO4), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a solubilizing agent, a detergent (e.g., a non-ionic detergent such as Tween-20, etc.), a nuclease inhibitor, glycerol, a chelating agent, and the like may be present in such compositions.

In some embodiments, a composition of the present disclosure is a lyophilized composition. A lyoprotectant may be included in such compositions in order to protect the oligonucleotide pool against destabilizing conditions during a lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM. In certain aspects, a composition of the present disclosure is in a liquid form reconstituted from a lyophilized form. An example procedure for reconstituting a lyophilized composition is to add back a volume of pure water (typically equivalent to the volume removed during lyophilization); however solutions comprising buffering agents, antibacterial agents, and/or the like, may be used for reconstitution.

In certain aspects, the oligonucleotides of the oligonucleotide pool of the compositions of the present disclosure are present as duplexes including the oligonucleotides and nucleic acid strands hybridized to a region of the oligonucleotides adjacent to the complementarity region. According to certain embodiments, the region of the oligonucleotides adjacent to the complementarity region includes all or a portion of the complementarity region identification sequence.

In some embodiments, the oligonucleotides of the oligonucleotide pool of the compositions of the present disclosure include a portion other than the complementarity region and the complementarity region identification sequence. For example, a portion other than the complementarity region and the complementarity region identification sequence may include a nucleic acid binding domain. The nucleic acid binding domain may be a primer binding domain. In certain aspects, the portion other than the complementarity region and the complementarity region identification sequence includes all or a portion of a sequencing adapter. In certain aspects, the nucleotide sequences of the complementarity regions are random nucleotide sequences across the length of the complementarity regions.

In certain aspects, the oligonucleotides of the oligonucleotide pool present in the subject compositions comprise one or more backbone modifications. For example, oligonucleotide backbones may be modified relative to native DNA or RNA. Backbone modifications may include, for example, replacement of the phosphodiester group or the whole sugar phosphodiester with alternative anionic, neutral and cationic structures. In the compositions of the present disclosure, the oligonucleotides of the oligonucleotide pool may include natural nucleotides, non-natural nucleotides (or "nucleotide analogues), or a mixture of natural nucleotides and non-natural nucleotides. Non-natural nucleotides that may be present in the oligonucleotides include, but are not limited to, peptide nucleic acid (PNA) nucleotides, Morpholino nucleotides, locked nucleic acid (LNA) nucleotides, bridged nucleic acid (BNA) nucleotides, glycol nucleic acid (GNA) nucleotides, threose nucleic acid (TNA) nucleotides, etc. According to certain embodiments, the oligonucleotides of the oligonucleotide pool include one or more locked nucleic acid (LNA) nucleotides. In certain aspects, one or more nucleotides of the complementarity regions of the oligonucleotides are non-natural nucleotides, e.g., one or more LNA nucleotides. For example, each nucleotide of the complementarity regions of the oligonucleotides may be a non-natural nucleotide, e.g., each nucleotide of the complementarity regions of the oligonucleotides may be an LNA nucleotide.

In certain aspects, the oligonucleotides of the oligonucleotide pool present in the subject compositions are not phosphorylated.

According to some embodiments, the compositions of the present disclosure further include nucleic acids from a nucleic acid sample of interest, e.g., target nucleic acids (e.g., 5' phosphorylated nucleic acids) produced from a nucleic acid sample of interest. In certain aspects, when such nucleic acids are present, oligonucleotides of the oligonucleotide pool are hybridized to nucleic acids of the target nucleic acids (e.g., 5' phosphorylated nucleic acids) having overhang regions that are complementary in sequence and have corresponding lengths with respect to the complementarity regions of the oligonucleotides. The nucleic acids may be 5' phosphorylated DNAs, e.g., 5' phosphorylated genomic DNAs (including genomic DNA fragments), 5' phosphorylated mitochondrial DNAs, or the like. Alternatively, or additionally, the nucleic acids may be 5' phosphorylated RNAs.

The target nucleic acids (e.g., 5' phosphorylated nucleic acids) may be from a nucleic acid sample obtained from an organism, plant, animal, etc. For example, the target nucleic acids (e.g., 5' phosphorylated nucleic acids) may be extant animal nucleic acids or extinct (e.g., "ancient") animal nucleic acids. Animal nucleic acids of interest include, but are not limited to, extant or extinct mammalian nucleic acids, nucleic acids from an extant or extinct mammal from the genus *Homo*, and the like.

According to certain embodiments, the target nucleic acids are cell-free nucleic acids. According to certain embodiments, the 5' phosphorylated nucleic acids are 5' phosphorylated cell-free nucleic acids. Cell-free nucleic acids of interest include, but are not limited to, cell-free fetal DNAs, circulating tumor DNAs, and the like.

Kits

As summarize above, the present disclosure provides kits. The kits may include, e.g., any useful components (e.g., oligonucleotide pools, oligonucleotide components/regions, target nucleic acids, 5' phosphorylated nucleic acids, etc.) described hereinabove in the section describing the methods of the present disclosure, in any desired combination.

In certain aspects, a kit of the present disclosure includes any of the compositions of the present disclosure described hereinabove. The kits may further include any reagents, buffers, etc. useful for carrying out embodiments of the methods of the present disclosure. According to some embodiments, a subject kit includes a kinase adapted to 5' phosphorylate nucleic acids of a nucleic acid sample (e.g., a polynucleotide kinase (PNK)), a DNA ligase, an enzyme (e.g., polymerase) suitable for performing a fill-in and/or strand displacement reaction, and any combination thereof.

Components of the kits may be present in separate containers, or multiple components may be present in a single container. A suitable container includes a single tube (e.g., vial), one or more wells of a plate (e.g., a 96-well plate, a 384-well plate, etc.), or the like.

The kits may include instructions, e.g., for using the composition to produce a nucleic acid library. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

Utility

The methods, compositions and kits of the present invention find use in a variety of contexts, including research, clinical, forensic, and other contexts. In certain aspects, the methods find use in producing nucleic acid libraries in which the overhang content of a nucleic acid sample of interest is determined based on the physical association (via hybridization) of complementarity region identification sequences and nucleic acids of the nucleic acid sample of interest, where the complementarity region identification sequences (e.g., barcodes) enable the determination of the presence and/or type of overhang in a nucleic acid to which it is physically associated. Embodiments of the methods of the present disclosure enable the learning, in bulk, of the molecular characteristics of the ends of DNAs, RNAs, or both, in a nucleic acid sample of interest. For example, embodiments of the methods of the present disclosure enable the learning, in bulk, of whether double-stranded DNA or RNA molecules have a 5-prime or 3-prime overhang, how long that overhang is, and/or the like. Embodiments of the methods of the present disclosure enables sequencing of these molecules, using standard HTS sequencing technology and partitioning the resulting sequencing reads into categories that correspond to what type of overhang it had.

Determining the overhang content using the methods of the present disclosure may provide a variety of useful information regarding the nucleic acid sample from which the 5' phosphorylated nucleic acids were prepared and/or from which the target nucleic acids were obtained. For example, knowing the overhang content is of value in analyzing cell-free DNA (cfDNA), e.g., from blood plasma or another suitable source. It has been shown that cfDNA derives from a variety of sources including blood cells, fetal cells in pregnant women, tumor cells in individuals having cancer, from transplanted organ tissue in organ transplant recipients, etc. The overhang content provided by embodiments of the methods of the present disclosure can be used to classify sequencing reads, e.g., by source of origin for diagnostic purposes.

Moreover, the overhang content may be used to analyze mixed DNA from forensic samples. For example, DNA from semen, blood, or another source of interest may have end characteristics that are diagnostic for that source, and DNA sequences could be partitioned based on this information.

In addition, determining the overhang content in an ancient DNA sample (e.g., a sample from an extinct organism, plant, or animal) provides information useful in characterizing such samples and the organisms, plants, animals, etc. from which the sample is derived. For example, ancient DNA samples (e.g., a DNA sample from an extinct mammal) often include contaminating DNAs (e.g., contaminating bacterial DNA, or the like). In such cases, the DNA sequences of interest may be partitioned from the contaminating DNA sequences based on the types of overhangs detected, when such types of overhangs are associated with a particular source of DNA.

In certain embodiments, the methods of the present disclosure find use in determining the rate and position of base damage in DNA extracts (e.g., ancient DNA extracts), as a function of the length and type of overhang. Further details of this embodiment are provided in the Experimental section below.

The following examples are offered by way of illustration and not by way of limitation.

EXPERIMENTAL

In standard library preparation protocols, the ends of each double stranded DNA or RNA molecule are made to be blunt ended by the action of an enzyme which fills-in 5' ends and chews back 3' ends. Thus, the actual identity of the molecule ends are lost in these protocols. Presented in the following examples is a method of generating sequencing libraries that introduces a barcode sequence to each read that indicates what kind of overhang, if any, was present in the original molecule.

Example 1—Library Construction and Sequencing

The library preparation employed was consistent with that shown schematically in FIG. 1, the accompanying description of which is provided herein in the Methods section. Features of this example approach included: (i) the barcoded oligos (also referred to herein as "adapters") were not phosphorylated and thus cannot form concatamers, (ii) the complementarity regions were equal proportions of all random sequence of each length, and (iii) a barcode scheme was included in each adapter that was sequenced and indicated the length and identity (5' or 3') of the overhang present on each DNA or RNA fragment.

Several libraries were constructed from an ancient bison extract using the barcoded oligos as described above. In one control experiment, the sample was pre-treated with a cocktail of enzymes that blunt-ended all DNA molecules (experiment APN-09). In another set of experiments, the sample was only treated with PNK (see, FIG. 1) and endogenous ends were left as they were in the sample (experiments APN-15 and APN-16).

After library generation, each library was sequenced on a 2×75 Illumina MiSeq sequencing system run to generate a few million reads from each library.

Example 2—Mapping of Reads to the Bison Genome

Figure 2:
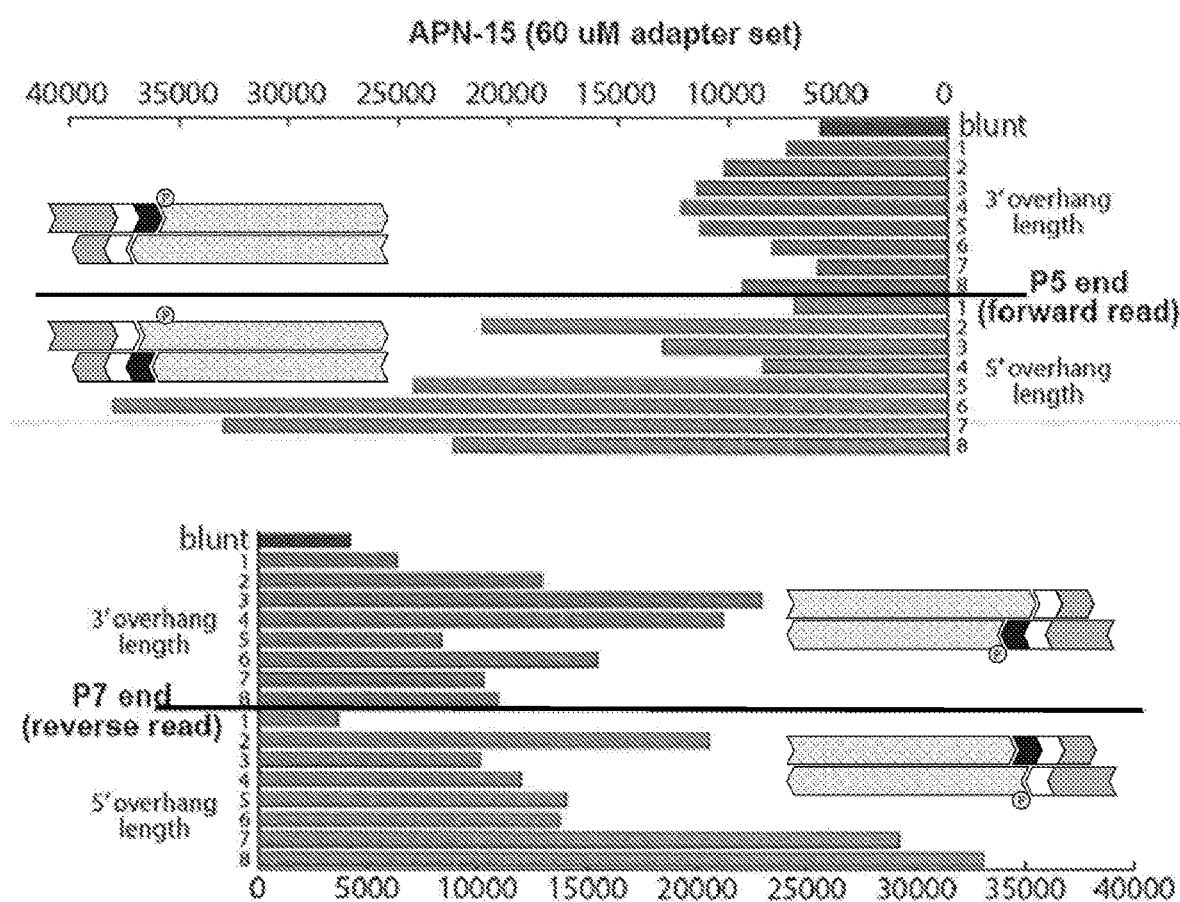
FIG. 2 depicts the number of sequencing reads obtained using a method in accordance with an embodiment of the present disclosure.

FIG. 2 shows the number of reads obtained from a sample that was only treated with PNK (experiment APN-15) that map to the bison genome using the above-described barcoded oligo pool.

The results demonstrated that it is possible to quantify the relative proportion of molecules from an ancient DNA extract that have various lengths of 3' and 5' overhangs on their ends. It was found that: (i) natively blunt ended molecules are rare, at least in the studied bison DNA extract, (ii) 5' overhangs were more common than 3' overhangs, (or it may be due to 3' overhangs not having the correct length in order to produce a molecule suitable for sequencing), (iii) the overlaps identified included overlaps from one to eight nucleotides. Because there were many eight nucleotide barcodes sequenced, this may indicate that there are even longer single-stranded overlaps present in the extract.

In a control experiment (experiment APN-09), nearly all bison reads were from the blunt-ended barcodes.

Example 3—Rate of Mismatches

The APN-15 experiment data was further analyzed to quantify the rate of mismatches between the bison sequence reads and the bison genome. This analysis was designed to show the rate and position of base damage in the ancient DNA extract, as a function of the length and type of single-stranded overhang. It has been shown that cytosine deamination is the predominant form of chemical base-damage in ancient DNA. The result of cytosine deamination, which generates a uracil base, is that the uracil is read as a thymidine. Thus, C to T changes may be commonly found in ancient DNA sequence data. If the deaminated cytosine occurs on the opposite strand of what is read by the sequencer, then the complement of C to T is observed, i.e., G to A. It is also known that the rate of cytosine deamination is much higher in single stranded DNA than in double stranded DNA. Thus, the rate of C to T substitutions may be highest in the beginning section of each molecule, up to the length of the overhang, which is indicated by the corresponding barcode sequence.

Figure 3:
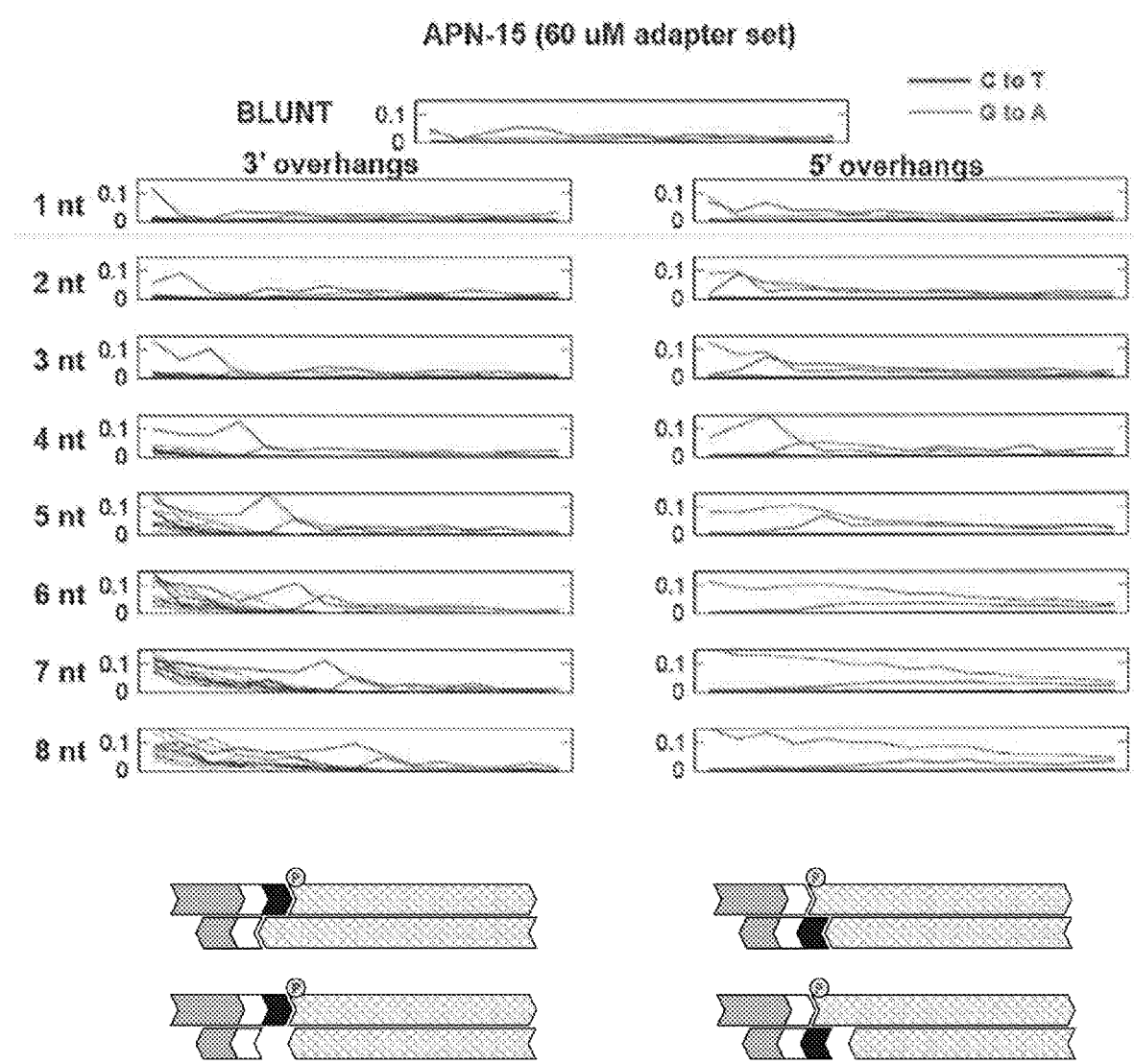
FIG. 3 depicts the rate of mismatches in a library prepared using a method according to an embodiment of the present disclosure.

FIG. 3 shows the rate of C to T and G to A differences in experiment APN-15, as a function of position in the molecule and the length and type of single stranded overhang. In the 3' overhang molecules, the rate of G to A was found to be high up to the point where the double stranded section starts. G to A is analyzed in 3' overhang molecules because the molecule is made by ligating the overhanging adapter to the 3' overhang. Thus, deaminated cytosine will anneal with a molecule that include an A complementary to the uracil. Analysis of the 5' overhangs showed many of the same features, but in complement.

Example 4—Characterization of DNA Fragment Ends in Blood Plasma and Urine from Healthy Subjects To investigate the nature of DNA fragments in blood plasma and in urine, several libraries were made using barcoded variable overhang adapter sets described above and shown in FIG. 1. DNA was purified from 1 mL to 4 mL of healthy donor blood plasma and healthy donor urine using the Qiagen QIAAMP Circulating Nucleic Acids kit. Purified DNA was treated with polynucleotide kinase (PNK) to phosphorylate all free five-prime ends. Then, barcoded variable overhang adapters were ligated to these DNA fragments. For this Example, a single enzyme ligation strategy was used, and the results are shown here. For certain applications, a two enzyme ligation strategy was used to accommodate the non-overlapping activities of blunt-end ligases and nick-sealing ligases. Ligated adapter ends were then filled in with Bst 2.0 polymerase.

Figure 4:
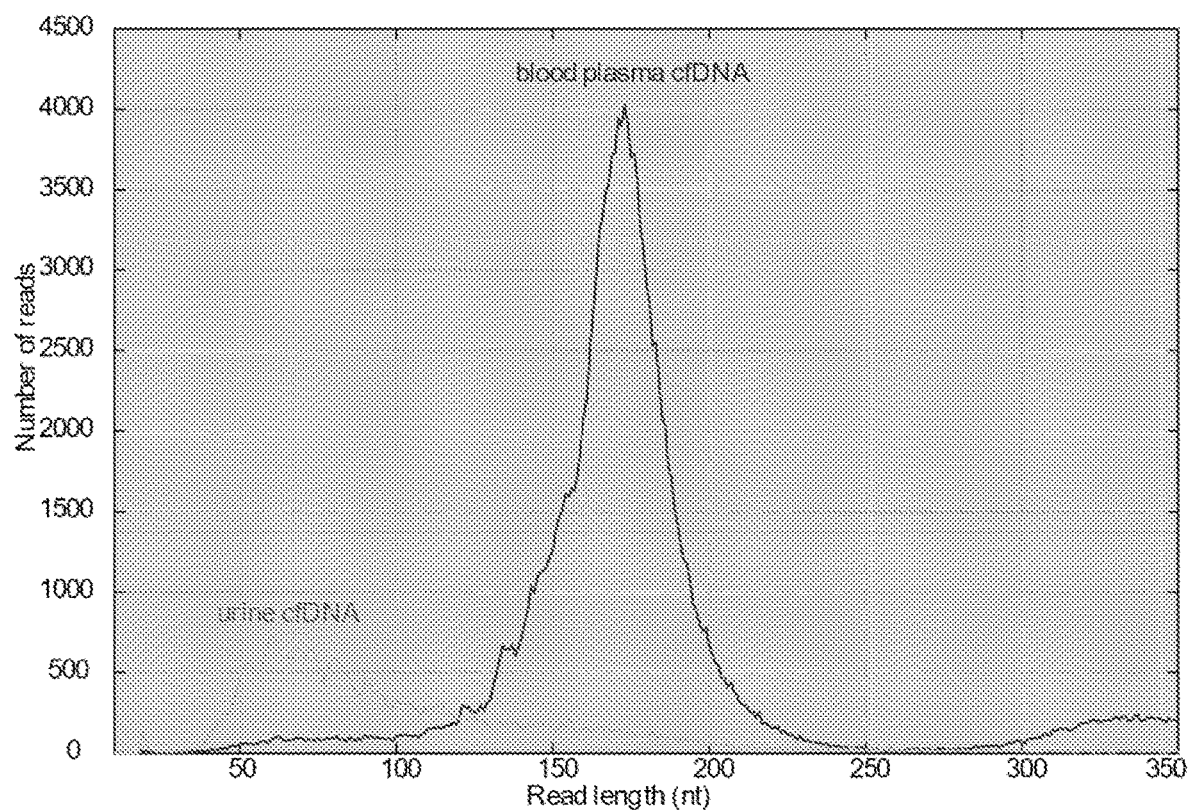
FIG. 4 shows length distribution of DNA fragments purified from blood plasma and urine of a healthy donor.

As shown in FIG. 4, the length distribution of DNA fragments differed between blood plasma samples and urine samples. Generally, blood plasma DNA fragments have a mode around 165 base-pairs long, characteristic of DNA wrapped around a histone. Without being limited by theory, this is consistent with enzymatic degradation of DNA on histones such that DNA fragments comprise DNA associated with a single histone. DNA fragments from urine were shorter and without a clear mode in length distribution.

Figure 5:
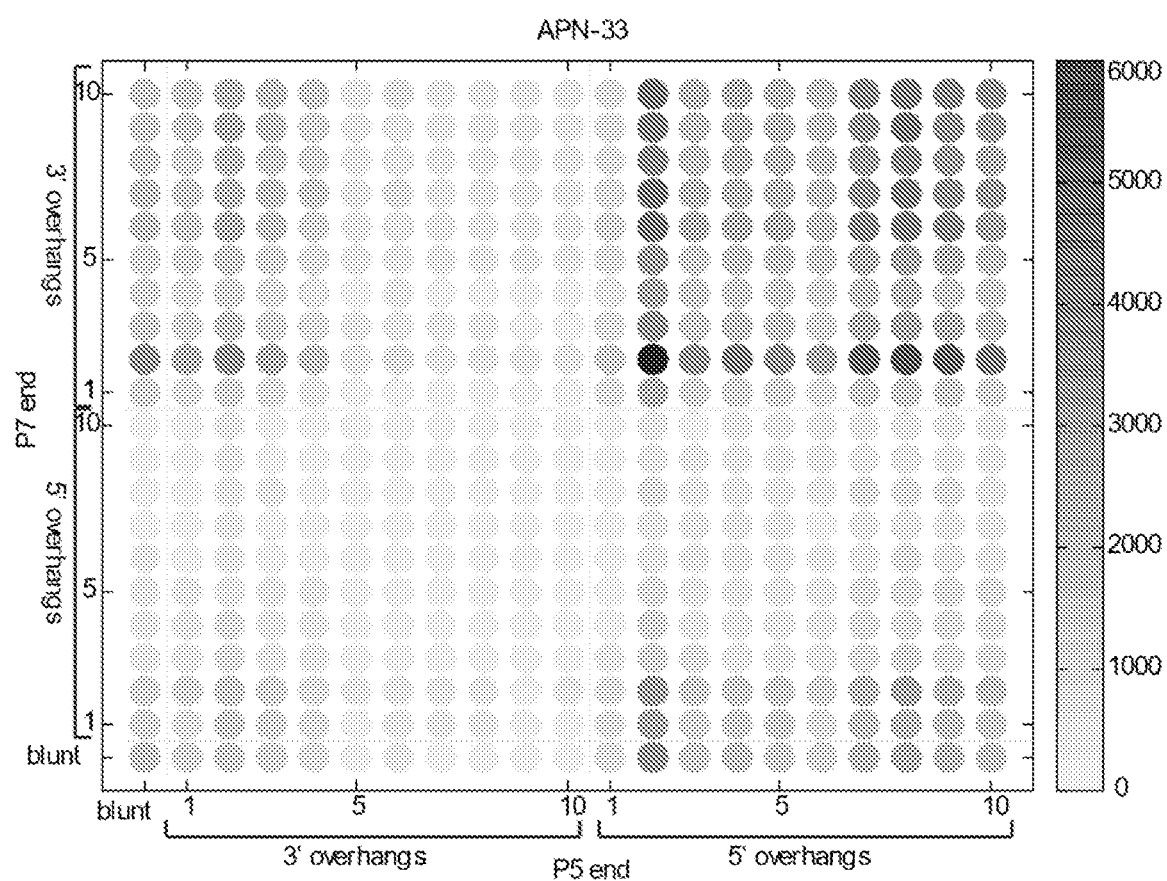
FIG. 5 shows observed counts of each DNA overhang type and length from healthy blood plasma cfDNA.

Barcodes included in the adapter set were used to determine the distribution of overhangs in these data. Specifically, each sequenced fragment that maps to the human genome (nearly all DNA fragments) was classified by which barcode was present on each end of the molecule. In this way, the identities of the ends of each DNA fragment could be surveyed in blood plasma and urine. FIG. 5 shows these counts for the blood plasma sequence data. The most common configuration was the barcode that indicates a 2 base, five-prime (5') overhang on both ends of the molecule. Without being limited by theory, this configuration may be the result of a DFF40/CAD apoptotic endonuclease whose cleavage properties have been characterized on naked DNA substrates. In vitro, DFF40/CAD generally leaves five-prime overhangs and preferentially cleaves around cytosine residues. Analysis of the sequence data produced in this Example showed an enrichment of cytosine bases around the ends of the fragments.

Figure 6:
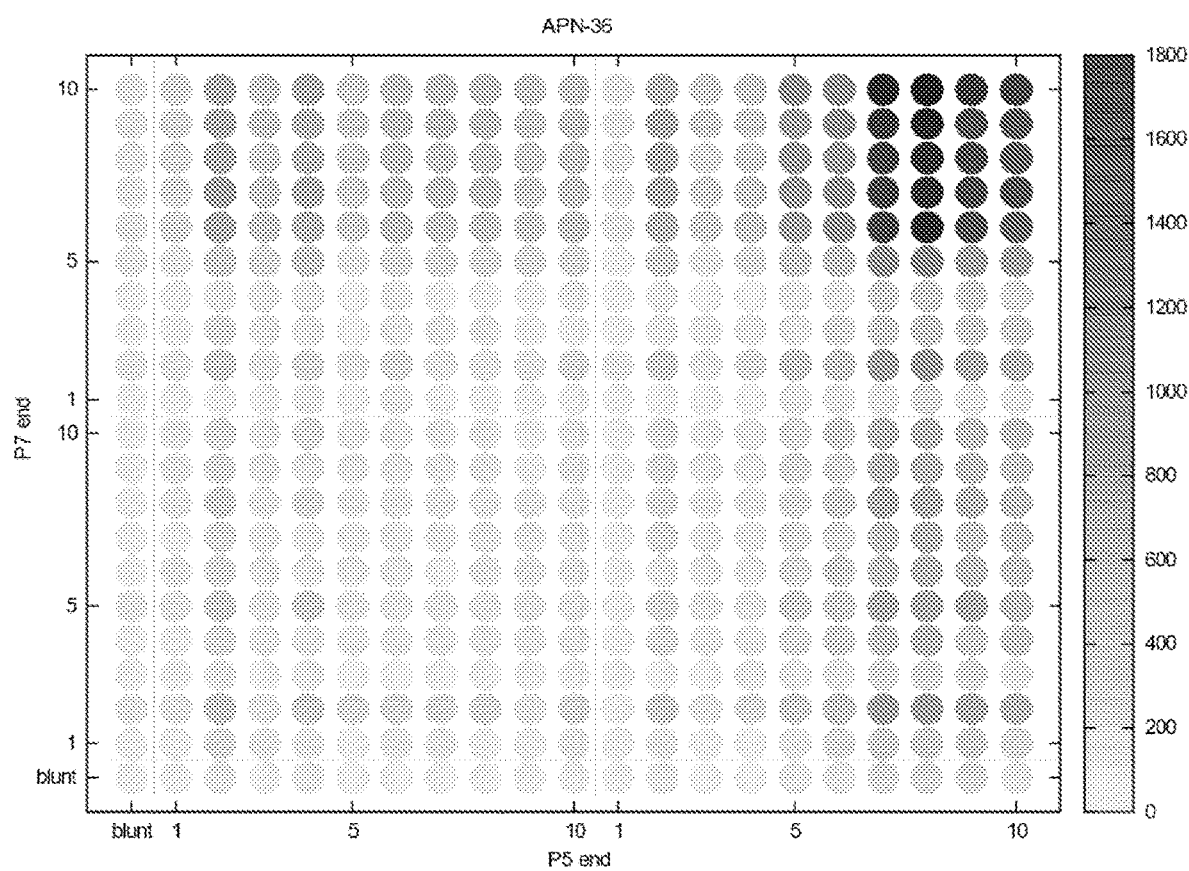
FIG. 6 shows observed counts of each DNA overhang type and length from healthy urine cfDNA.

The same analysis was performed for DNA sequence data from urine samples. These results are shown in FIG. 6. In contrast to the blood plasma DNA, no single configuration was most prevalent. Instead, longer five-prime (5') overhangs were more commonly observed than three-prime (3') overhangs or blunt-ended molecules.

Example 5—Hairpin Barcoded Variable Overhang Adapters

Figure 7:
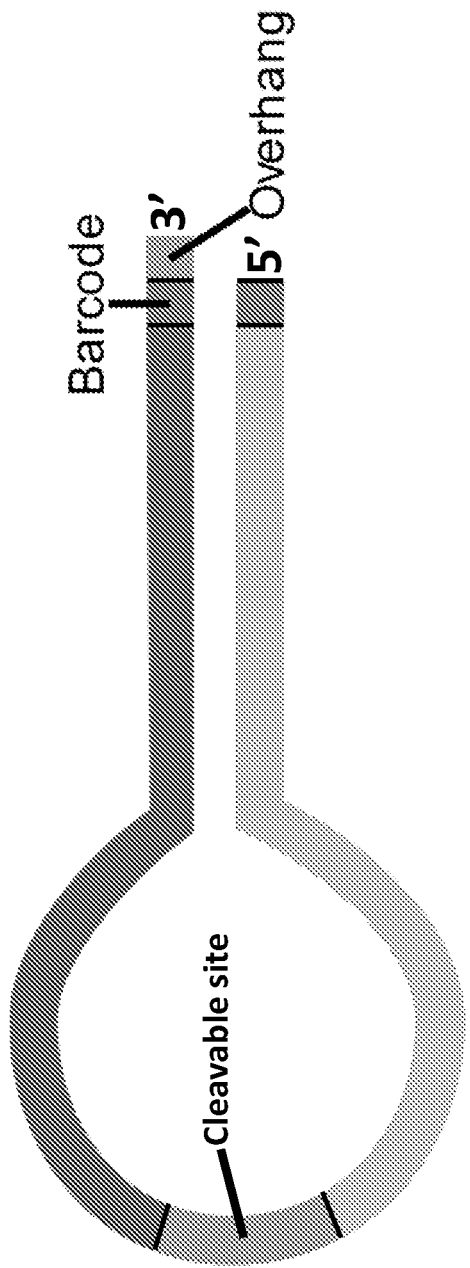
FIG. 7 shows a schematic of a hairpin, barcoded adapter. The cleavable site may contain a chemically cleavable site or an enzymatically cleavable site. The barcode indicates the type and length of the single stranded overhang.

In this Example, another concept for attaching barcoded variable overhang adapters to DNA fragments is described. This concept is shown schematically in FIG. 7, which illustrates one of several possible configurations. A single hairpin adapter can be ligated to each end of a DNA fragment. Because of the polarity of DNA, the top strand of the hairpin adapter shown in FIG. 7 is ligated to the five-prime (5') end of a target DNA molecule and the bottom strand is ligated to the three-prime (3') end of a target DNA molecule. A portion of the top strand is complementary to a portion of the bottom strand, which form the stem region of the adapter; and a portion of the top strand is not complementary to a portion of the bottom strand, which forms the hairpin loop region of the adapter, as shown in FIG. 7. The hairpin is cleaved at a cleavable site using one of several approaches (e.g., chemical, enzymatic). After cleavage, the top sequence and the bottom sequence in the hairpin loop region are separated into different strands, forming a Y-shape at either end of the ligated DNA molecule. The different sequences present in the arms of the Y serve as independent priming sites for amplification into a standard high-throughput sequencing library. For an Illumina sequencing platform, one strand of the adapter includes the P5 adapter sequence and the opposite strand includes the P7 adapter sequence.

Hairpin adapters can have barcodes and overhangs that allow identification of the overhang type (5' or 3') and length as described above for a non-hairpin barcoded variable overhang adapter set. For example, these hairpin adapters can have overhangs of varying length and varying sequence on the 5' or 3' ends of the adapters. Some adapter pools also include hairpin adapters with no overhang (i.e., blunt ended, for ligation to blunt ended target nucleic acids).

Example 6—Immobilized Barcoded Variable Overhang Adapters

In this Example, another concept for attaching barcoded variable overhang adapters to DNA fragments is described. A single-stranded P7 barcoded overhanging adapter was 5' phosphorylated and the 3' end was biotinylated. The biotinylated side was immobilized on streptavidin. The complement to the P7 adapter was hybridized to form a double-stranded immobilized adapter. The double-stranded target nucleic acids were ligated to the immobilized adapter pools. P5 barcoded overhanging adapters were ligated to the free side of the immobilized target nucleic acids. The adapters were then filled in.

Figure 9:
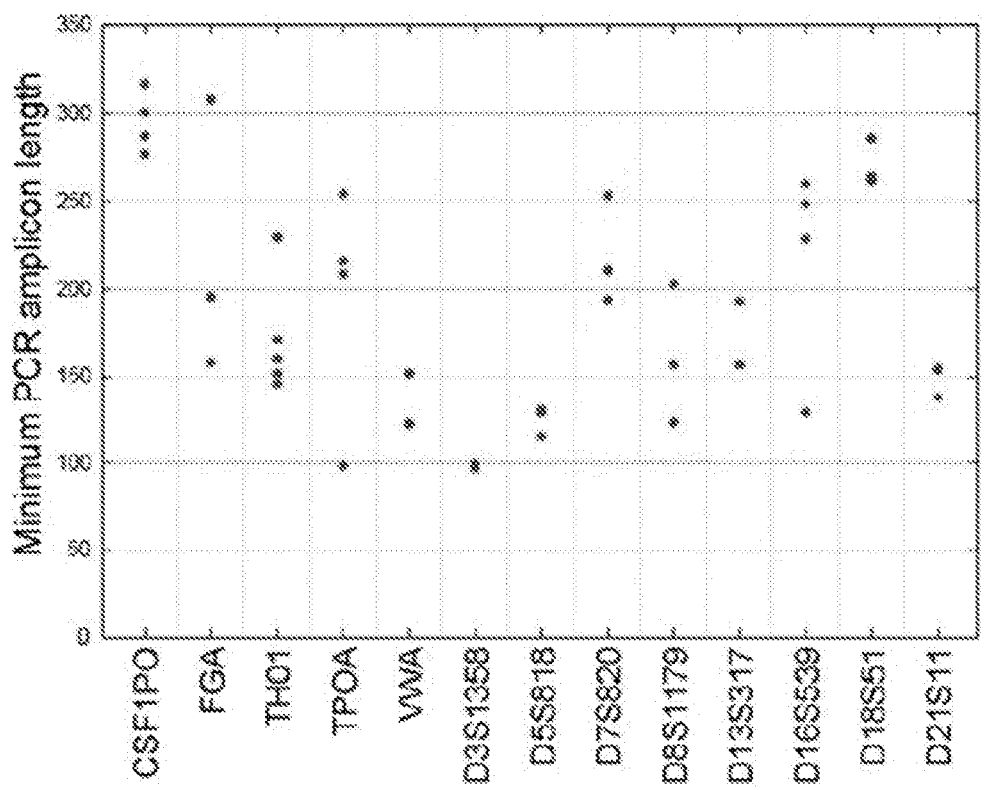
FIG. 9 shows amplicon length of shortest PCR product from 13 standard CODIS markers. Because these markers are length polymorphisms, the smallest amplicon that exists in humans was chosen for the PCR primer sets available from the PowerPlex 1.1 or 16, Profiler Plus, COfiler, or Identifier primer sets. Even mini-STRs require a template molecule beyond the size range typically seen in nuclear DNA in hair shafts (FIG. 8). Data is from World Wide Web Uniform Resource Locator cstl.nist.gov/strbase.

Example 7—Efficient Recovery of DNA Sequence Data and Preservation of the History of DNA Molecules DNA fragments recovered from some sources often is the result of the action of specific nucleases that can leave characteristic overhangs and that act predominantly in specific sequence contexts. In this Example, a technical approach is described that preserves the identity of overhangs on DNA molecules. This approach is applied to difficult biological samples that are generally considered unamenable to forensic analysis. For example, genetic profiles of nuclear genome markers generally are not recoverable from DNA extracted from rootless hair shafts. In this Example, nuclear DNA was present and recoverable from hair shafts, even from hair shafts that are over 100 years old. However, regardless of the age of the sample, this DNA was present in short fragments (FIG. 8). In hair shafts, nuclear DNA fragments generally are the end products of a specific degradation pathway involving DNase1L2, an enzyme that cleaves nuclear DNA. During corneocyte formation (the final maturation of the cells that comprise hair), the nuclear genome is cleaved between nucleosomes such that the remaining DNA is found in short fragments. Thus, even for fresh hair, DNA present in hair shafts is rendered too short for PCR-based STR analysis by a natural and well-described biological process. As shown in FIG. 9, the minimum amplicon length (the size of the shortest variant present in humans) of miniSTRs is longer than the typical fragment lengths of nuclear DNA in hair shafts. Additionally, the amount of DNA recovered from hair shafts is variable and generally low. For these reasons, standard PCR amplification of STR markers using DNA recovered from rootless hair shafts generally will not work.

The DNA sequencing library approach described herein preserves information about the state of the ends of DNA fragments. This approach enables forensic identification from many sample types that have DNA fragmented by post-mortem decay or by natural biological processes. For example, rootless hairs, aged blood stains, and bone fragments all contain DNA in short fragments and were previously poorly amenable or unamenable for forensic identification.

The DNA sequencing library approach described herein is tested on the sample panels enumerated in Table 1 to (1) determine the efficiency of the method in capturing DNA information in sequencing libraries and (2) discover the value of this information for discerning the history of molecules from each source, which may be useful for analyzing complex mixtures.

TABLE 1

| Sample set | Number of samples | Type of sample | Shotgun Library method | Traditional approach for comparison |
|---|---|---|---|---|
| Hair panel | 50 | Rootless hairs (cuttings) | APN + standard | CODIS STR PCR panel |
| Touch DNA | 10 | Swabs from doorknobs | APN + standard | CODIS STR PCR panel; HVRI & HVRII amplicon Sanger Sequencing |
| Bone | 20 | DNA extraction from bone remains | APN + standard | CODIS STR PCR panel |

Each of the sources listed in Table 1 is a potential source of useful forensic data that is currently considered challenging or intractable. After DNA extraction in a dedicated clean-room facility, (1) the amount of DNA recovered from each sample is quantified, (2) barcoded variable overhang adapter libraries that encode the state of the ends of each DNA fragment are generated, (3) standard shotgun libraries using a high efficiency NEB Ultra II kit are generated, and (4) traditional PCR amplification of the traditional CODIS marker panel is performed. For the touch DNA experiment, HVRI and HVRII amplicon products are generated for comparison.

Comparative analyses of these data allows for (1) a determination of the relative efficiency of DNA recovery from the barcoded variable overhang adapter library approach versus traditional approaches and (2) discovery and description of any differences in DNA overhanging ends from DNA from these biological sources.

Example 8—Examples of Embodiments

The examples set forth below illustrate certain embodiments and do not limit the technology.

1. A method of producing a nucleic acid library, comprising: combining:
   5' phosphorylated nucleic acids; and
   an oligonucleotide pool comprising oligonucleotides that comprise:
      complementarity regions of varying length and nucleotide sequence; and
      a complementarity region identification sequence,
   under conditions in which oligonucleotides of the oligonucleotide pool hybridize to nucleic acids of the 5' phosphorylated nucleic acids having overhang regions that are complementary in sequence and have corresponding lengths with respect to the complementarity regions of the oligonucleotides.
2. The method according to embodiment 1, wherein prior to the combining, the method comprises producing the 5' phosphorylated nucleic acids by phosphorylating the 5' ends of nucleic acids from a nucleic acid sample.
3. The method according to embodiment 1 or embodiment 2, wherein subsequent to the combining, the method comprises ligating the hybridized oligonucleotides and nucleic acids.
4. The method according to any one of embodiments 1 to 3, wherein during the combining, the oligonucleotides of the oligonucleotide pool are present as duplexes comprising:
   the oligonucleotides; and
   nucleic acid strands hybridized to a region of the oligonucleotides adjacent to the complementarity region.
5. The method according to embodiment 4, wherein the region of the oligonucleotides adjacent to the complementarity region comprises all or a portion of the complementarity region identification sequence.
6. The method according to embodiment 4 or embodiment 5, wherein the duplex comprises an overhang at the end of the duplex opposite the end that hybridizes to the nucleic acids, and subsequent to the combining, the method comprises filling in the overhang formed by the duplex.
7. The method according to any one of embodiments 1 to 6, wherein the oligonucleotides of the oligonucleotide pool comprise a portion other than the complementarity region and the complementarity region identification sequence.
8. The method according to embodiment 7, wherein the portion other than the complementarity region and the complementarity region identification sequence comprises a nucleic acid binding domain.
9. The method according to embodiment 8, wherein the nucleic acid binding domain is a primer binding domain.
10. The method according to embodiment 8 or embodiment 9, wherein the portion other than the complementarity region and the complementarity region identification sequence comprises all or a portion of a sequencing adapter.
11. The method according to any one of embodiments 1 to 10, wherein the varying nucleotide sequences of the complementarity regions of the oligonucleotides of the oligonucleotide pool are random.
12. The method according to any one of embodiments 1 to 11, wherein the oligonucleotides of the oligonucleotide pool comprise one or more non-natural nucleotides.
13. The method according to embodiment 12, wherein one or more nucleotides of the complementarity regions of the oligonucleotides are non-natural nucleotides.
14. The method according to embodiment 13, wherein each nucleotide of the complementarity regions of the oligonucleotides is a non-natural nucleotide.
15. The method according to any one of embodiments 12 to 14, wherein the non-natural nucleotides are locked nucleic acid (LNA) nucleotides.
16. The method according to any one of embodiments 1 to 15, wherein the oligonucleotides of the oligonucleotide pool are not phosphorylated.
17. The method according to any one of embodiments 1 to 16, wherein the 5' phosphorylated nucleic acids are 5' phosphorylated deoxyribonucleic acids (DNAs).
18. The method according to embodiment 17, wherein the 5' phosphorylated DNAs are 5' phosphorylated genomic DNAs.
19. The method according to any one of embodiments 1 to 16, wherein the 5' phosphorylated nucleic acids are 5' phosphorylated ribonucleic acids (RNAs).
20. The method according to any one of embodiments 1 to 19, wherein the 5' phosphorylated nucleic acids are prepared from a nucleic acid sample obtained from an animal.
21. The method according to embodiment 20, wherein the animal is an extinct animal.
22. The method according to embodiment 20 or embodiment 21, wherein the animal is a mammal.
23. The method according to embodiment 22, wherein the animal is from the genus *Homo*.
24. The method according to any one of embodiments 1 to 23, wherein the 5' phosphorylated nucleic acids are produced from cell-free nucleic acids.
25. The method according to embodiment 24, wherein the cell-free nucleic acids are obtained from a body fluid sample selected from the group consisting of: whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion, and stool.
26. The method according to embodiment 24 or embodiment 25, wherein the cell-free nucleic acids are cell-free fetal DNAs.
27. The method according to embodiment 24 or embodiment 25, wherein the cell-free nucleic acids are circulating tumor DNAs.
28. The method according to any one of embodiments 1 to 27, further comprising sequencing the hybridized oligonucleotides and nucleic acids.
29. The method according to embodiment 28, wherein prior to the sequencing, the method comprises ligating the hybridized oligonucleotides and nucleic acids.
30. The method according to embodiment 28 or 29, comprising determining the overhang content of the 5' phosphorylated nucleic acids based on the number of sequencing reads that include the complementarity region identification sequences corresponding to the various complementarity regions of oligonucleotides hybridized to nucleic acids of the 5' phosphorylated nucleic acids.
31. The method according to embodiment 30, comprising identifying the source of the nucleic acid sample from which the 5' phosphorylated nucleic acids were produced based on the overhang content.

32. A composition, comprising:
  an oligonucleotide pool comprising oligonucleotides that comprise:
    complementarity regions of varying length and nucleotide sequence; and
    a complementarity region identification sequence.
33. The composition of embodiment 32, wherein the composition is present in a container.
34. The composition of embodiment 32 or embodiment 33, wherein the composition is a liquid composition.
35. The composition of embodiment 32 or embodiment 33, wherein the composition is a lyophilized composition.
36. The composition of any one of embodiments 32 to 35, wherein the oligonucleotides of the oligonucleotide pool are present as duplexes comprising:
  the oligonucleotides; and
  nucleic acid strands hybridized to a region of the oligonucleotides adjacent to the complementarity region.
37. The composition of embodiment 36, wherein the region of the oligonucleotides adjacent to the complementarity region comprises all or a portion of the complementarity region identification sequence.
38. The composition of any one of embodiments 32 to 37, wherein the oligonucleotides of the oligonucleotide pool comprise a portion other than the complementarity region and the complementarity region identification sequence.
39. The composition of embodiment 38, wherein the portion other than the complementarity region and the complementarity region identification sequence comprises a nucleic acid binding domain.
40. The composition of embodiment 39, wherein the nucleic acid binding domain is a primer binding domain.
41. The composition of embodiment 39 or embodiment 40, wherein the portion other than the complementarity region and the complementarity region identification sequence comprises all or a portion of a sequencing adapter.
42. The composition of any one of embodiments 32 to 41, wherein the varying nucleotide sequences of the complementarity regions of the oligonucleotides of the oligonucleotide pool are random.
43. The composition of any one of embodiments 32 to 42, wherein the oligonucleotides of the oligonucleotide pool comprise one or more non-natural nucleotides.
44. The composition of embodiment 43, wherein one or more nucleotides of the complementarity regions of the oligonucleotides are non-natural nucleotides s.
45. The composition of embodiment 44, wherein each nucleotide of the complementarity regions of the oligonucleotides is a non-natural nucleotide.
46. The composition of any one of embodiments 43 to 45, wherein the non-natural nucleotides are locked nucleic acid (LNA) nucleotides.
47. The composition of any one of embodiments 32 to 46, wherein the oligonucleotides of the oligonucleotide pool are not phosphorylated.
48. The composition of any one of embodiments 32 to 47, comprising 5' phosphorylated nucleic acids.
49. The composition of embodiment 48, wherein oligonucleotides of the oligonucleotide pool are hybridized to nucleic acids of the 5' phosphorylated nucleic acids having overhang regions that are complementary in sequence and have corresponding lengths with respect to the complementarity regions of the oligonucleotides.
50. The composition of embodiment 48 or embodiment 49, wherein the 5' phosphorylated nucleic acids are 5' phosphorylated deoxyribonucleic acids (DNAs).
51. The composition of embodiment 50, wherein the 5' phosphorylated DNAs are 5' phosphorylated genomic DNAs.
52. The composition of embodiment 48 or embodiment 49, wherein the 5' phosphorylated nucleic acids are 5' phosphorylated ribonucleic acids (RNAs).
53. The composition of any one of embodiment 48 to 52, wherein the 5' phosphorylated nucleic acids are prepared from a nucleic acid sample obtained from an animal.
54. The composition of embodiment 53, wherein the animal is an extinct animal.
55. The composition of embodiment 53 or embodiment 54, wherein the animal is a mammal.
56. The composition of embodiment 55, wherein the animal is from the genus *Homo*.
57. The composition of any one of embodiments 48 to 56, wherein the 5' phosphorylated nucleic acids are produced from cell-free nucleic acids.
58. The composition of embodiment 57, wherein the cell-free nucleic acids are obtained from a body fluid sample selected from the group consisting of: whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion, and stool.
59. The composition of embodiment 57 or embodiment 58, wherein the cell-free nucleic acids are cell-free fetal DNAs.
60. The composition of embodiment 57 or embodiment 58, wherein the cell-free nucleic acids are circulating tumor DNAs.
61. A kit, comprising:
  the composition of any one of embodiments 32 to 47; and
  instructions for using the composition to produce a nucleic acid library.
62. The kit of embodiment 61, further comprising a kinase adapted to 5' phosphorylate nucleic acids of a nucleic acid sample.
63. The kit of embodiment 62, wherein the kinase is a polynucleotide kinase (PNK).
64. The kit of any one of embodiments 61 to 63, further comprising a DNA ligase.
A1. A method for producing a nucleic acid library, comprising:
  combining:
    a nucleic acid composition comprising target nucleic acids, wherein some or all of the target nucleic acids comprise an overhang; and
    an oligonucleotide pool comprising oligonucleotides, wherein:
      some or all of the oligonucleotides comprise (i) a complementarity region capable of hybridizing to an overhang in a target nucleic acid, and (ii) a complementarity region identification polynucleotide,
      the oligonucleotides in the pool comprising complementarity regions include complementarity regions of different lengths, and
      the complementarity region identification polynucleotide is specific to one or more features of the complementarity region, wherein the one or more features comprise length of the complementarity region;
  under conditions in which complementarity regions in the oligonucleotides hybridize to overhangs in the target nucleic acids having a corresponding length, thereby forming hybridization products for a nucleic acid library.

A1.1 The method of embodiment A1, wherein the one or more features of the complementarity region further comprise (i) a 5' overhang, (ii) a 3' overhang, (iii) a particular sequence, (iv) a combination of (i) and (iii), or (v) a combination of (ii) and (iii).

A1.2 The method of embodiment A1 or A1.1, wherein some of the target nucleic acids comprise no overhang.

A1.3 The method of embodiment A1, A1.1 or A1.2, wherein some of the oligonucleotides comprise no complementarity region and comprise an identification polynucleotide specific to no complementarity region.

A2. The method of any one of embodiments A1-A1.3, wherein the target nucleic acids comprising an overhang comprise a double-stranded portion and a single-stranded overhang.

A3. The method of any one of embodiments A1-A2, wherein each target nucleic acid comprising an overhang comprises an overhang at one end or an overhang at both ends.

A4. The method of any one of embodiments A1-A3, wherein an end, or both ends, of each target nucleic acid comprising an overhang independently comprises a 5' overhang or a 3' overhang.

A5. The method of any one of embodiments A1-A4, wherein the target nucleic acids are, or are produced from, ribonucleic acids (RNAs).

A5.1 The method of embodiment A5, wherein the RNAs are obtained from cells.

A6. The method of any one of embodiments A1-A4, wherein the target nucleic acids are, or are produced from, deoxyribonucleic acids (DNAs).

A7. The method of embodiment A6, wherein the DNAs are obtained from cells.

A8. The method of embodiment A7, wherein the DNAs are, or are produced from, genomic DNAs.

A9. The method of any one of embodiments A1-A8, wherein the target nucleic acids are obtained from a sample from an animal.

A10. The method of embodiment A9, wherein the animal is an extinct animal.

A11. The method of embodiment A9 or A10, wherein the animal is a mammal.

A12. The method of embodiment A11, wherein the animal is from the genus *Homo*.

A13. The method of any one of embodiments A1-A5, A6, and A9-A12, wherein the target nucleic acids are, or are produced from, cell-free nucleic acids.

A14. The method of embodiment A13, wherein the cell-free nucleic acids are obtained from a body fluid sample chosen from whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion and stool.

A15. The method of embodiment A13 or A14, wherein the cell-free nucleic acids comprise cell-free fetal DNAs.

A16. The method of embodiment A13 or A14, wherein the cell-free nucleic acids comprise circulating cancer DNAs.

A17. The method of embodiment A16, wherein the cell-free nucleic acids comprise circulating tumor DNAs.

A18. The method of embodiment A13 or A14, wherein the cell-free nucleic acids comprise host and non-host DNAs.

A19. The method of embodiment A18, wherein the non-host DNAs are from an infectious agent.

A20. The method of embodiment A18, wherein the non-host DNAs are from a transplant.

A21. The method of any one of embodiments A1-A20, wherein overhangs in target nucleic acids are native overhangs.

A22. The method of any one of embodiments A1-A21, wherein the target nucleic acids are not modified in length prior to combining with the pool.

A23. The method of any one of embodiments A1-A22, comprising preparing the nucleic acid composition, prior to combining the composition with the pool, by a process consisting essentially of isolating nucleic acid from a sample, thereby generating the nucleic acid composition.

A24. The method of any one of embodiments A1-A22, comprising preparing the nucleic acid composition, prior to combining the nucleic acid composition with the pool, by a process consisting essentially of:
    isolating nucleic acid from a sample, thereby generating isolated nucleic acid; and
    modifying one or both ends of the isolated nucleic acid with a phosphate moiety or chemically reactive moiety, thereby generating the nucleic acid composition.

A25. The method of any one of embodiments A1-A24, wherein the target nucleic acids are in solution when combined with the pool.

A26. The method of any one of embodiments A1-A25, wherein target nucleic acids are not in a fixed cell sample.

A27. The method of any one of embodiments A1-A25, wherein target nucleic acids are not in a fixed tissue sample.

B1. The method of any one of embodiments A1-A27, wherein the oligonucleotide pool comprises oligonucleotides that comprise an overhang.

B2. The method of embodiment B1, wherein all oligonucleotides in the pool comprise an overhang.

B3. The method of embodiment B1 or B2, wherein the oligonucleotides that comprise an overhang comprise a double-stranded portion and a single-stranded overhang.

B4. The method of any one of embodiments B1-B3, wherein each of the oligonucleotides comprising an overhang comprise an overhang at one end or an overhang at both ends.

B5. The method of any one of embodiments B1-B4, wherein an end, or both ends, of each of the oligonucleotides comprising an overhang independently comprise a 5' overhang or a 3' overhang.

B5.1 The method of embodiment B5, wherein at an end, the overhang comprises the complementarity region.

B5.2 The method of embodiment B5, wherein the complementarity region identification polynucleotide is specific to whether the overhang comprising the complementarity region is a 5' overhang or a 3' overhang.

B6. The method of any one of embodiments B1-B5.2, wherein:
    the oligonucleotide pool comprises oligonucleotides comprising a first strand and a second strand; and
    the first strand comprises a first polynucleotide and the second strand comprises a second polynucleotide complementary to the first polynucleotide.

B6.1 The method of any one of embodiments B1-B5.2, wherein:
    the oligonucleotide pool comprises oligonucleotides each consisting essentially of a first strand and a second strand; and
    the first strand comprises a first polynucleotide and the second strand comprises a second polynucleotide complementary to the first polynucleotide.

B7. The method of any one of embodiments B1-B5.2, wherein:
    the oligonucleotide pool comprises oligonucleotides comprising one strand capable of adopting a hairpin structure; and the one strand comprises a first polynucleotide and a second polynucleotide, wherein a portion of the first polynucleotide is complementary to a portion of the second polynucleotide.

B7.1 The method of any one of embodiments B1-B5.2, wherein:

the oligonucleotide pool comprises oligonucleotides each consisting essentially of one strand capable of adopting a hairpin structure; and the oligonucleotides comprise a first polynucleotide and a second polynucleotide, wherein a portion of the first polynucleotide is complementary to a portion of the second polynucleotide.

B8. The method of any one of embodiments B1-B7.1, wherein the pool comprises oligonucleotides comprising an overhang of three or more nucleotide bases.

B9. The method of any one of embodiments B1-B8, wherein the oligonucleotides in the pool comprise overhangs that are 1, 2, 3, 4, 5, 6, 7, 8, 9, 10, 11, 12, 13, 14, 15, 16, 17, 18, 19 or 20 nucleotides in length, or combination thereof.

B10. The method of any one of embodiments B1-B9, wherein the pool comprises:

a subset of oligonucleotides that comprise a complementarity region that hybridizes to a 5' overhang of 1 nucleotide in length in a target nucleic acid;

a subset of oligonucleotides that comprise a complementarity region that hybridizes to a 5' overhang of 2 nucleotides in length in a target nucleic acid;

a subset of oligonucleotides that comprise a complementarity region that hybridizes to a 5' overhang of 3 nucleotides in length in a target nucleic acid;

a subset of oligonucleotides that comprise a complementarity region that hybridizes to a 5' overhang of 4 nucleotides in length in a target nucleic acid;

a subset of oligonucleotides that comprise a complementarity region that hybridizes to a 5' overhang of 5 nucleotides in length in a target nucleic acid;

a subset of oligonucleotides that comprise a complementarity region that hybridizes to a 5' overhang of 6 nucleotides in length in a target nucleic acid;

a subset of oligonucleotides that comprise a complementarity region that hybridizes to a 5' overhang of 7 nucleotides in length in a target nucleic acid;

a subset of oligonucleotides that comprise a complementarity region that hybridizes to a 5' overhang of 8 nucleotides in length in a target nucleic acid;

a subset of oligonucleotides that comprise a complementarity region that hybridizes to a 5' overhang of 9 nucleotides in length in a target nucleic acid;

a subset of oligonucleotides that comprise a complementarity region that hybridizes to a 5' overhang of 10 nucleotides in length in a target nucleic acid;

a subset of oligonucleotides that comprise a complementarity region that hybridizes to a 5' overhang of 11 nucleotides in length in a target nucleic acid;

a subset of oligonucleotides that comprise a complementarity region that hybridizes to a 5' overhang of 12 nucleotides in length in a target nucleic acid;

a subset of oligonucleotides that comprise a complementarity region that hybridizes to a 5' overhang of 13 nucleotides in length in a target nucleic acid;

a subset of oligonucleotides that comprise a complementarity region that hybridizes to a 5' overhang of 14 nucleotides in length in a target nucleic acid;

a subset of oligonucleotides that comprise a complementarity region that hybridizes to a 5' overhang of 15 nucleotides in length in a target nucleic acid; or combination thereof.

B11. The method of any one of embodiments B1-B10, wherein the pool comprises:

a subset of oligonucleotides that comprise (i) a complementarity region that hybridizes to a 5' overhang of 1 nucleotide in length in a target nucleic acid, and (ii) a complementarity region identification polynucleotide specific to complementarity regions that hybridize to 5' overhangs of 1 nucleotide in length in the target nucleic acids;

a subset of oligonucleotides that comprise (i) a complementarity region that hybridizes to a 5' overhang of 2 nucleotides in length in a target nucleic acid, and (ii) a complementarity region identification polynucleotide specific to complementarity regions that hybridize to 5' overhangs of 2 nucleotides in length in the target nucleic acids;

a subset of oligonucleotides that comprise (i) a complementarity region that hybridizes to a 5' overhang of 3 nucleotides in length in a target nucleic acid, and (ii) a complementarity region identification polynucleotide specific to complementarity regions that hybridize to 5' overhangs of 3 nucleotides in length in the target nucleic acids;

a subset of oligonucleotides that comprise (i) a complementarity region that hybridizes to a 5' overhang of 4 nucleotides in length in a target nucleic acid, and (ii) a complementarity region identification polynucleotide specific to complementarity regions that hybridize to 5' overhangs of 4 nucleotides in length in the target nucleic acids;

a subset of oligonucleotides that comprise (i) a complementarity region that hybridizes to a 5' overhang of 5 nucleotides in length in a target nucleic acid, and (ii) a complementarity region identification polynucleotide specific to complementarity regions that hybridize to 5' overhangs of 5 nucleotides in length in the target nucleic acids;

a subset of oligonucleotides that comprise (i) a complementarity region that hybridizes to a 5' overhang of 6 nucleotides in length in a target nucleic acid, and (ii) a complementarity region identification polynucleotide specific to complementarity regions that hybridize to 5' overhangs of 6 nucleotides in length in the target nucleic acids;

a subset of oligonucleotides that comprise (i) a complementarity region that hybridizes to a 5' overhang of 7 nucleotides in length in a target nucleic acid, and (ii) a complementarity region identification polynucleotide specific to complementarity regions that hybridize to 5' overhangs of 7 nucleotides in length in the target nucleic acids;

a subset of oligonucleotides that comprise (i) a complementarity region that hybridizes to a 5' overhang of 8 nucleotides in length in a target nucleic acid, and (ii) a complementarity region identification polynucleotide specific to complementarity regions that hybridize to 5' overhangs of 8 nucleotides in length in the target nucleic acids;

a subset of oligonucleotides that comprise (i) a complementarity region that hybridizes to a 5' overhang of 9 nucleotides in length in a target nucleic acid, and (ii) a complementarity region identification polynucleotide specific to complementarity regions that hybridize to 5' overhangs of 9 nucleotides in length in the target nucleic acids;

a subset of oligonucleotides that comprise (i) a complementarity region that hybridizes to a 5' overhang of 10 nucleotides in length in a target nucleic acid, and (ii) a complementarity region identification polynucleotide specific to complementarity regions that hybridize to 5' overhangs of 10 nucleotides in length in the target nucleic acids;

a subset of oligonucleotides that comprise (i) a complementarity region that hybridizes to a 5' overhang of 11 nucleotides in length in a target nucleic acid, and (ii) a complementarity region identification polynucleotide specific to complementarity regions that hybridize to 5' overhangs of 11 nucleotides in length in the target nucleic acids;

a subset of oligonucleotides that comprise (i) a complementarity region that hybridizes to a 5' overhang of 12 nucleotides in length in a target nucleic acid, and (ii) a complementarity region identification polynucleotide specific to complementarity regions that hybridize to 5' overhangs of 12 nucleotides in length in the target nucleic acids;

a subset of oligonucleotides that comprise (i) a complementarity region that hybridizes to a 5' overhang of 13 nucleotides in length in a target nucleic acid, and (ii) a complementarity region identification polynucleotide specific to complementarity regions that hybridize to 5' overhangs of 13 nucleotides in length in the target nucleic acids;

a subset of oligonucleotides that comprise (i) a complementarity region that hybridizes to a 5' overhang of 14 nucleotides in length in a target nucleic acid, and (ii) a complementarity region identification polynucleotide specific to complementarity regions that hybridize to 5' overhangs of 14 nucleotides in length in the target nucleic acids; and a subset of oligonucleotides that comprise (i) a complementarity region that hybridizes to a 5' overhang of 15 nucleotides in length in a target nucleic acid, and (ii) a complementarity region identification polynucleotide specific to complementarity regions that hybridize to 5' overhangs of 15 nucleotides in length in the target nucleic acids; or portion thereof.

B12. The method of any one of embodiments B1-B11, wherein the pool comprises:

a subset of oligonucleotides that comprise a complementarity region that hybridizes to a 3' overhang of 1 nucleotide in length in a target nucleic acid;

a subset of oligonucleotides that comprise a complementarity region that hybridizes to a 3' overhang of 2 nucleotides in length in a target nucleic acid;

a subset of oligonucleotides that comprise a complementarity region that hybridizes to a 3' overhang of 3 nucleotides in length in a target nucleic acid;

a subset of oligonucleotides that comprise a complementarity region that hybridizes to a 3' overhang of 4 nucleotides in length in a target nucleic acid;

a subset of oligonucleotides that comprise a complementarity region that hybridizes to a 3' overhang of 5 nucleotides in length in a target nucleic acid;

a subset of oligonucleotides that comprise a complementarity region that hybridizes to a 3' overhang of 6 nucleotides in length in a target nucleic acid;

a subset of oligonucleotides that comprise a complementarity region that hybridizes to a 3' overhang of 7 nucleotides in length in a target nucleic acid;

a subset of oligonucleotides that comprise a complementarity region that hybridizes to a 3' overhang of 8 nucleotides in length in a target nucleic acid;

a subset of oligonucleotides that comprise a complementarity region that hybridizes to a 3' overhang of 9 nucleotides in length in a target nucleic acid;

a subset of oligonucleotides that comprise a complementarity region that hybridizes to a 3' overhang of 10 nucleotides in length in a target nucleic acid;

a subset of oligonucleotides that comprise a complementarity region that hybridizes to a 3' overhang of 11 nucleotides in length in a target nucleic acid;

a subset of oligonucleotides that comprise a complementarity region that hybridizes to a 3' overhang of 12 nucleotides in length in a target nucleic acid;

a subset of oligonucleotides that comprise a complementarity region that hybridizes to a 3' overhang of 13 nucleotides in length in a target nucleic acid;

a subset of oligonucleotides that comprise a complementarity region that hybridizes to a 3' overhang of 14 nucleotides in length in a target nucleic acid;

a subset of oligonucleotides that comprise a complementarity region that hybridizes to a 3' overhang of 15 nucleotides in length in a target nucleic acid; or combination thereof.

B13. The method of any one of embodiments B1-B12, wherein the pool comprises:

a subset of oligonucleotides that comprise (i) a complementarity region that hybridizes to a 3' overhang of 1 nucleotide in length in a target nucleic acid, and (ii) a complementarity region identification polynucleotide specific to complementarity regions that hybridize to 3' overhangs of 1 nucleotide in length in the target nucleic acids;

a subset of oligonucleotides that comprise (i) a complementarity region that hybridizes to a 3' overhang of 2 nucleotides in length in a target nucleic acid, and (ii) a complementarity region identification polynucleotide specific to complementarity regions that hybridize to 3' overhangs of 2 nucleotides in length in the target nucleic acids;

a subset of oligonucleotides that comprise (i) a complementarity region that hybridizes to a 3' overhang of 3 nucleotides in length in a target nucleic acid, and (ii) a complementarity region identification polynucleotide specific to complementarity regions that hybridize to 3' overhangs of 3 nucleotides in length in the target nucleic acids;

a subset of oligonucleotides that comprise (i) a complementarity region that hybridizes to a 3' overhang of 4 nucleotides in length in a target nucleic acid, and (ii) a complementarity region identification polynucleotide specific to complementarity regions that hybridize to 3' overhangs of 4 nucleotides in length in the target nucleic acids;

a subset of oligonucleotides that comprise (i) a complementarity region that hybridizes to a 3' overhang of 5 nucleotides in length in a target nucleic acid, and (ii) a complementarity region identification polynucleotide specific to complementarity regions that hybridize to 3' overhangs of 5 nucleotides in length in the target nucleic acids;

a subset of oligonucleotides that comprise (i) a complementarity region that hybridizes to a 3' overhang of 6 nucleotides in length in a target nucleic acid, and (ii) a complementarity region identification polynucleotide specific to complementarity regions that hybridize to 3' overhangs of 6 nucleotides in length in the target nucleic acids;

a subset of oligonucleotides that comprise (i) a complementarity region that hybridizes to a 3' overhang of 7 nucleotides in length in a target nucleic acid, and (ii) a complementarity region identification polynucleotide specific to complementarity regions that hybridize to 3' overhangs of 7 nucleotides in length in the target nucleic acids;

a subset of oligonucleotides that comprise (i) a complementarity region that hybridizes to a 3' overhang of 8 nucleotides in length in a target nucleic acid, and (ii) a complementarity region identification polynucleotide specific to complementarity regions that hybridize to 3' overhangs of 8 nucleotides in length in the target nucleic acids;

a subset of oligonucleotides that comprise (i) a complementarity region that hybridizes to a 3' overhang of 9 nucleotides in length in a target nucleic acid, and (ii) a complementarity region identification polynucleotide specific to complementarity regions that hybridize to 3' overhangs of 9 nucleotides in length in the target nucleic acids;

a subset of oligonucleotides that comprise (i) a complementarity region that hybridizes to a 3' overhang of 10 nucleotides in length in a target nucleic acid, and (ii) a complementarity region identification polynucleotide specific to complementarity regions that hybridize to 3' overhangs of 10 nucleotides in length in the target nucleic acids;

a subset of oligonucleotides that comprise (i) a complementarity region that hybridizes to a 3' overhang of 11 nucleotides in length in a target nucleic acid, and (ii) a complementarity region identification polynucleotide specific to complementarity regions that hybridize to 3' overhangs of 11 nucleotides in length in the target nucleic acids;

a subset of oligonucleotides that comprise (i) a complementarity region that hybridizes to a 3' overhang of 12 nucleotides in length in a target nucleic acid, and (ii) a complementarity region identification polynucleotide specific to complementarity regions that hybridize to 3' overhangs of 12 nucleotides in length in the target nucleic acids;

a subset of oligonucleotides that comprise (i) a complementarity region that hybridizes to a 3' overhang of 13 nucleotides in length in a target nucleic acid, and (ii) a complementarity region identification polynucleotide specific to complementarity regions that hybridize to 3' overhangs of 13 nucleotides in length in the target nucleic acids;

a subset of oligonucleotides that comprise (i) a complementarity region that hybridizes to a 3' overhang of 14 nucleotides in length in a target nucleic acid, and (ii) a complementarity region identification polynucleotide specific to complementarity regions that hybridize to 3' overhangs of 14 nucleotides in length in the target nucleic acids; and a subset of oligonucleotides that comprise (i) a complementarity region that hybridizes to a 3' overhang of 15 nucleotides in length in a target nucleic acid, and (ii) a complementarity region identification polynucleotide specific to complementarity regions that hybridize to 3' overhangs of 15 nucleotides in length in the target nucleic acids; or portion thereof.

B14. The method of any one of embodiments B1-B13, wherein overhangs in the oligonucleotides of the pool comprise nucleotides capable of specific base pairing to bases in the target nucleic acids B15. The method of embodiment B14, wherein overhangs in the oligonucleotides of the pool comprise nucleotides comprising two or more of adenine, guanine, cytosine, thymidine and uracil.

B16. The method of embodiment B14 or embodiment B15, wherein the oligonucleotide pool comprises oligonucleotides that comprise different overhang polynucleotides for a particular overhang length.

B17. The method of embodiment B16, wherein the oligonucleotide pool comprises oligonucleotides that comprise all possible overhang polynucleotide combinations for a particular overhang length.

B18. The method of embodiment B17, wherein the oligonucleotide pool comprises oligonucleotides that comprise all possible overhang polynucleotide combinations for each overhang length.

B19. The method of any one of embodiments B14-B18, wherein the overhang polynucleotides in the oligonucleotides of the pool are random.

B20. The method of any one of embodiments B1-B19, wherein overhangs in the oligonucleotides of the pool comprise nucleotides capable of non-specific base pairing to bases in the target nucleic acids.

B21. The method of embodiment B20, wherein overhangs in the oligonucleotides of the pool comprise nitroindole, deoxyinosine or combination thereof.

B22. The method of embodiment B21, wherein the nitroindole is 5-nitroindole.

B23. The method of embodiment B21 or embodiment B22, wherein the deoxyinosine is 2-deoxyinosine.

B24. The method of any one of embodiments B1-B23, wherein an end of an oligonucleotide is capable of being covalently linked to an end of a target nucleic acid to which the oligonucleotide is hybridized in the hybridization products.

B25. The method of embodiment B24, wherein the 3' end of an oligonucleotide strand is capable of being covalently linked to the 5' end of a strand in the target nucleic acid to which the oligonucleotide is hybridized in a hybridization product.

B26. The method of any one of embodiments B1-B25, wherein a region of the oligonucleotides adjacent to the complementarity region comprises all or a portion of the complementarity region identification polynucleotide.

B27. The method of embodiment B26, wherein the oligonucleotides in the pool comprise an opposing overhang at the end opposite the end having an overhang that hybridizes to a target nucleic acid.

B28. The method of embodiment B27, comprising, after the combining, filling in the opposing overhang.

B29. The method of any one of embodiments B1-B28, wherein the oligonucleotides of the oligonucleotide pool comprise a portion other than the complementarity region and the complementarity region identification polynucleotide.

B30. The method of embodiment B29, wherein a portion other than the complementarity region and the complementarity region identification polynucleotide comprises a nucleic acid binding domain.

B31. The method of embodiment B30, wherein the nucleic acid binding domain is a primer binding domain.

B32. The method of embodiment B30 or B31, wherein a portion other than the complementarity region and the complementarity region identification polynucleotide comprises all or a portion of a sequencing adapter.

B33. The method of any one of embodiments B1-B32, wherein the oligonucleotides of the oligonucleotide pool comprise one or more non-natural nucleotides.

B34. The method of embodiment B33, wherein one or more nucleotides of the complementarity regions of the oligonucleotides are non-natural nucleotides.

B35. The method of embodiment B34, wherein each nucleotide of the complementarity regions of the oligonucleotides is a non-natural nucleotide.

B36. The method of any one of embodiments B33-B35, wherein the non-natural nucleotides are locked nucleic acid (LNA) nucleotides.

B37. The method of any one of embodiments B1-B36, wherein the oligonucleotides comprise one or more backbone modifications.

C1. The method of any one of embodiments A1-A27 and B1-B37, comprising exposing the hybridization products to conditions under which an end of the target nucleic acid is joined to an end of the oligonucleotide to which it is hybridized.

C2. The method of any one of embodiments A1-A27, B1-B37 and C1, wherein the target nucleic acids in the composition are 5' phosphorylated.

C3. The method of any one of embodiments A1-A27, B1-B37 and C1 or C2, wherein oligonucleotides of the oligonucleotide pool are not phosphorylated.

C4. The method of any one of embodiments A1-A27, B1-B37 and C1-C3, wherein oligonucleotides of the oligonucleotide pool are phosphorylated.

C5. The method of any one of embodiments A1-A27, B1-B37 and C1-C4, comprising, prior to combining the nucleic acid composition with the oligonucleotide pool, contacting the target nucleic acids in the composition with an agent comprising a phosphoryl transfer activity under conditions in which a 5' phosphate is added to a 5' end of target nucleic acids.

C6. The method of any one of embodiments A1-A27, B1-B37 and C1-C4, comprising, prior to combining the nucleic acid composition with the oligonucleotide pool, contacting the target nucleic acids in the composition with no agent comprising a phosphoryl transfer activity.

C7. The method of any one of embodiments A1-A27, B1-B37 and C1-C6, comprising, prior to combining the nucleic acid composition with the oligonucleotide pool, contacting the oligonucleotides in the pool with no agent comprising a phosphoryl transfer activity.

C8. The method of any one of embodiments C1-C7, comprising contacting the hybridization products with an agent comprising a ligase activity under conditions in which an end of a target nucleic acid is covalently linked to an end of the oligonucleotide to which the target nucleic acid is hybridized.

C9. The method of embodiment C8, wherein the hybridization products are contacted with a first agent comprising a first ligase activity and a second agent comprising a second ligase activity different than the first ligase activity.

C10. The method of embodiment C9, wherein the first ligase activity and the second ligase activity independently are chosen from blunt-end ligase activity, nick-sealing ligase activity, sticky end ligase activity, circularization ligase activity, and cohesive end ligase activity.

C11. The method of any one of embodiments A1-A27, B1-B37 and C1, wherein:
an end of each of the oligonucleotides comprises a first chemically reactive moiety and an end of each of the target nucleic acids includes a second chemically reactive moiety; and
the first chemically reactive moiety is capable of reacting with the second chemically reactive moiety and forming a covalent bond between an oligonucleotide and a target nucleic acid to which the oligonucleotide is hybridized.

C12. The method of embodiment C11, comprising, prior to combining the nucleic acid composition with the oligonucleotide pool, contacting the target nucleic acids in the composition with one or more chemical agents under conditions in which the second chemically reactive moiety is incorporated at an end of each of the target nucleic acids.

C13. The method of embodiment C11 or C12, comprising exposing the hybridization products with one or more chemical agents to conditions in which the first chemically reactive moiety reacts with the second chemically reactive moiety forming a covalent bond between an oligonucleotide and a target nucleic acid to which the oligonucleotide is hybridized.

C14. The method of any one of embodiments C11-C13, wherein the first chemically reactive moiety is capable of reacting with the second chemically reactive moiety to form a 1,2,3-triazole between the oligonucleotide and the target nucleic acid to which the oligonucleotide is hybridized.

C15. The method of any one of embodiments C11-C14, wherein the first chemically reactive moiety is capable of reacting with the second chemically reactive moiety under conditions comprising copper.

C16. The method of any one of embodiments C11-C15, wherein the first chemically reactive moiety is chosen from an azide-containing moiety and 5-octadiynyl deoxyuracil, and the second chemically reactive moiety is independently chosen from an azide-containing moiety, hexynyl and 5-octadiynyl deoxyuracil.

C17. The method of embodiment C16, wherein the azide-containing moiety is N-hydroxysuccinimide (NHS) ester-azide.

D1. The method of any one of embodiments A1-A27, B7-B37 and C1-C17, wherein the oligonucleotides comprise one strand capable of adopting a hairpin structure, wherein the one strand comprises a first polynucleotide, a second polynucleotide, and one or more cleavage sites capable of being cleaved under cleavage conditions.

D1.1 The method of any one of embodiments A1-A27, B7-B37 and C1-C17, wherein the oligonucleotides consist essentially of one strand capable of adopting a hairpin structure, wherein the one strand comprises a first polynucleotide, a second polynucleotide, and one or more cleavage sites capable of being cleaved under cleavage conditions.

D1.2 The method of embodiment D1 or D1.1, wherein the first polynucleotide comprises a first region that is complementary to a first region in the second polynucleotide, and the first polynucleotide comprises a second region that is not complementary to a second region in the second polynucleotide.

D2. The method of embodiment D1, D1.1 or D1.2, wherein the one or more cleavage sites are located between the first polynucleotide and the second polynucleotide.

D3. The method of any one of embodiments D1-D2, wherein the one or more cleavage sites comprise uracil and/or deoxyuridine nucleotides.

D4. The method of any one of embodiments D1-D2, wherein the one or more cleavage sites comprise a diol.

D4.1 The method of embodiment D4, wherein the diol is a vicinal diol incorporated in a 5' to 5' linkage.

D5. The method of any one of embodiments D1-D2, wherein the one or more cleavage sites comprises a restriction enzyme recognition site.

D5.1 The method of embodiment D5, wherein the restriction enzyme recognition site is a rare-cutter restriction enzyme recognition site.

D6. The method of any one of embodiments D1-D5.1, comprising, after the combining, exposing the one or more cleavage sites to cleavage conditions, thereby cleaving the oligonucleotides.

D7. The method of any one of embodiments D1-D6, wherein the oligonucleotides comprise in a 5' to 3' orientation:
a 5' complementarity region identification polynucleotide,
the first polynucleotide,
the one or more cleavage sites,
the second polynucleotide,
a 3' complementarity region identification polynucleotide complementary to the 5' complementarity region identification polynucleotide, and
the complementarity region.

D8. The method of any one of embodiments D1-D6, wherein the oligonucleotides comprise in a 5' to 3' orientation:
the complementarity region,
a 5' complementarity region identification polynucleotide,
the first polynucleotide,
the one or more cleavage sites,
the second polynucleotide, and
a 3' complementarity region identification polynucleotide complementary to the 5' complementarity region identification polynucleotide.

D9. The method of any one of embodiments D1-D6, wherein the oligonucleotides comprise a mixture of:
(i) oligonucleotides comprising in a 5' to 3' orientation:
a 5' complementarity region identification polynucleotide,
the first polynucleotide,
the one or more cleavage sites,
the second polynucleotide,
a 3' complementarity region identification polynucleotide complementary to the 5' complementarity region identification polynucleotide, and
the complementarity region; and
(ii) oligonucleotides comprising in a 5' to 3' orientation:
the complementarity region,
a 5' complementarity region identification polynucleotide,
the first polynucleotide,
the one or more cleavage sites,
the second polynucleotide, and
a 3' complementarity region identification polynucleotide complementary to the 5' complementarity region identification polynucleotide.

E1. The method of any one of embodiments A1-A27, B1-B37, C1-C17 and D1-D9, comprising, after the combining, contacting the complementarity region identification polynucleotide with a binding agent comprising a binding polynucleotide complementary to the complementarity region identification polynucleotide under conditions in which the binding polynucleotide and the complementarity region identification polynucleotide hybridize, thereby generating binding complexes and nucleic acid not bound to the binding agent.

E2. The method of embodiment E1, wherein the binding agent comprises a solid phase.

E3. The method of embodiment E1, wherein the binding agent comprises a linker, and the linker is linked, or is capable of being linked, to a solid phase.

E4. The method of any one of embodiments E1-E3, comprising separating the binding complexes from the nucleic acid not bound to the binding agent.

F1. A method for sequencing target nucleic acids, comprising:
performing a method of any one of embodiments A1-A27, B1-B37, C1-C17, D1-D9 and E1-E4, thereby generating a nucleic acid library;
exposing the nucleic acid library to a sequencing process.

F2. The method of embodiment F1, wherein a portion other than the complementarity region and the complementarity region identification polynucleotide in the oligonucleotides comprises all or a portion of a sequencing adapter.

F3. The method of embodiment F1 or F2, consisting essentially of:
(i) combining the nucleic acid composition with the oligonucleotide pool, thereby forming hybridization products;
(ii) joining target nucleic acids to the oligonucleotides in the hybridization products, thereby generating complexes;
(iii) modifying oligonucleotides in the complexes, thereby generating a nucleic acid library; and
(iv) exposing the nucleic acid library to a sequencing process.

F4. The method of embodiment F1 or F2, consisting essentially of:
(i) combining the nucleic acid composition with the oligonucleotide pool, thereby forming hybridization products;
(ii) joining target nucleic acids to the oligonucleotides in the hybridization products, thereby generating complexes;
(iii) associating complexes with one or more binding agents that specifically hybridize to a particular complementarity region identification polynucleotide, thereby generating enriched complexes;
(iv) modifying oligonucleotides in the enriched complexes, thereby generating a nucleic acid library; and
(v) exposing the nucleic acid library to a sequencing process.

F5. The method of embodiment F3 or F4, wherein modifying the oligonucleotides comprises cleaving one or more cleavage sites in the oligonucleotides.

F6. The method of embodiment F3 or F4, wherein modifying the oligonucleotides comprises filling in overhangs in the oligonucleotides opposite to the overhangs in the oligonucleotide that interact with overhangs in the target nucleic acids.

F7. The method of any one of embodiments F1-F6, wherein the sequencing process is a highly multiplexed sequencing process.

F8. The method of any one of embodiments F1-F7, wherein the sequencing process generates sequencing reads.

F9. The method of embodiment F8, comprising determining the sequence of an overhang for the target nucleic acids based on the sequencing reads.

F10. The method of embodiment F8 or F9, comprising determining a sequence of a complementarity region identification polynucleotide based on the sequencing reads.

F11. The method of any one of embodiments F8-F10, comprising determining lengths of the overhangs for the target nucleic acids.

G1. A method for analyzing a particular overhang in a nucleic acid composition, comprising:
sequencing nucleic acids according to a method of any one of embodiments F1-F11; and
quantifying the amount of overhangs in target nucleic acids, thereby generating an overhang quantification.

G2. The method of embodiment G1, wherein the overhang quantification is for an overhang characterized as (i) a 5' overhang, (ii) a 3' overhang, (iii) a particular sequence, (iv) a particular length, or (v) a combination of two, three or four of (i), (ii), (iii) and (iv).

G3. The method of embodiment G1 or G2, wherein the overhang quantification is for an overhang characterized as (i) a 5' overhang or a 3' overhang, and (ii) a particular length.

G4. The method of any one of embodiments G1-G3, comprising identifying the source of target nucleic acids in the nucleic acid sample from which the target nucleic acid composition originated based on the overhang quantification.

G5. The method of any one of embodiments G1-G4, wherein the method is performed for a forensic analysis.

G6. The method of any one of embodiments G1-G4, wherein the method is performed for a diagnostic analysis.

H1. A composition, comprising an oligonucleotide pool comprising oligonucleotides, wherein:
some or all of the oligonucleotides comprise (i) a complementarity region capable of hybridizing to an overhang in a target nucleic acid of a nucleic acid composition, and (ii) a complementarity region identification polynucleotide, the oligonucleotides in the pool comprising complementarity regions include complementarity regions of different lengths, and the complementarity region identification polynucleotide is specific to one or more features of the complementarity region, wherein the one or more features comprise length of the complementarity region.

H1.1 The composition of embodiment H1, wherein the one or more features of the complementarity region further comprise (i) a 5' overhang, (ii) a 3' overhang, (iii) a particular sequence, (iv) a combination of (i) and (iii), or (v) a combination of (ii) and (iii).

H1.2 The composition of embodiment H1 or H1.1, wherein some of the oligonucleotides comprise no complementarity region and comprise an identification polynucleotide specific to no complementary region.

H2. The composition of any one of embodiments H1-H1.2, wherein the composition is present in a container.

H3. The composition of any one of embodiments H1-H2, wherein the composition is a liquid composition.

H4. The composition of any one of embodiments H1-H2, wherein the composition is a lyophilized composition.

H5. The composition of any one of embodiments H1-H4, wherein oligonucleotides of the oligonucleotide pool are hybridized to target nucleic acids in hybridization products.

H6. The composition of any one of embodiments H1-H5, wherein the oligonucleotide pool comprises oligonucleotides that comprise an overhang.

H7. The composition of any one of embodiments H1-H6, wherein all oligonucleotides in the pool comprise an overhang.

H8. The composition of embodiment H6 or H7, wherein the oligonucleotides that comprise an overhang comprise a double-stranded portion and a single-stranded overhang.

H9. The composition of any one of embodiments H6-H8, wherein each of the oligonucleotides comprising an overhang comprises an overhang at one end or an overhang at both ends.

H10. The composition of any one of embodiments H6-H9, wherein an end, or both ends, of each of the oligonucleotides comprising an overhang independently comprises a 5' overhang or a 3' overhang.

H10.1 The composition of embodiment H10, wherein at an end, the overhang comprises the complementarity region.

H10.2 The composition of embodiment H10.1, wherein the complementarity region identification polynucleotide is specific to whether the overhang comprising the complementarity region is a 5' overhang or a 3' overhang.

H11. The composition of any one of embodiments H6-H10.2, wherein:

the oligonucleotide pool comprises oligonucleotides each consisting essentially of a first strand and a second strand; and the first strand comprises a first polynucleotide and the second strand comprises a second polynucleotide complementary to the first polynucleotide.

H12. The composition of any one of embodiments H6-H10, wherein:

the oligonucleotide pool comprises oligonucleotides each consisting essentially of one strand capable of adopting a hairpin structure; and the oligonucleotides comprise a first polynucleotide and a second polynucleotide complementary to the first polynucleotide.

H13. The composition of any one of embodiments H6-H12, wherein the pool comprises oligonucleotides comprising an overhang of three or more nucleotide bases.

H14. The composition of any one of embodiments H6-H13, wherein the oligonucleotides in the pool comprise overhangs that are 1, 2, 3, 4, 5, 6, 7, 8, 9, 10, 11, 12, 13, 14, 15, 16, 17, 18, 19 or 20 nucleotides in length, or combination thereof.

H15. The composition of any one of embodiments H6-H14, wherein the pool comprises:

a subset of oligonucleotides that comprises a complementarity region that hybridizes to a 5' overhang of 1 nucleotide in length in a target nucleic acid;

a subset of oligonucleotides that comprises a complementarity region that hybridizes to a 5' overhang of 2 nucleotides in length in a target nucleic acid;

a subset of oligonucleotides that comprises a complementarity region that hybridizes to a 5' overhang of 3 nucleotides in length in a target nucleic acid;

a subset of oligonucleotides that comprises a complementarity region that hybridizes to a 5' overhang of 4 nucleotides in length in a target nucleic acid;

a subset of oligonucleotides that comprises a complementarity region that hybridizes to a 5' overhang of 5 nucleotides in length in a target nucleic acid;

a subset of oligonucleotides that comprises a complementarity region that hybridizes to a 5' overhang of 6 nucleotides in length in a target nucleic acid;

a subset of oligonucleotides that comprises a complementarity region that hybridizes to a 5' overhang of 7 nucleotides in length in a target nucleic acid;

a subset of oligonucleotides that comprises a complementarity region that hybridizes to a 5' overhang of 8 nucleotides in length in a target nucleic acid;

a subset of oligonucleotides that comprises a complementarity region that hybridizes to a 5' overhang of 9 nucleotides in length in a target nucleic acid;

a subset of oligonucleotides that comprises a complementarity region that hybridizes to a 5' overhang of 10 nucleotides in length in a target nucleic acid;

a subset of oligonucleotides that comprises a complementarity region that hybridizes to a 5' overhang of 11 nucleotides in length in a target nucleic acid;

a subset of oligonucleotides that comprises a complementarity region that hybridizes to a 5' overhang of 12 nucleotides in length in a target nucleic acid;

a subset of oligonucleotides that comprises a complementarity region that hybridizes to a 5' overhang of 13 nucleotides in length in a target nucleic acid;

a subset of oligonucleotides that comprises a complementarity region that hybridizes to a 5' overhang of 14 nucleotides in length in a target nucleic acid;

a subset of oligonucleotides that comprises a complementarity region that hybridizes to a 5' overhang of 15 nucleotides in length in a target nucleic acid; or combination thereof.

H16. The composition of any one of embodiments H6-H15, wherein the pool comprises:

a subset of oligonucleotides that comprise (i) a complementarity region that hybridizes to a 5' overhang of 1 nucleotide in length in a target nucleic acid, and (ii) a complementarity region identification polynucleotide specific to complementarity regions that hybridize to 5' overhangs of 1 nucleotide in length in the target nucleic acids;

a subset of oligonucleotides that comprise (i) a complementarity region that hybridizes to a 5' overhang of 2 nucleotides in length in a target nucleic acid, and (ii) a complementarity region identification polynucleotide specific to complementarity regions that hybridize to 5' overhangs of 2 nucleotides in length in the target nucleic acids;

a subset of oligonucleotides that comprise (i) a complementarity region that hybridizes to a 5' overhang of 3 nucleotides in length in a target nucleic acid, and (ii) a complementarity region identification polynucleotide specific to complementarity regions that hybridize to 5' overhangs of 3 nucleotides in length in the target nucleic acids;

a subset of oligonucleotides that comprise (i) a complementarity region that hybridizes to a 5' overhang of 4 nucleotides in length in a target nucleic acid, and (ii) a complementarity region identification polynucleotide specific to complementarity regions that hybridize to 5' overhangs of 4 nucleotides in length in the target nucleic acids;

a subset of oligonucleotides that comprise (i) a complementarity region that hybridizes to a 5' overhang of 5 nucleotides in length in a target nucleic acid, and (ii) a complementarity region identification polynucleotide specific to complementarity regions that hybridize to 5' overhangs of 5 nucleotides in length in the target nucleic acids;

a subset of oligonucleotides that comprise (i) a complementarity region that hybridizes to a 5' overhang of 6 nucleotides in length in a target nucleic acid, and (ii) a complementarity region identification polynucleotide specific to complementarity regions that hybridize to 5' overhangs of 6 nucleotides in length in the target nucleic acids;

a subset of oligonucleotides that comprise (i) a complementarity region that hybridizes to a 5' overhang of 7 nucleotides in length in a target nucleic acid, and (ii) a complementarity region identification polynucleotide specific to complementarity regions that hybridize to 5' overhangs of 7 nucleotides in length in the target nucleic acids;

a subset of oligonucleotides that comprise (i) a complementarity region that hybridizes to a 5' overhang of 8 nucleotides in length in a target nucleic acid, and (ii) a complementarity region identification polynucleotide specific to complementarity regions that hybridize to 5' overhangs of 8 nucleotides in length in the target nucleic acids;

a subset of oligonucleotides that comprise (i) a complementarity region that hybridizes to a 5' overhang of 9 nucleotides in length in a target nucleic acid, and (ii) a complementarity region identification polynucleotide specific to complementarity regions that hybridize to 5' overhangs of 9 nucleotides in length in the target nucleic acids;

a subset of oligonucleotides that comprise (i) a complementarity region that hybridizes to a 5' overhang of 10 nucleotides in length in a target nucleic acid, and (ii) a complementarity region identification polynucleotide specific to complementarity regions that hybridize to 5' overhangs of 10 nucleotides in length in the target nucleic acids;

a subset of oligonucleotides that comprise (i) a complementarity region that hybridizes to a 5' overhang of 11 nucleotides in length in a target nucleic acid, and (ii) a complementarity region identification polynucleotide specific to complementarity regions that hybridize to 5' overhangs of 11 nucleotides in length in the target nucleic acids;

a subset of oligonucleotides that comprise (i) a complementarity region that hybridizes to a 5' overhang of 12 nucleotides in length in a target nucleic acid, and (ii) a complementarity region identification polynucleotide specific to complementarity regions that hybridize to 5' overhangs of 12 nucleotides in length in the target nucleic acids;

a subset of oligonucleotides that comprise (i) a complementarity region that hybridizes to a 5' overhang of 13 nucleotides in length in a target nucleic acid, and (ii) a complementarity region identification polynucleotide specific to complementarity regions that hybridize to 5' overhangs of 13 nucleotides in length in the target nucleic acids;

a subset of oligonucleotides that comprise (i) a complementarity region that hybridizes to a 5' overhang of 14 nucleotides in length in a target nucleic acid, and (ii) a complementarity region identification polynucleotide specific to complementarity regions that hybridize to 5' overhangs of 14 nucleotides in length in the target nucleic acids; and a subset of oligonucleotides that comprise (i) a complementarity region that hybridizes to a 5' overhang of 15 nucleotides in length in a target nucleic acid, and (ii) a complementarity region identification polynucleotide specific to complementarity regions that hybridize to 5' overhangs of 15 nucleotides in length in the target nucleic acids; or portion thereof.

H17. The composition of any one of embodiments H6-H16, wherein the pool comprises:

a subset of oligonucleotides that comprises a complementarity region that hybridizes to a 3' overhang of 1 nucleotide in length in a target nucleic acid;

a subset of oligonucleotides that comprises a complementarity region that hybridizes to a 3' overhang of 2 nucleotides in length in a target nucleic acid;

a subset of oligonucleotides that comprises a complementarity region that hybridizes to a 3' overhang of 3 nucleotides in length in a target nucleic acid;

a subset of oligonucleotides that comprises a complementarity region that hybridizes to a 3' overhang of 4 nucleotides in length in a target nucleic acid;

a subset of oligonucleotides that comprises a complementarity region that hybridizes to a 3' overhang of 5 nucleotides in length in a target nucleic acid;

a subset of oligonucleotides that comprises a complementarity region that hybridizes to a 3' overhang of 6 nucleotides in length in a target nucleic acid;

a subset of oligonucleotides that comprises a complementarity region that hybridizes to a 3' overhang of 7 nucleotides in length in a target nucleic acid;

a subset of oligonucleotides that comprises a complementarity region that hybridizes to a 3' overhang of 8 nucleotides in length in a target nucleic acid;

a subset of oligonucleotides that comprises a complementarity region that hybridizes to a 3' overhang of 9 nucleotides in length in a target nucleic acid;

a subset of oligonucleotides that comprises a complementarity region that hybridizes to a 3' overhang of 10 nucleotides in length in a target nucleic acid;

a subset of oligonucleotides that comprises a complementarity region that hybridizes to a 3' overhang of 11 nucleotides in length in a target nucleic acid;

a subset of oligonucleotides that comprises a complementarity region that hybridizes to a 3' overhang of 12 nucleotides in length in a target nucleic acid;

a subset of oligonucleotides that comprises a complementarity region that hybridizes to a 3' overhang of 13 nucleotides in length in a target nucleic acid;

a subset of oligonucleotides that comprises a complementarity region that hybridizes to a 3' overhang of 14 nucleotides in length in a target nucleic acid;

a subset of oligonucleotides that comprises a complementarity region that hybridizes to a 3' overhang of 15 nucleotides in length in a target nucleic acid; or combination thereof.

H18. The composition of any one of embodiments H6-H17, wherein the pool comprises:

A subset of oligonucleotides that comprise (i) a complementarity region that hybridizes to a 3' overhang of 1 nucleotide in length in a target nucleic acid, and (ii) a complementarity region identification polynucleotide specific to complementarity regions that hybridize to 3' overhangs of 1 nucleotide in length in the target nucleic acids;

a subset of oligonucleotides that comprise (i) a complementarity region that hybridizes to a 3' overhang of 2 nucleotides in length in a target nucleic acid, and (ii) a complementarity region identification polynucleotide specific to complementarity regions that hybridize to 3' overhangs of 2 nucleotides in length in the target nucleic acids;

a subset of oligonucleotides that comprise (i) a complementarity region that hybridizes to a 3' overhang of 3 nucleotides in length in a target nucleic acid, and (ii) a complementarity region identification polynucleotide specific to complementarity regions that hybridize to 3' overhangs of 3 nucleotides in length in the target nucleic acids;

a subset of oligonucleotides that comprise (i) a complementarity region that hybridizes to a 3' overhang of 4 nucleotides in length in a target nucleic acid, and (ii) a complementarity region identification polynucleotide specific to complementarity regions that hybridize to 3' overhangs of 4 nucleotides in length in the target nucleic acids;

a subset of oligonucleotides that comprise (i) a complementarity region that hybridizes to a 3' overhang of 5 nucleotides in length in a target nucleic acid, and (ii) a complementarity region identification polynucleotide specific to complementarity regions that hybridize to 3' overhangs of 5 nucleotides in length in the target nucleic acids;

a subset of oligonucleotides that comprise (i) a complementarity region that hybridizes to a 3' overhang of 6 nucleotides in length in a target nucleic acid, and (ii) a complementarity region identification polynucleotide specific to complementarity regions that hybridize to 3' overhangs of 6 nucleotides in length in the target nucleic acids;

a subset of oligonucleotides that comprise (i) a complementarity region that hybridizes to a 3' overhang of 7 nucleotides in length in a target nucleic acid, and (ii) a complementarity region identification polynucleotide specific to complementarity regions that hybridize to 3' overhangs of 7 nucleotides in length in the target nucleic acids;

a subset of oligonucleotides that comprise (i) a complementarity region that hybridizes to a 3' overhang of 8 nucleotides in length in a target nucleic acid, and (ii) a complementarity region identification polynucleotide specific to complementarity regions that hybridize to 3' overhangs of 8 nucleotides in length in the target nucleic acids;

a subset of oligonucleotides that comprise (i) a complementarity region that hybridizes to a 3' overhang of 9 nucleotides in length in a target nucleic acid, and (ii) a complementarity region identification polynucleotide specific to complementarity regions that hybridize to 3' overhangs of 9 nucleotides in length in the target nucleic acids;

a subset of oligonucleotides that comprise (i) a complementarity region that hybridizes to a 3' overhang of 10 nucleotides in length in a target nucleic acid, and (ii) a complementarity region identification polynucleotide specific to complementarity regions that hybridize to 3' overhangs of 10 nucleotides in length in the target nucleic acids;

a subset of oligonucleotides that comprise (i) a complementarity region that hybridizes to a 3' overhang of 11 nucleotides in length in a target nucleic acid, and (ii) a complementarity region identification polynucleotide specific to complementarity regions that hybridize to 3' overhangs of 11 nucleotides in length in the target nucleic acids;

a subset of oligonucleotides that comprise (i) a complementarity region that hybridizes to a 3' overhang of 12 nucleotides in length in a target nucleic acid, and (ii) a complementarity region identification polynucleotide specific to complementarity regions that hybridize to 3' overhangs of 12 nucleotides in length in the target nucleic acids;

a subset of oligonucleotides that comprise (i) a complementarity region that hybridizes to a 3' overhang of 13 nucleotides in length in a target nucleic acid, and (ii) a complementarity region identification polynucleotide specific to complementarity regions that hybridize to 3' overhangs of 13 nucleotides in length in the target nucleic acids;

a subset of oligonucleotides that comprise (i) a complementarity region that hybridizes to a 3' overhang of 14 nucleotides in length in a target nucleic acid, and (ii) a complementarity region identification polynucleotide specific to complementarity regions that hybridize to 3' overhangs of 14 nucleotides in length in the target nucleic acids; and a subset of oligonucleotides that comprise (i) a complementarity region that hybridizes to a 3' overhang of 15 nucleotides in length in a target nucleic acid, and (ii) a complementarity region identification polynucleotide specific to complementarity regions that hybridize to 3' overhangs of 15 nucleotides in length in the target nucleic acids; or portion thereof.

H19. The composition of any one of embodiments H6-H18, wherein overhangs in the oligonucleotides of the pool comprise nucleotides capable of specific base pairing to bases in the target nucleic acids H20. The composition of embodiment H19, wherein overhangs in the oligonucleotides of the pool comprise nucleotides comprising two or more of adenine, guanine, cytosine, thymidine and uracil.

H21. The composition of embodiment H19 or H20, wherein the oligonucleotide pool comprises oligonucleotides that comprise different overhang polynucleotides for a particular overhang length.

H22. The composition of embodiment H21, wherein the oligonucleotide pool comprises oligonucleotides that comprise all possible overhang polynucleotide combinations for a particular overhang length.

H23. The composition of embodiment H22, wherein the oligonucleotide pool comprises oligonucleotides that comprise all possible overhang polynucleotide combinations for each overhang length.

H24. The composition of any one of embodiments H19-H23, wherein the overhang polynucleotides in the oligonucleotides of the pool are random.

H25. The composition of any one of embodiments H6-H24, wherein overhangs in the oligonucleotides of the pool comprise nucleotides capable of non-specific base pairing to bases in the target nucleic acids.

H26. The composition of any one of embodiments H6-H25, wherein overhangs in the oligonucleotides of the pool comprise nitroindole, deoxyinosine or combination thereof.

H27. The composition of embodiment H26, wherein the nitroindole is 5-nitroindole.

H28. The composition of embodiment H26 or H27, wherein the deoxyinosine is 2-deoxyinosine.

H29. The composition of any one of embodiments H6-H28, wherein an end of an oligonucleotide is capable of being covalently linked to an end of a target nucleic acid to which the oligonucleotide is hybridized in the hybridization products.

H30. The composition of any one of embodiments H6-H29, wherein the 3' end of an oligonucleotide strand is capable of being covalently linked to the 5' end of a strand in the target nucleic acid to which the oligonucleotide is hybridized in a hybridization product.

H31. The composition of any one of embodiments H6-H30, wherein a region of the oligonucleotides adjacent to the complementarity region comprises all or a portion of the complementarity region identification polynucleotide.

H32. The composition of embodiment H31, wherein the oligonucleotides in the pool comprise an opposing overhang at the end opposite the end having an overhang that hybridizes to a target nucleic acid.

H33. The composition of embodiment H32, comprising, after the combining, filling in the opposing overhang.

H34. The composition of any one of embodiments H6-H33, wherein the oligonucleotides of the oligonucleotide pool comprise a portion other than the complementarity region and the complementarity region identification polynucleotide.

H35. The composition of embodiment H34, wherein a portion other than the complementarity region and the complementarity region identification polynucleotide comprises a nucleic acid binding domain.

H36. The composition of embodiment H35, wherein the nucleic acid binding domain is a primer binding domain.

H37. The composition of embodiment H35 or H36, wherein a portion other than the complementarity region and the complementarity region identification polynucleotide comprises all or a portion of a sequencing adapter.

H38. The composition of any one of embodiments H6-H37, wherein the oligonucleotides of the oligonucleotide pool comprise one or more non-natural nucleotides.

H39. The composition of embodiment H38, wherein one or more nucleotides of the complementarity regions of the oligonucleotides are non-natural nucleotides.

H40. The composition of embodiment H39, wherein each nucleotide of the complementarity regions of the oligonucleotides is a non-natural nucleotide.

H41. The composition of any one of embodiments H38-H40, wherein the non-natural nucleotides are locked nucleic acid (LNA) nucleotides.

H42. The composition of any one of embodiments H6-H41, wherein the oligonucleotides comprise one or more backbone modifications.

H43. The composition of any one of embodiments H1-H42, wherein each of the target nucleic acids comprising an overhang comprise a double-stranded portion and a single-stranded overhang.

H44. The composition of embodiment H43, wherein each of the target nucleic acids comprising an overhang comprise an overhang at one end or an overhang at both ends.

H45. The composition of embodiment H43 or H44, wherein an end, or both ends, of each of the target nucleic acids comprising an overhang independently comprises a 5' overhang or a 3' overhang.

H46. The composition of any one of embodiments H1-H45, wherein the target nucleic acids are, or are produced from, ribonucleic acids (RNAs).

H46.1 The composition of embodiment H46, wherein the RNAs are obtained from cells.

H47. The composition of any one of embodiments H1-H45, wherein the target nucleic acids are, or are produced from, deoxyribonucleic acids (DNAs).

H48. The composition of embodiment H47, wherein the DNAs are obtained from cells.

H49. The composition of embodiment H48, wherein the DNAs are, or are produced from, genomic DNAs.

H50. The composition of any one of embodiments H1-H49, wherein the target nucleic acids are obtained from a sample from an animal.

H51. The composition of embodiment H50, wherein the animal is an extinct animal.

H52. The composition of embodiment H50 or H51, wherein the animal is a mammal.

H53. The composition of embodiment H50, H51 or H52, wherein the animal is from the genus *Homo*.

H54. The composition of any one of embodiments H1-H46, H47, and H50-H53, wherein the target nucleic acids are, or are produced from, cell-free nucleic acids.

H55. The composition of embodiment H54, wherein the cell-free nucleic acids are obtained from a body fluid sample chosen from whole blood, blood plasma, blood serum, amniotic fluid, saliva, urine, pleural effusion, bronchial lavage, bronchial aspirates, breast milk, colostrum, tears, seminal fluid, peritoneal fluid, pleural effusion and stool.

H56. The composition of embodiment H54 or H55, wherein the cell-free nucleic acids comprise cell-free fetal DNAs.

H57. The composition of embodiment H54 or H55, wherein the cell-free nucleic acids comprise circulating cancer DNAs.

H58. The composition of embodiment H57, wherein the cell-free nucleic acids comprise circulating tumor DNAs.

H59. The composition of embodiment H54 or H55, wherein the cell-free nucleic acids comprise host and non-host DNAs.

H60. The composition of embodiment H59, wherein the non-host DNAs are from an infectious agent.

H61. The composition of embodiment H59, wherein the non-host DNAs are from a transplant.

H62. The composition of any one of embodiments H1-H61, wherein target nucleic acids are in solution.

H63. The composition of any one of embodiments H1-H62, wherein target nucleic acids are not in a fixed cell sample.

H64. The composition of any one of embodiments H1-H62, wherein target nucleic acids are not in a fixed tissue sample.

I1. A kit, comprising:
  the composition of any one of embodiments H1 to H64; and
  instructions for using the composition to produce a nucleic acid library.

I2. The kit of embodiment I1, further comprising a kinase adapted to 5' phosphorylate nucleic acids of a nucleic acid sample.

I3. The kit of embodiment I2, wherein the kinase is a polynucleotide kinase (PNK).

I4. The kit of any one of embodiments I1-I3, further comprising a DNA ligase.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for producing a nucleic acid library, comprising:
combining:
a nucleic acid composition comprising target nucleic acids, wherein some or all of the target nucleic acids comprise an overhang; and
an oligonucleotide pool comprising oligonucleotides, wherein:
some or all of the oligonucleotides comprise (i) a complementarity region capable of hybridizing to an overhang in a target nucleic acid, and (ii) a complementarity region identification polynucleotide,
the oligonucleotides in the pool comprising complementarity regions include complementarity regions of different lengths, and
the complementarity region identification polynucleotide is specific to one or more features of the complementarity region, wherein the one or more features comprise length of the complementarity region;
under conditions in which complementarity regions in the oligonucleotides hybridize to overhangs in the target nucleic acids having a corresponding length, thereby forming hybridization products for a nucleic acid library.

2. The method of claim 1, wherein the one or more features of the complementarity region further comprise (i) a 5' overhang, (ii) a 3' overhang, (iii) a particular sequence, (iv) a combination of (i) and (iii), or (v) a combination of (ii) and (iii).

3. The method of claim 1, wherein:
some of the target nucleic acids comprise no overhang; and
some of the oligonucleotides comprise no complementarity region and comprise an identification polynucleotide specific to no complementarity region.

4. The method of claim 1, wherein:
each target nucleic acid comprising an overhang comprises an overhang at one end or an overhang at both ends; and
an end, or both ends, of each target nucleic acid comprising an overhang independently comprises a 5' overhang or a 3' overhang.

5. The method of claim 1, wherein the target nucleic acids are, or are produced from, cell-free nucleic acids.

6. The method of claim 5, wherein the cell-free nucleic acids comprise cell-free fetal DNAs, circulating cancer DNAs, or host and non-host DNAs.

7. The method of claim 1, wherein the overhangs in the target nucleic acids are native overhangs.

8. The method of claim 7, wherein the native overhangs are not filled-in, cleaved, or introduced prior to combining with the pool.

9. The method of claim 7, wherein the target nucleic acids are not modified in length prior to combining with the pool.

10. The method of claim 1, wherein:
the oligonucleotide pool comprises oligonucleotides that comprise an overhang;
each of the oligonucleotides comprising an overhang comprise an overhang at one end or an overhang at both ends;
an end, or both ends, of each of the oligonucleotides comprising an overhang independently comprise a 5' overhang or a 3' overhang; and
at an end, the overhang comprises the complementarity region.

11. The method of claim 10, wherein the oligonucleotide pool comprises oligonucleotides that comprise different overhang polynucleotides for a particular overhang length.

12. The method of claim 10, wherein the oligonucleotide pool comprises oligonucleotides that comprise all possible overhang polynucleotide combinations for a particular overhang length.

13. The method of claim 10, wherein the oligonucleotide pool comprises oligonucleotides that comprise all possible overhang polynucleotide combinations for each overhang length.

14. The method of claim 10, wherein the overhang polynucleotides in the oligonucleotides of the pool are random.

15. The method of claim 10, wherein the oligonucleotide pool comprises oligonucleotides that comprise different overhang polynucleotides for a particular overhang length, and the overhang polynucleotides in the oligonucleotides of the pool are random.

16. The method of claim 10, wherein the oligonucleotides of the oligonucleotide pool comprise a portion other than the complementarity region and the complementarity region identification polynucleotide, wherein:
(i) the portion other than the complementarity region and the complementarity region identification polynucleotide comprises a nucleic acid binding domain;
(ii) the portion other than the complementarity region and the complementarity region identification polynucleotide comprises all or a portion of a sequencing adapter; or
(iii) a combination of (i) and (ii).

17. The method of claim 1, wherein oligonucleotides of the oligonucleotide pool are phosphorylated.

18. The method of claim 1, comprising, prior to combining the nucleic acid composition with the oligonucleotide pool, contacting the target nucleic acids in the composition with an agent comprising a phosphoryl transfer activity under conditions in which a 5' phosphate is added to a 5' end of target nucleic acids.

19. The method of claim 1, comprising contacting the hybridization products with an agent comprising a ligase activity under conditions in which an end of a target nucleic acid is covalently linked to an end of the oligonucleotide to which the target nucleic acid is hybridized.

20. A method for sequencing target nucleic acids, comprising:
performing a method of claim 1, thereby generating a nucleic acid library;
exposing the nucleic acid library to a sequencing process, wherein the sequencing process generates sequencing reads; and
(a) determining the sequence of one or more overhangs for the target nucleic acids based on the sequencing reads, (b) determining the sequence of one or more complementarity region identification polynucleotides based on the sequencing reads,
(c) determining lengths of one or more overhangs for the target nucleic acids, or
(d) determining a combination of two or three of (a), (b), and (c).

21. A method for analyzing one or more particular overhangs in a nucleic acid composition, comprising:
sequencing nucleic acids according to the method of claim 20; and
quantifying the amount of one or more particular overhangs in target nucleic acids, thereby generating one or more overhang quantifications, wherein each overhang quantification is for an overhang characterized as (i) a 5' overhang, (ii) a 3' overhang, (iii) a particular sequence, (iv) a particular length, or (v) a combination of two, three or four of (i), (ii), (iii), and (iv).

22. The method of claim 21, further comprising classifying the sequencing reads by source of origin based on overhang content.

23. The method of claim 1, wherein each complementarity region identification polynucleotide comprises a nucleic acid sequence that is unique for each oligonucleotide comprising a complementarity region of a particular length.

24. The method of claim 1, wherein each complementarity region identification polynucleotide comprises a nucleic acid sequence that is unique for each oligonucleotide comprising a complementarity region of a particular length and a particular 5' or 3' directionality.

\* \* \* \* \*